United States Patent
Cho et al.

(10) Patent No.: US 11,800,730 B2
(45) Date of Patent: Oct. 24, 2023

(54) ORGANIC LIGHT EMITTING DEVICE

(71) Applicant: LG CHEM, LTD., Seoul (KR)

(72) Inventors: Seong Mi Cho, Daejeon (KR); Min Woo Jung, Daejeon (KR); Dong Hoon Lee, Daejeon (KR); Tae Yoon Park, Daejeon (KR); Jeong Wook Mun, Daejeon (KR); Jung Ha Lee, Daejeon (KR); Ju Young Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 157 days.

(21) Appl. No.: 15/747,038

(22) PCT Filed: Aug. 9, 2017

(86) PCT No.: PCT/KR2017/008641
§ 371 (c)(1),
(2) Date: Jan. 23, 2018

(87) PCT Pub. No.: WO2018/093015
PCT Pub. Date: May 24, 2018

(65) Prior Publication Data
US 2019/0013490 A1     Jan. 10, 2019

(30) Foreign Application Priority Data
Nov. 16, 2016 (KR) .......................... 10-2016-0152691
Jul. 26, 2017 (KR) .......................... 10-2017-0094877

(51) Int. Cl.
*H10K 50/11* (2023.01)
*C07D 405/04* (2006.01)
(Continued)

(52) U.S. Cl.
CPC ........... *H10K 50/11* (2023.02); *C07D 209/86* (2013.01); *C07D 209/88* (2013.01); *C07D 401/14* (2013.01); *C07D 405/04* (2013.01); *C07D 405/14* (2013.01); *C07D 409/04* (2013.01); *C09B 57/00* (2013.01); *C09B 57/008* (2013.01);
(Continued)

(58) Field of Classification Search
CPC ........ H01L 2251/5384; H01L 51/5004; H10K 50/11; H10K 2101/40; H10K 2101/90
See application file for complete search history.

(56) References Cited

U.S. PATENT DOCUMENTS 7,274,141 B2   9/2007   Leo et al.
8,911,881 B2   12/2014  Lee et al.
(Continued)

FOREIGN PATENT DOCUMENTS

CN   107710441   2/2018
CN   108064258   5/2018
(Continued)

OTHER PUBLICATIONS

Daintith, John, Dictionary of Chemistry, 2008, Oxford University Press, 6th Edition. (Year: 2008).*
(Continued)

*Primary Examiner* — Sean M DeGuire
(74) *Attorney, Agent, or Firm* — Bryan Cave Leighton Paisner LLP

(57) ABSTRACT

The present invention provides an organic light emitting device having improved driving voltage, efficiency and lifetime.

6 Claims, 3 Drawing Sheets

(51) Int. Cl.

| | |
|---|---|
| *C07D 405/14* | (2006.01) |
| *C09B 57/00* | (2006.01) |
| *C07D 209/88* | (2006.01) |
| *C07D 209/86* | (2006.01) |
| *C07D 401/14* | (2006.01) |
| *C09K 11/06* | (2006.01) |
| *C07D 409/04* | (2006.01) |
| *H10K 50/81* | (2023.01) |
| *H10K 50/82* | (2023.01) |
| *H10K 50/17* | (2023.01) |
| *H10K 85/60* | (2023.01) |
| *H10K 50/15* | (2023.01) |
| *H10K 50/16* | (2023.01) |
| *H10K 101/40* | (2023.01) |
| *H10K 101/10* | (2023.01) |
| *H10K 101/00* | (2023.01) |

(52) U.S. Cl.
CPC ............ *C09K 11/06* (2013.01); *H10K 50/171* (2023.02); *H10K 50/81* (2023.02); *H10K 50/82* (2023.02); *H10K 85/615* (2023.02); *H10K 85/622* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 2101/10* (2023.02); *H10K 2101/40* (2023.02); *H10K 2101/90* (2023.02)

(56) References Cited

U.S. PATENT DOCUMENTS

| | | | |
|---|---|---|---|
| 9,614,170 B2 | 4/2017 | Ogiwara et al. | |
| 9,728,729 B2 | 8/2017 | Kim et al. | |
| 2008/0074038 A1 | 3/2008 | Kim et al. | |
| 2011/0260138 A1* | 10/2011 | Xia | H01L 51/0074 548/440 |
| 2012/0205632 A1 | 8/2012 | Shitagaki et al. | |
| 2012/0256535 A1 | 10/2012 | Seo et al. | |
| 2013/0112952 A1* | 5/2013 | Adamovich | C09B 57/00 257/40 |
| 2013/0256645 A1* | 10/2013 | Min | H01L 51/006 257/40 |
| 2015/0194622 A1 | 7/2015 | Yamamoto et al. | |
| 2015/0207079 A1* | 7/2015 | Cho | H01L 51/0054 257/40 |
| 2015/0340626 A1 | 11/2015 | Lee et al. | |
| 2016/0093808 A1 | 3/2016 | Adamovich | |
| 2016/0126472 A1 | 5/2016 | Oh et al. | |
| 2016/0155977 A1 | 6/2016 | Kim | |
| 2016/0226001 A1* | 8/2016 | Parham | H01L 51/0072 |
| 2016/0372688 A1* | 12/2016 | Seo | H01L 51/0085 |
| 2017/0054087 A1 | 2/2017 | Zeng et al. | |
| 2017/0125699 A1* | 5/2017 | Ahn | H01L 51/0052 |
| 2017/0186965 A1* | 6/2017 | Parham | C07D 403/14 |
| 2017/0207399 A1 | 7/2017 | Parham et al. | |
| 2018/0037546 A1 | 2/2018 | Sugino et al. | |
| 2019/0006590 A1 | 1/2019 | Park et al. | |
| 2019/0165282 A1* | 5/2019 | Parham | H01L 51/0034 |
| 2019/0202851 A1* | 7/2019 | Stoessel | C07F 15/0033 |

FOREIGN PATENT DOCUMENTS

| | | | |
|---|---|---|---|
| EP | 3336159 A1 | 6/2018 | |
| JP | 2012227524 A | 11/2012 | |
| JP | 2014075249 A | 4/2014 | |
| JP | 2015218165 A | 12/2015 | |
| JP | 2016184758 A | 10/2016 | |
| JP | 2016532307 A | 10/2016 | |
| JP | 2017524707 A | 8/2017 | |
| JP | 2018531480 A | 10/2018 | |
| KR | 20000051826 A | 8/2000 | |
| KR | 10-2006-0059321 A | 6/2006 | |
| KR | 10-2008-0028212 A | 3/2008 | |
| KR | 10-2014-0105913 A | 9/2014 | |
| KR | 10-2015-0030660 A | 3/2015 | |
| KR | 10-2015-0077587 A | 7/2015 | |
| KR | 10-2015-0126525 A | 11/2015 | |
| KR | 10-2015-0136027 A | 12/2015 | |
| KR | 10-2016-0026744 A | 3/2016 | |
| KR | 10-2016-0028524 A | 3/2016 | |
| KR | 10-2016-0063753 A | 6/2016 | |
| KR | 10-2016-0076461 A | 6/2016 | |
| KR | 10-2016-0080090 A | 7/2016 | |
| TW | 201609675 A | 3/2016 | |
| WO | 03/012890 A2 | 2/2003 | |
| WO | 2015/170882 A1 | 11/2015 | |
| WO | 2015169412 | 11/2015 | |
| WO | 2016/129672 A1 | 8/2016 | |
| WO | 2017178311 A1 | 10/2017 | |
| WO | WO-2017188597 A1 * | 11/2017 | ............ C07D 209/86 |
| WO | 2018016742 A1 | 1/2018 | |
| WO | WO-2018043435 A1 * | 3/2018 | ............ C09K 11/06 |

OTHER PUBLICATIONS

"White-light electroluminescent organic devices based on efficient energy harvesting of singlet and triplet excited states using blue-light exciplex", Applied Physics Express 7, 052102 (2014) pp. 1-5.
"Photoelectron Spectrophotometer in Air Surface Analyzer Model AC-3", Jun. 11, 2012, p. 1-6, XP055029420.
Office Action of Chinese Patent Office in Appl'n No. 201780002810.2 dated Jan. 14, 2020.

* cited by examiner

[FIG. 1]
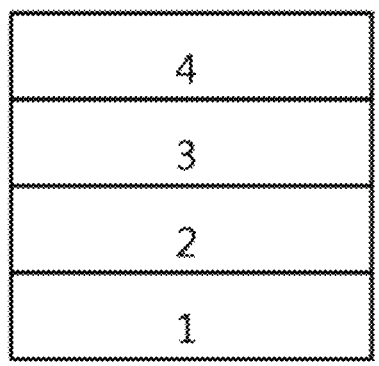
[FIG. 2]
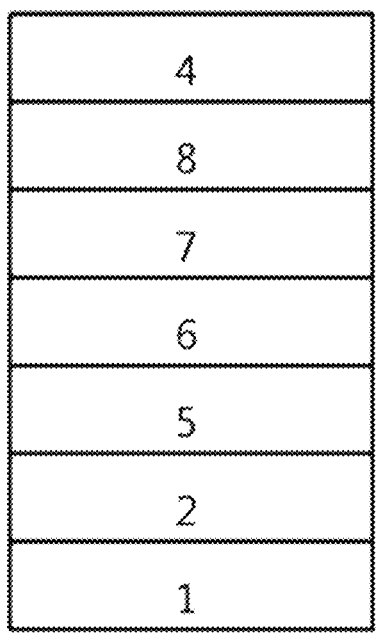

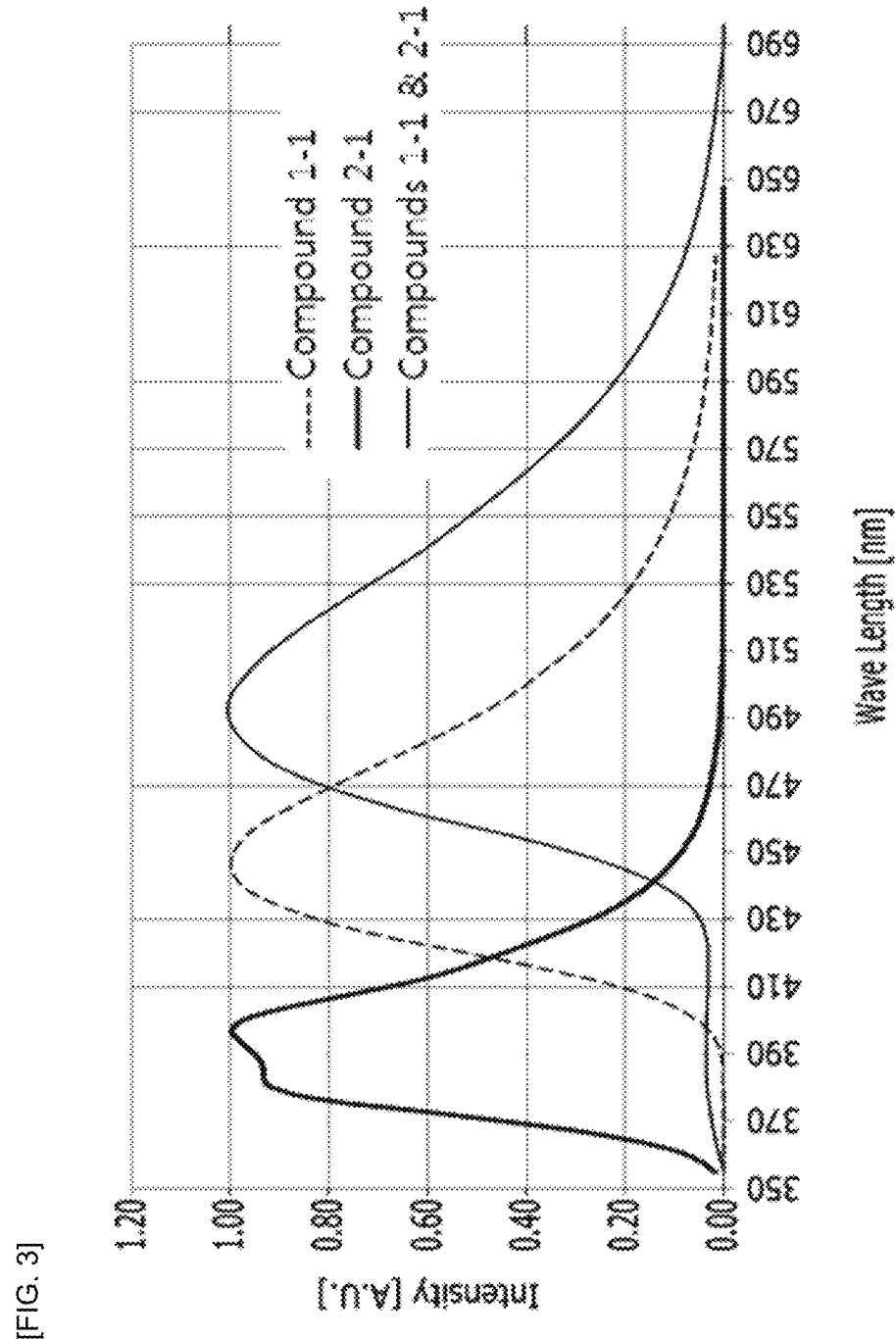
[FIG. 3]

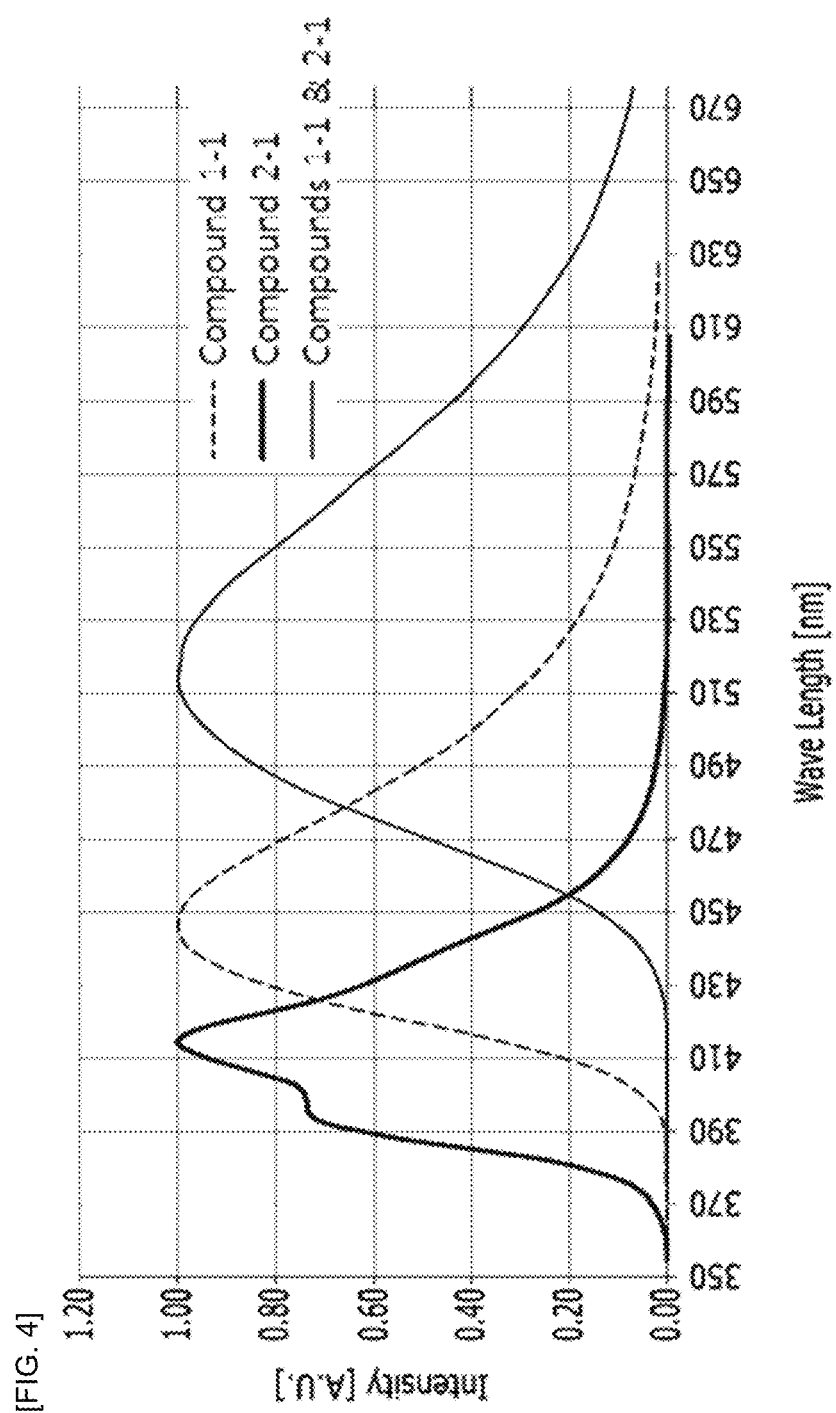
[FIG. 4]

ORGANIC LIGHT EMITTING DEVICE

CROSS-REFERENCE TO RELATED APPLICATION(S)

This application is a National Stage Entry of International Application No. PCT/KR2017/008641, filed on Aug. 9, 2017, and claims the benefit of and priority to Korean Application No. 10-2016-0152691, filed on Nov. 16, 2016, and Korean Application No. 10-2017-0094877, filed on Jul. 26, 2017 all of which are hereby incorporated by reference in their entirety for all purposes as if fully set forth herein.

TECHNICAL FIELD

The present invention relates to an organic light emitting device having improved driving voltage, efficiency and lifetime.

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing demand for developing an organic light emitting device having improved driving voltage, efficiency and lifetime.

PRIOR ART LITERATURE

Patent Literature (Patent Literature 1) Korean Patent Laid-open Publication No. 10-2000-0051826

DETAILED DESCRIPTION OF THE INVENTION

Technical Problem

It is an object of the present invention to provide an organic light emitting device having improved driving voltage, efficiency and lifetime.

Technical Solution

The present invention provides an organic light emitting device comprising: a cathode; an anode; and at least one light emitting layer interposed between the cathode and the anode wherein the light emitting layer includes a first host and a second host, the first host has a HOMO of 5.6 eV to 6.4 eV, the second host has a HOMO of 5.4 eV to 5.8 eV, and a difference between the HOMO of the first host and the HOMO of the second host is 0.2 eV or more, and wherein the maximum emission wavelength of the mixture of the first host and the second host is 20 nm or more higher than the maximum emission wavelength of the first host.

Advantageous Effects

The organic light emitting device described above is excellent in driving voltage, efficiency, and lifetime.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting element comprising a substrate 1, an anode 2, a hole injection layer 5, a hole transport layer 6, a light emitting layer 7, an electron transport layer 8 and a cathode 4.

FIGS. 3 and 4 illustrates $PL_{max}$ measurement results for a first host, a second host and a mixture thereof according to the present invention.

DETAILED DESCRIPTION OF THE EMBODIMENTS

Hereinafter, the present invention will be described in more detail to help understanding of the present invention.

In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are connected or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto.

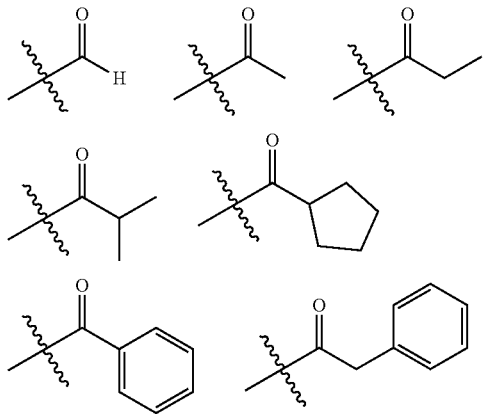

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

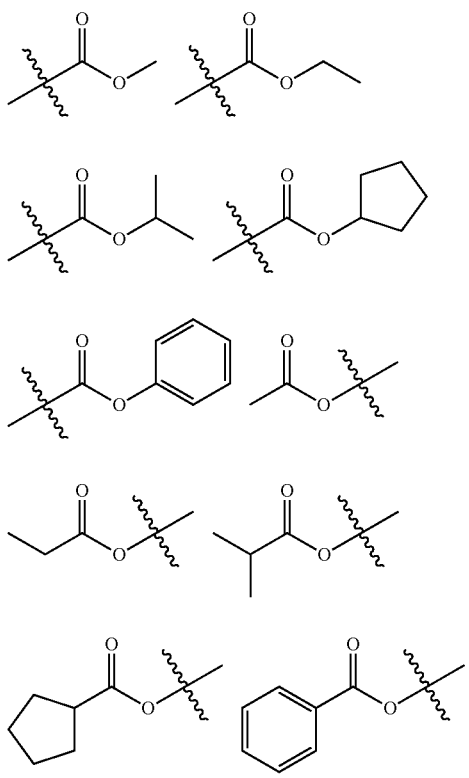

In the present specification, the number of carbon atoms in an imide group is not particularly limited but is preferably 1 to 25. Specifically, the imide group may be compounds having the following structures, but is not limited thereto.

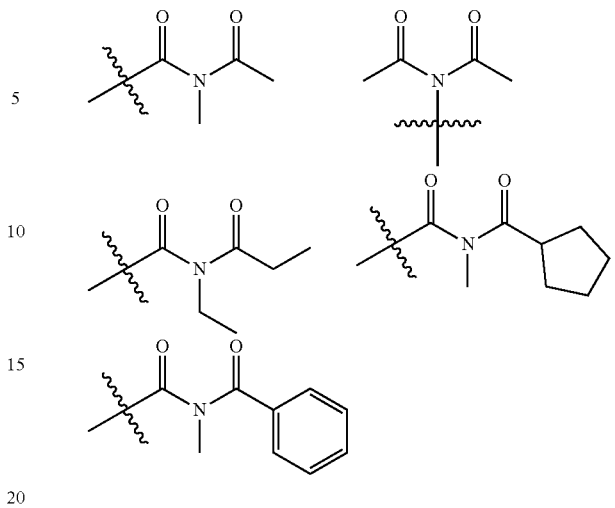

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be bonded to each other to form a spiro structure. In the case where the fluorenyl group is substituted,

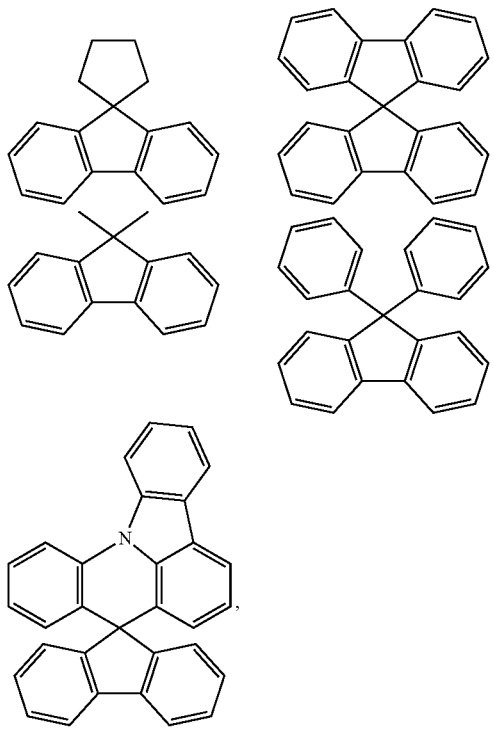

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

The present invention provides an organic light emitting device comprising: a cathode; an anode; and at least one light emitting layer interposed between the cathode and an anode, wherein the light emitting layer includes a first host and a second host, the first host has a HOMO of 5.6 eV to 6.4 eV, the second host has a HOMO of 5.4 eV to 5.8 eV, and a difference between the HOMO of the first host and the HOMO of the second host is 0.2 eV or more, and wherein the maximum emission wavelength of the mixture of the first host and the second host is 20 nm or more higher than the maximum emission wavelength of the first host.

Hereinafter, the present invention will be described in detail for each configuration.

Anode and Cathode

The anode and the cathode used in the present invention mean an electrode used in an organic light emitting device.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

In addition, a hole injection layer may be further included on the anode. The hole injection layer is composed of a hole injection material, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability.

It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

Light Emitting Layer

The light emitting layer according to the present invention includes a first host and a second host, wherein the light emitting layer includes a first host and a second host, the first host has a HOMO of 5.6 eV to 6.4 eV, the second host has a HOMO of 5.4 eV to 5.8 eV, and a difference between the HOMO of the first host and the HOMO of the second host is 0.2 eV or more, and wherein the maximum emission wavelength of the mixture of the first host and the second host is 20 nm or more higher than the maximum emission wavelength of the first host.

When the above-described first host compound is used for a light emitting layer as a single host, the difference in HOMO from the peripheral hole-transporting layer is large, a hole barrier is generated, hole transfer to the light emitting layer becomes not easy and light emitting zone is formed adjacent to the hole transport layer. For these reasons, the balance between holes and electrons does not match, resulting in a decrease in efficiency and lifetime. Therefore, by using the hole-transporting second host together, the efficiency and lifetime of the organic light-emitting device can be improved.

Preferably, the light emitting layer includes a first host compound represented by the following Chemical Formula 1-1 or Chemical Formula 1-2 and a second host compound represented by the following Chemical Formula 2:

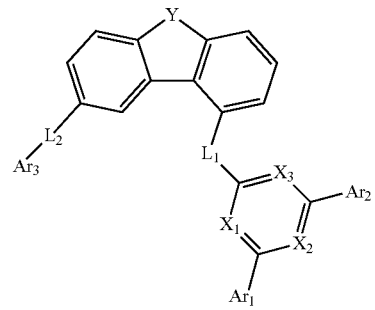

[Chemical Formula 1-1]

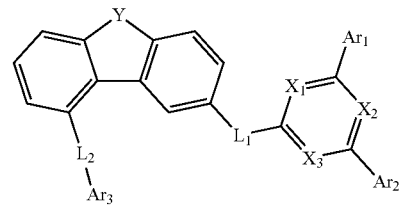

[Chemical Formula 1-2]

in Chemical Formulae 1-1 and 1-2,
Y is O, S, or SiR$_1$R$_2$,
X$_1$ to X$_3$ are each independently N, or CR$_3$, provided that at least one of X$_1$ to X$_3$ is N,
L$_1$ and L$_2$ are each independently a single bond; a substituted or unsubstituted C$_{6-60}$ arylene; or a substituted or unsubstituted C$_{2-60}$ heteroarylene containing at least one of O, N, Si and S,
Ar$_1$ and Ar$_2$ are each independently a substituted or unsubstituted C$_{6-60}$ aryl; or a substituted or unsubstituted C$_{2-60}$ heteroaryl containing at least one of O, N, Si and S,
Ar$_3$ is a substituted or unsubstituted C$_{6-60}$ aryl,
R$_1$, R$_2$ and R$_3$ are each independently hydrogen; deuterium; halogen; cyano; nitro; amino; a substituted or unsubstituted C$_{1-60}$ alkyl; a substituted or unsubstituted C$_{1-60}$ haloalkyl; a substituted or unsubstituted C$_{1-60}$ haloalkoxy; a substituted or unsubstituted C$_{3-60}$ cycloalkyl; a substituted or unsubstituted C$_{2-60}$ alkenyl; a substituted or unsubstituted C$_{6-60}$ aryl; or a substituted or unsubstituted C$_{1-60}$ heteroaryl containing at least one of O, N, Si and S,

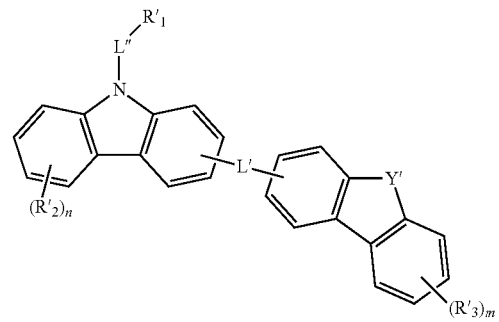

[Chemical Formula 2]

in Chemical Formula 2,
Y' is O, S, NR', or CR'R",
R' and R" are each independently hydrogen; deuterium; halogen; cyano; nitro; amino; a substituted or unsubstituted $C_{1-60}$ alkyl; a substituted or unsubstituted $C_{1-60}$ haloalkyl; a substituted or unsubstituted $C_{1-60}$ haloalkoxy; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{1-60}$ heteroaryl containing at least one of O, N, Si and S, or R' and R" together form a substituted or unsubstituted $C_{6-60}$ aromatic ring, L' and L" are each independently a single bond, a substituted or unsubstituted $C_{6-60}$ arylene, or a substituted or unsubstituted $C_{2-60}$ heteroarylene containing at least one of O, N, Si and S, $R'_1$ is a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing at least one of O, N, Si and S, $R'_2$ and $R'_3$ are each independently hydrogen; deuterium; halogen; cyano; a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing at least one of O, N, Si and S, and n and m are each independently an integer of 0 to 4.

In Chemical Formula 1, preferably, $X_1$ to $X_3$ are each independently N or CH, provided that at least one of $X_1$ to $X_3$ is N.

Preferably, $L_1$ is a single bond, phenylene, phenylene substituted with cyano, or pyridinylene substituted with phenyl.

Preferably, $L_2$ is a single bond, phenylene, naphthylene, phenanthrenylene, or pyridinylene.

Preferably, $Ar_1$ and $Ar_2$ are each independently phenyl, phenyl substituted with cyano, phenyl substituted with one to five deuterium, biphenyl, or dibenzofuranyl.

Preferably, $Ar_3$ is any one selected from the group consisting of:

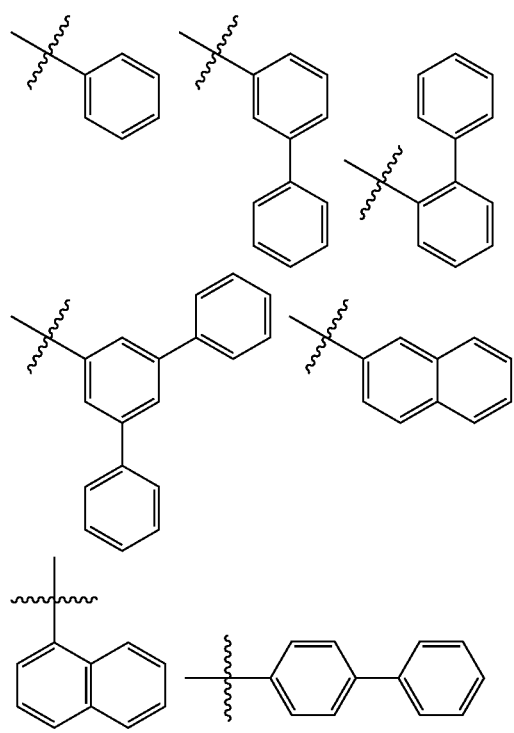

-continued

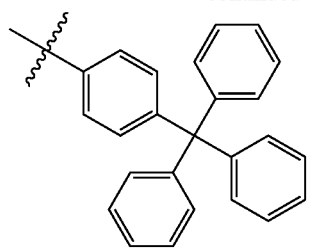

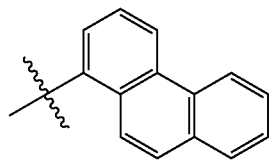

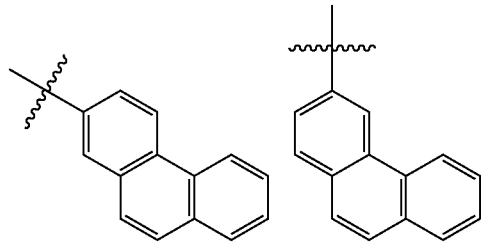

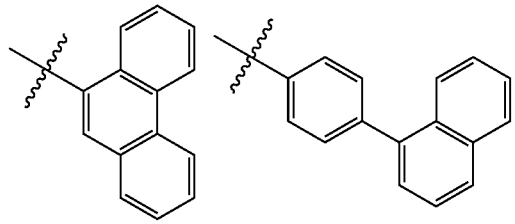

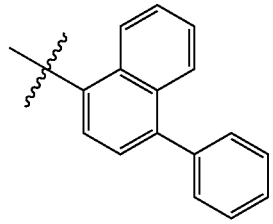

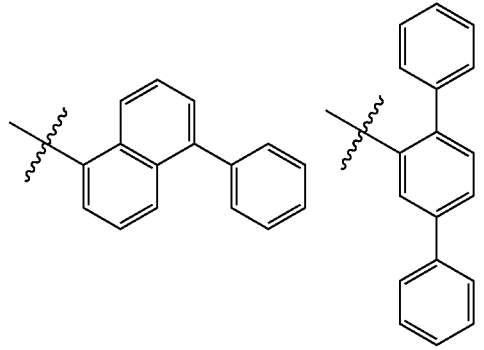

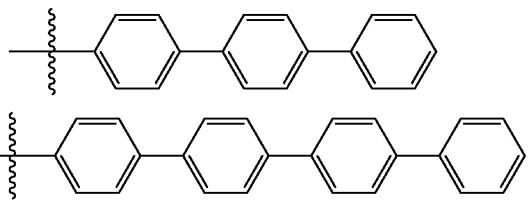

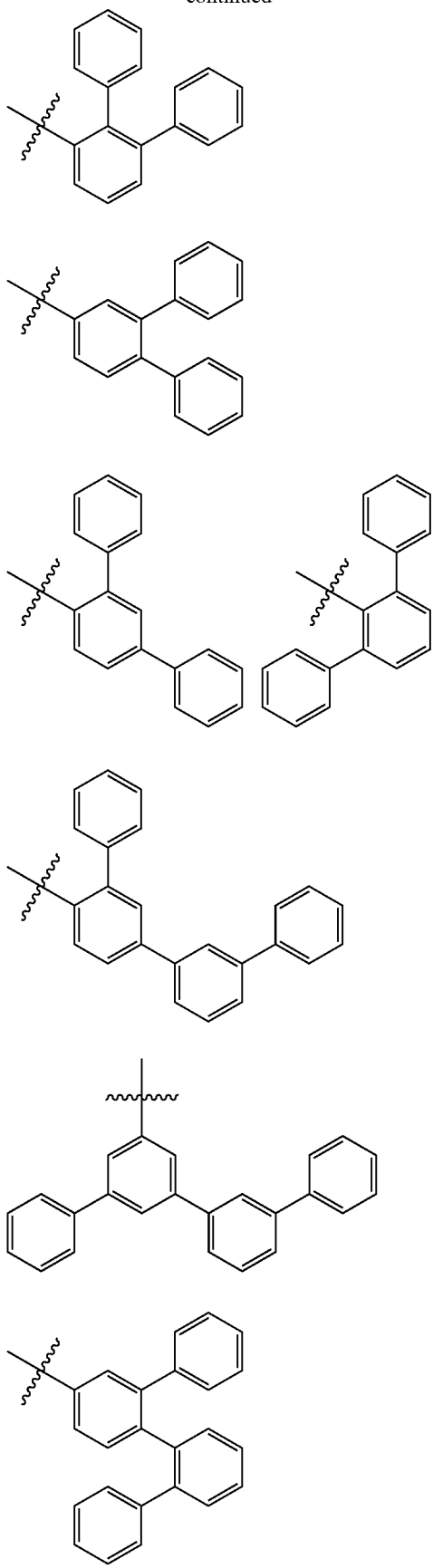

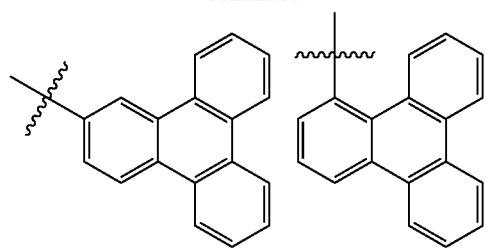
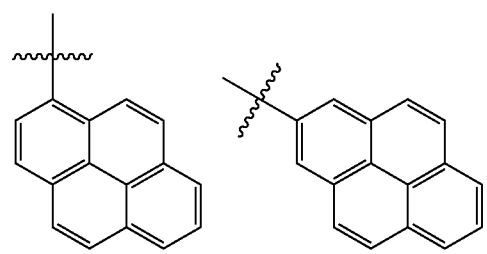
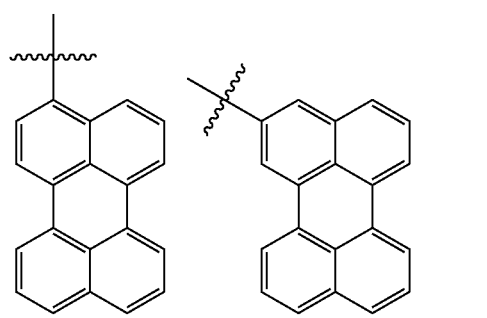
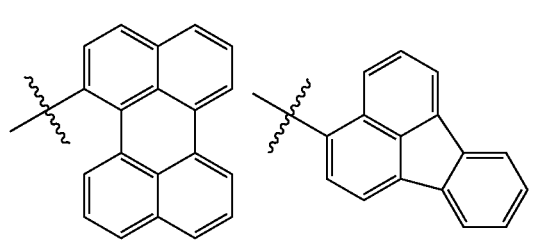
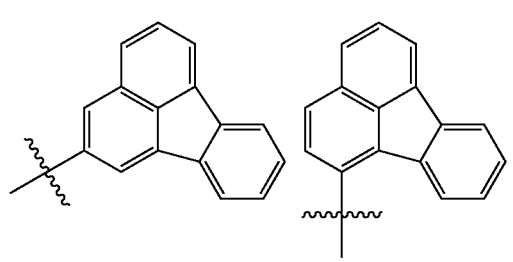
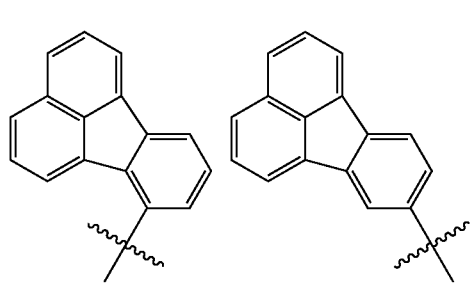
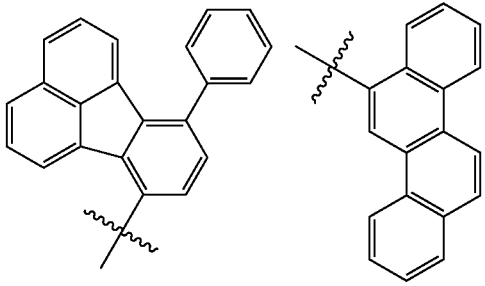
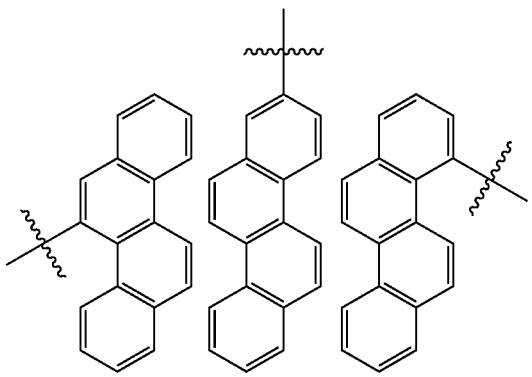
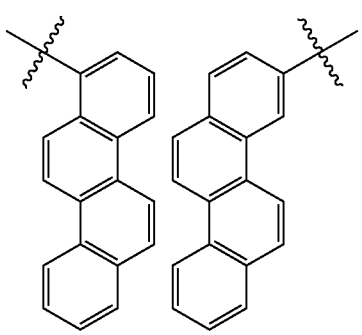
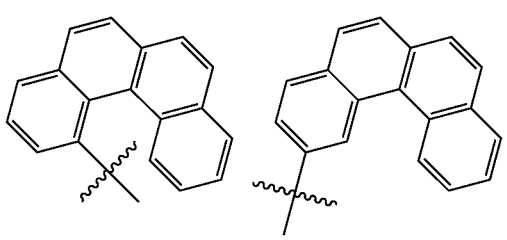
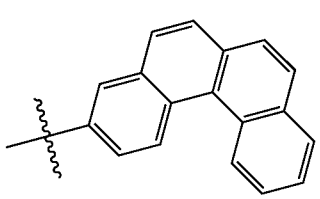
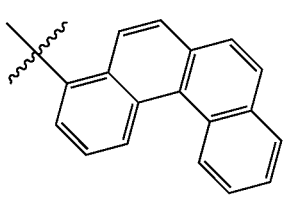

-continued
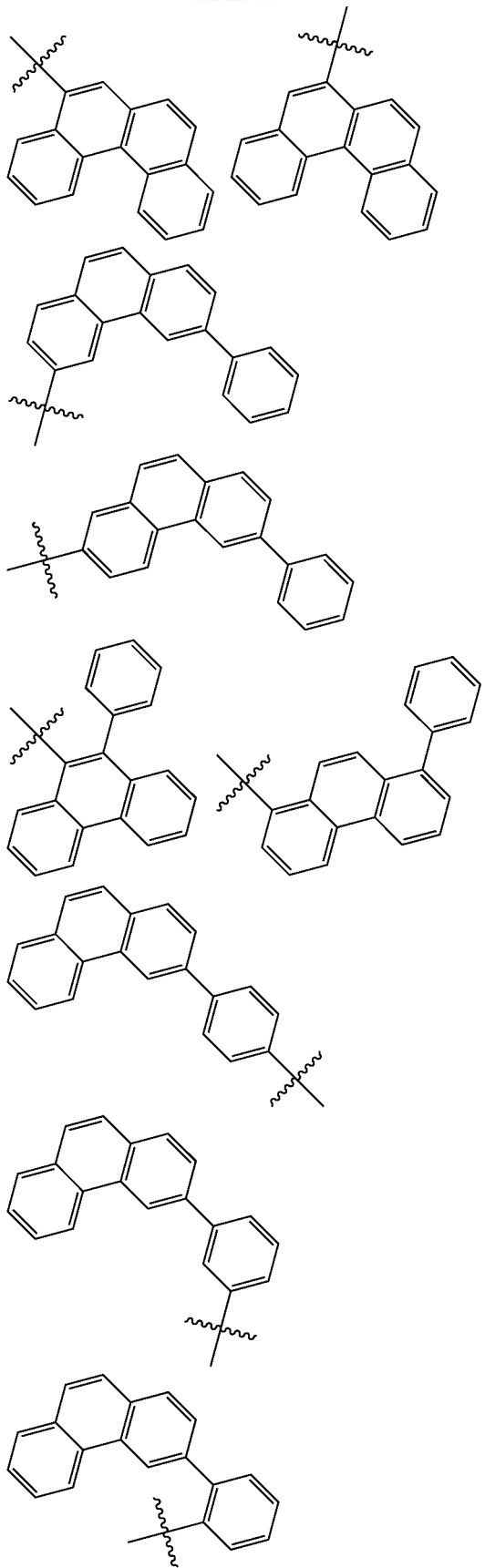
-continued
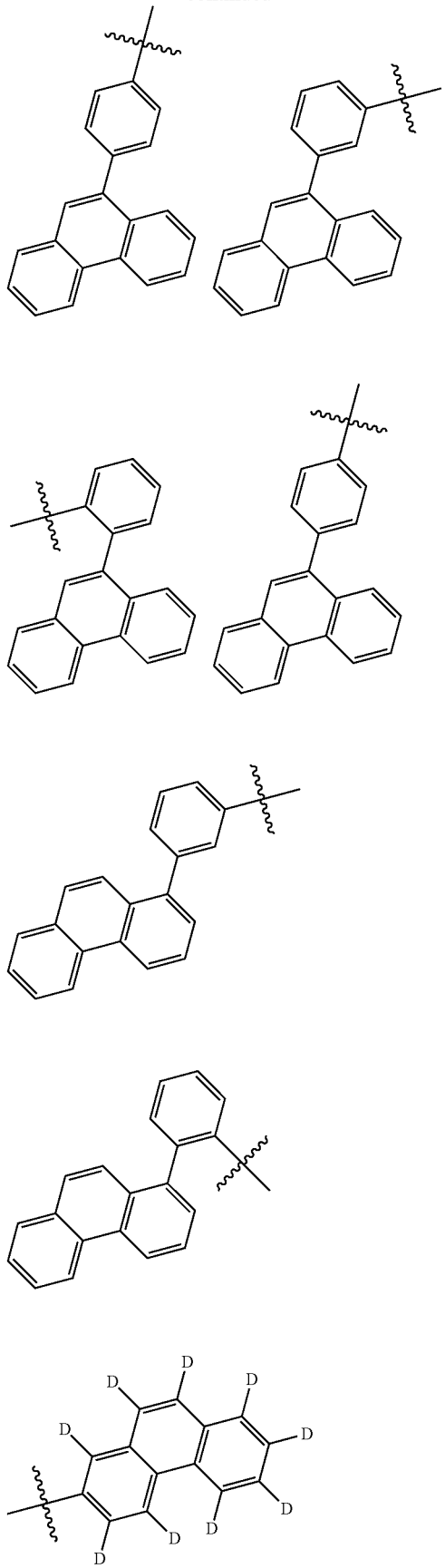

-continued
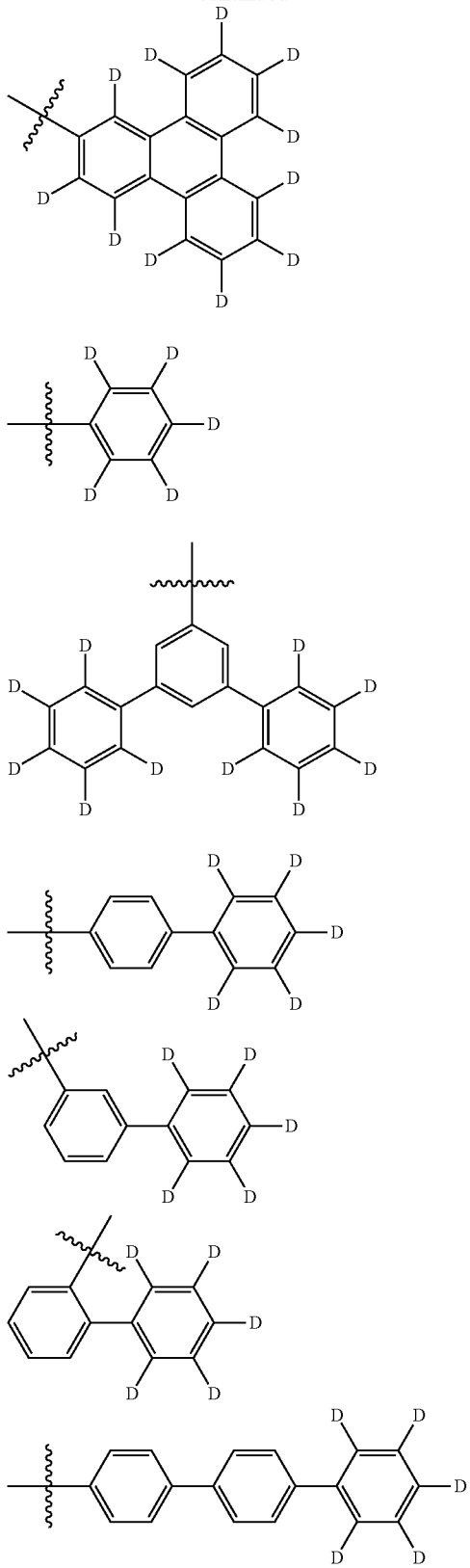
More preferably, Ar₃ is phenyl, phenyl substituted with one to five deuterium, biphenyl, terphenyl, quaterphenyl, naphthyl, triphenylenyl, phenanthrenyl, or pyrenyl.
Representative examples of the compounds represented by Chemical Formulae 1-1 or 1-2 are as follows:
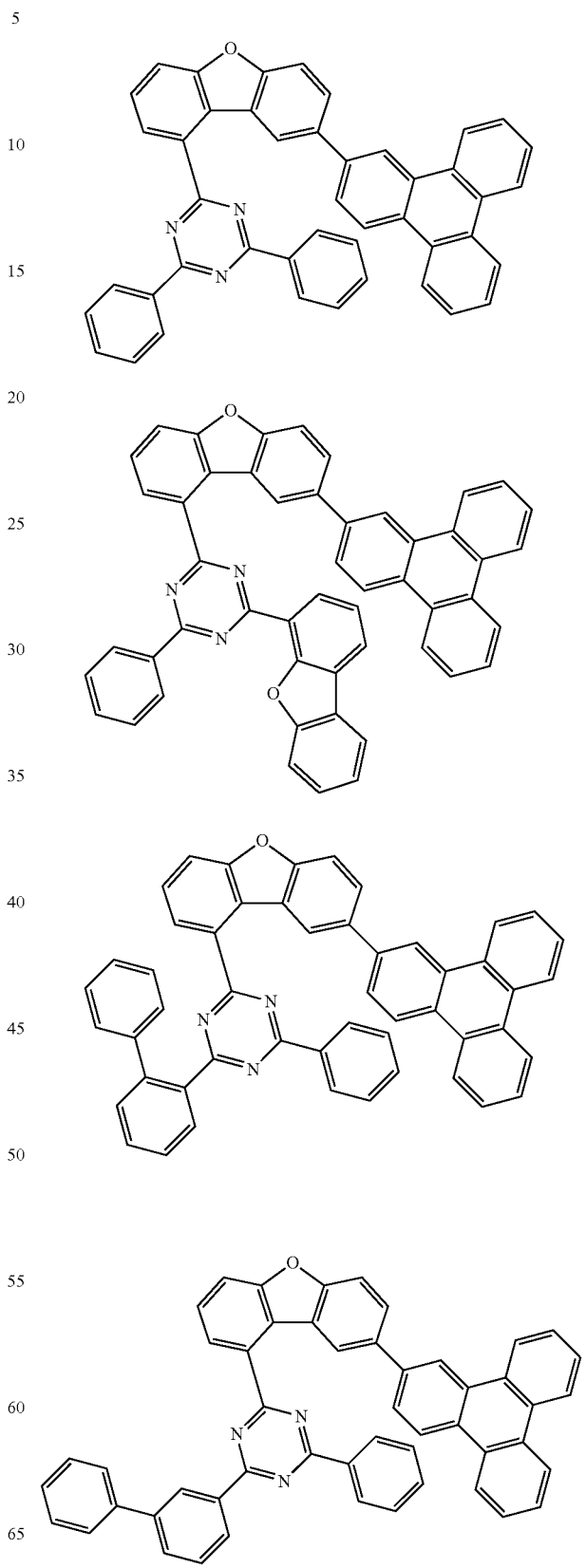

-continued
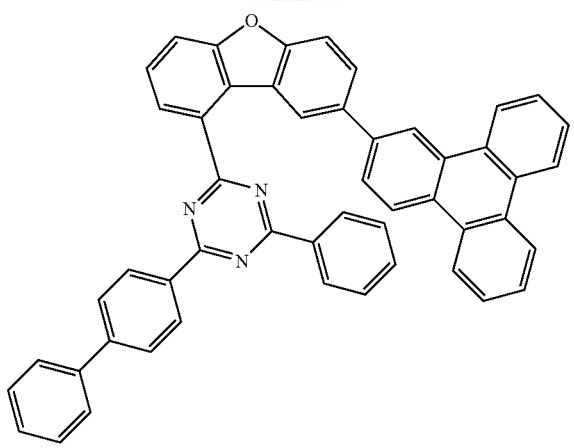
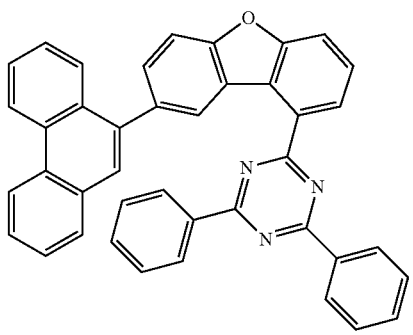
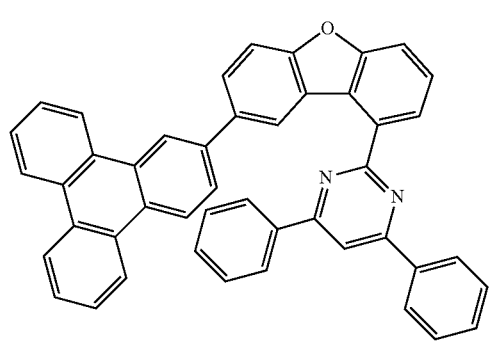
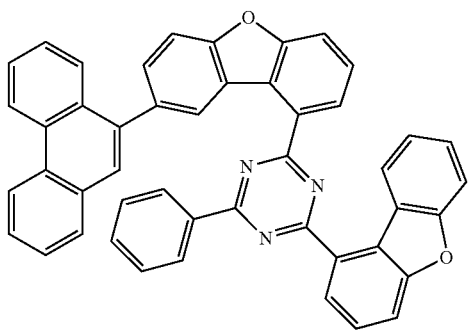
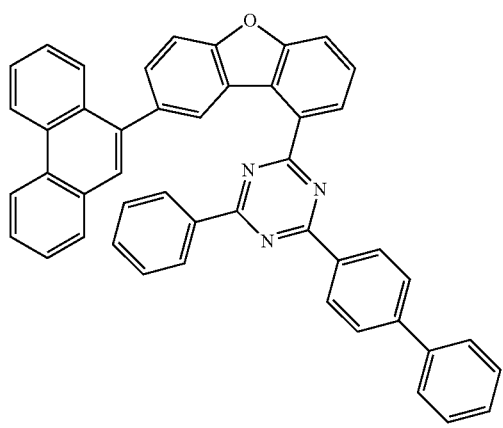
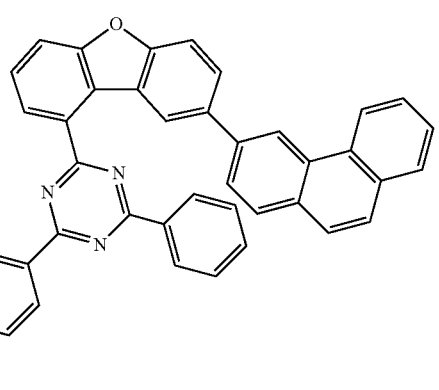
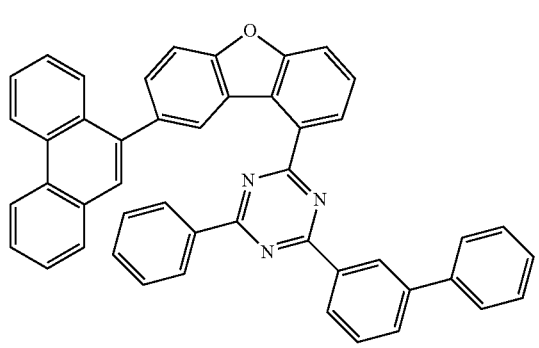
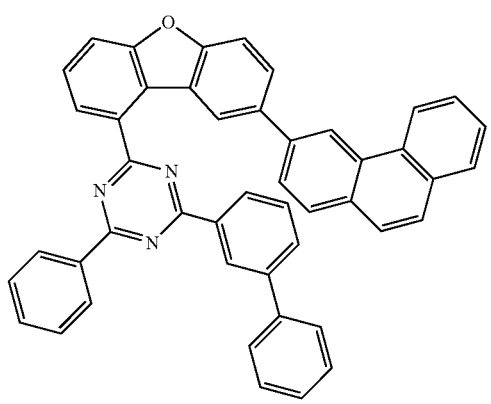

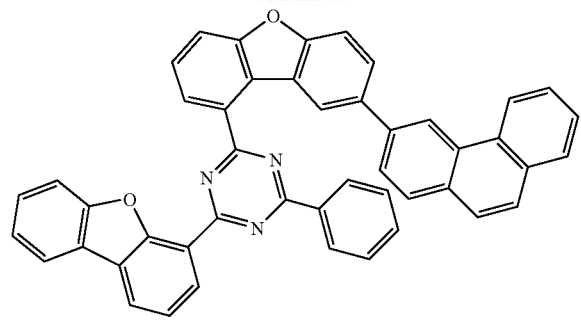
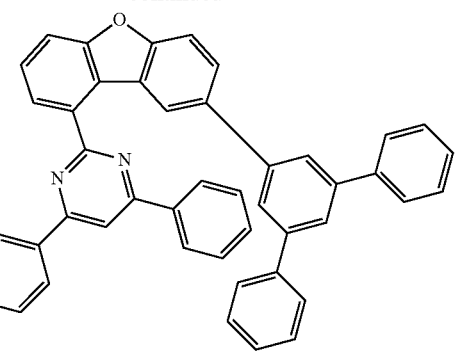
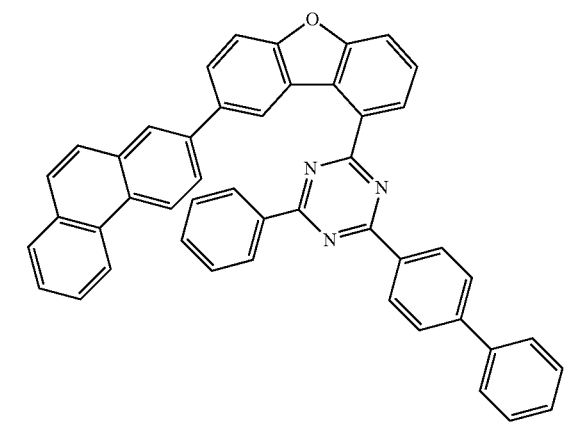
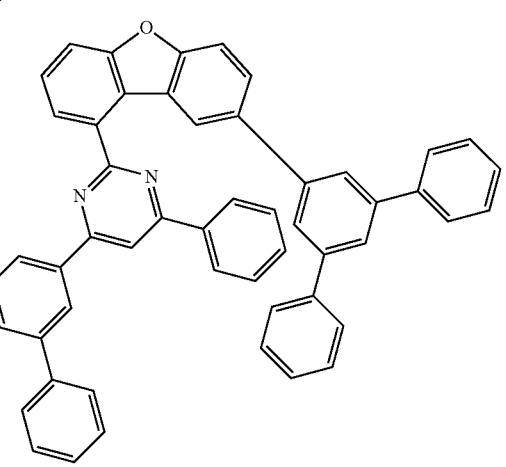
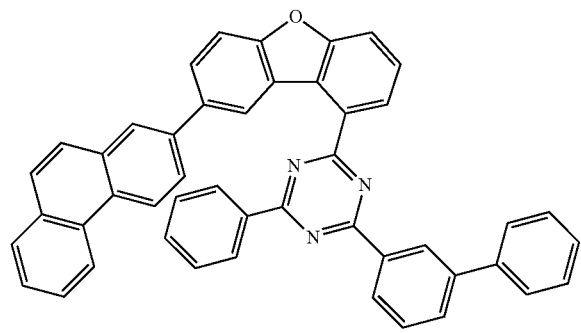
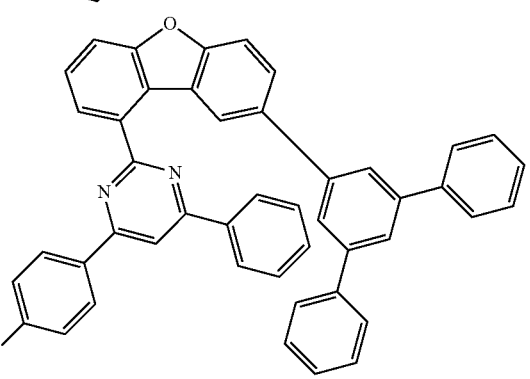
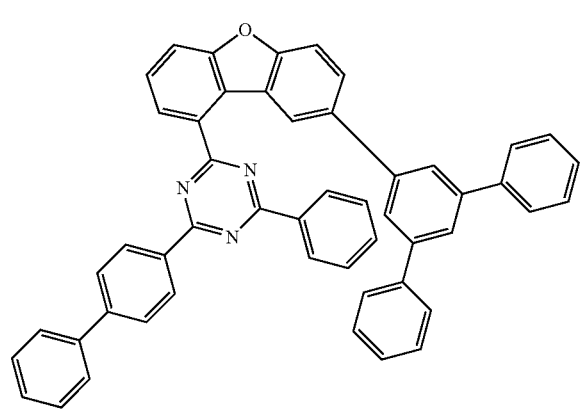
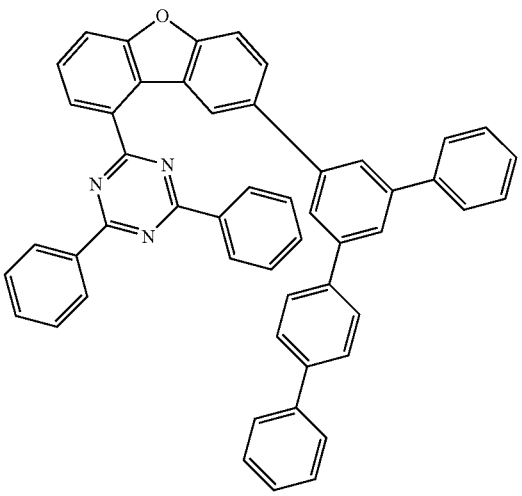

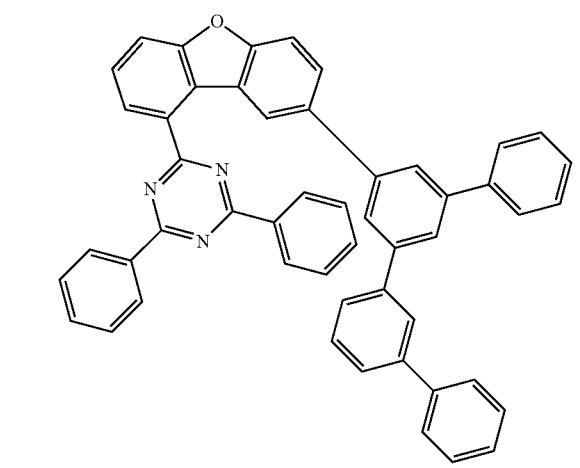
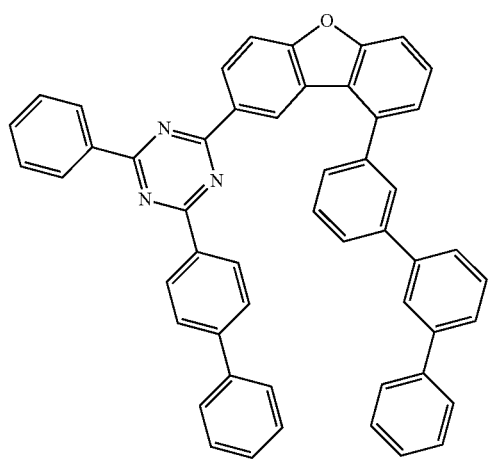
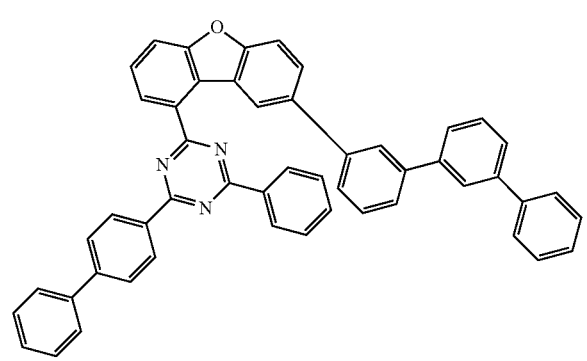
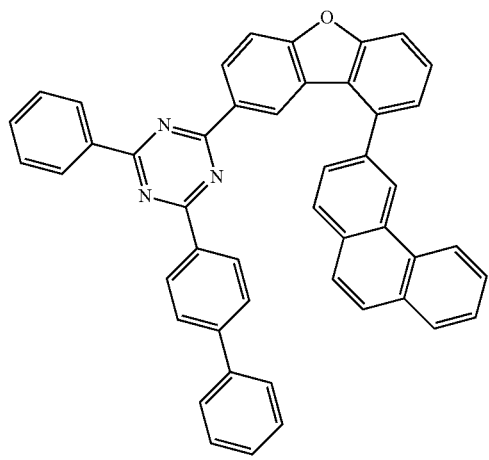
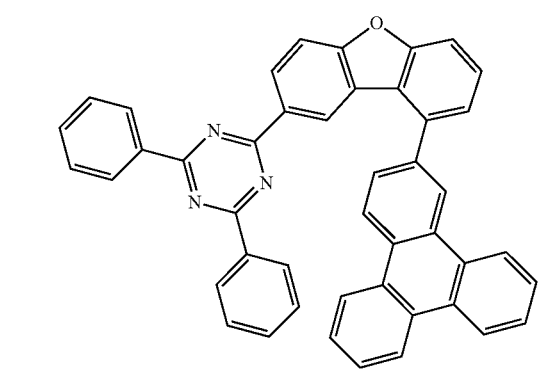
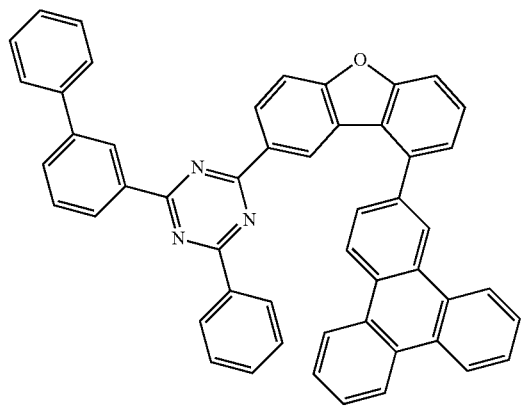
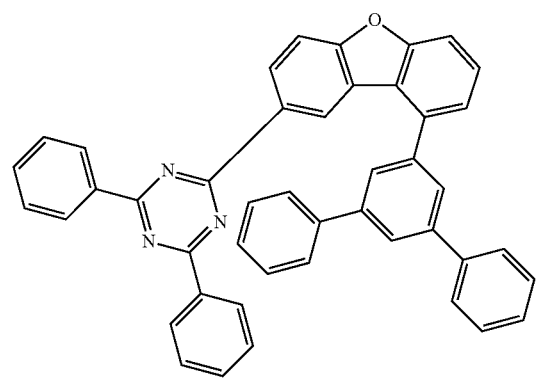
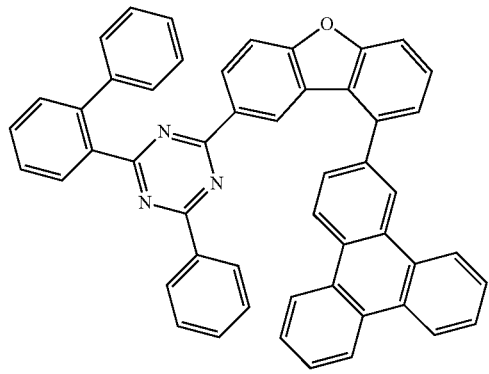

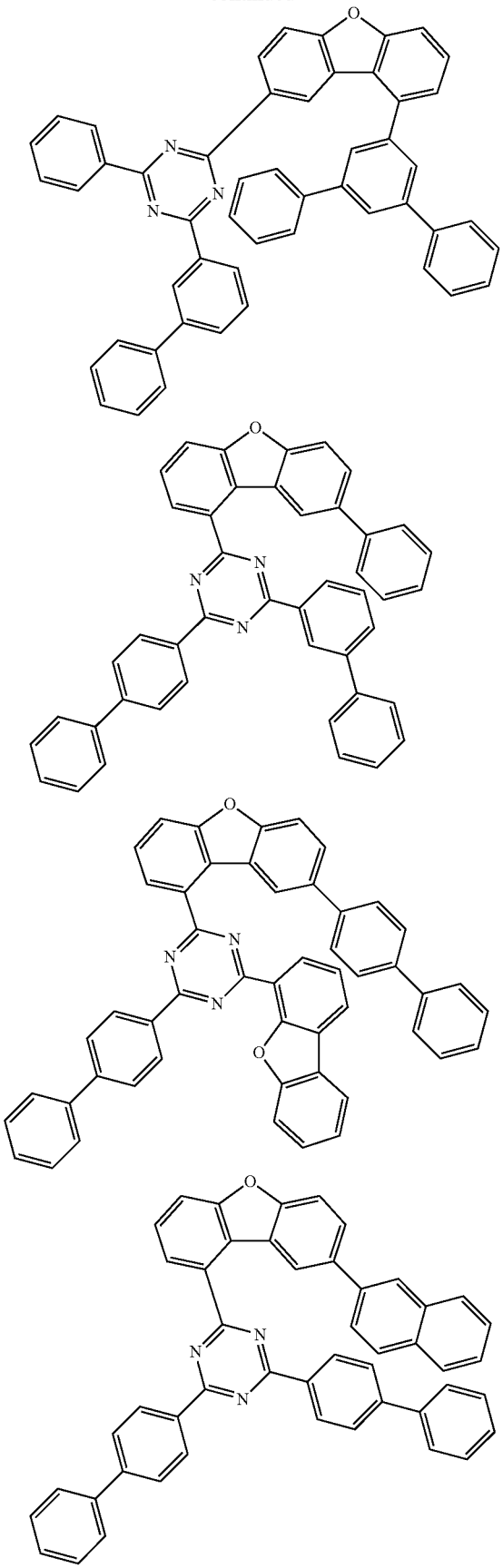
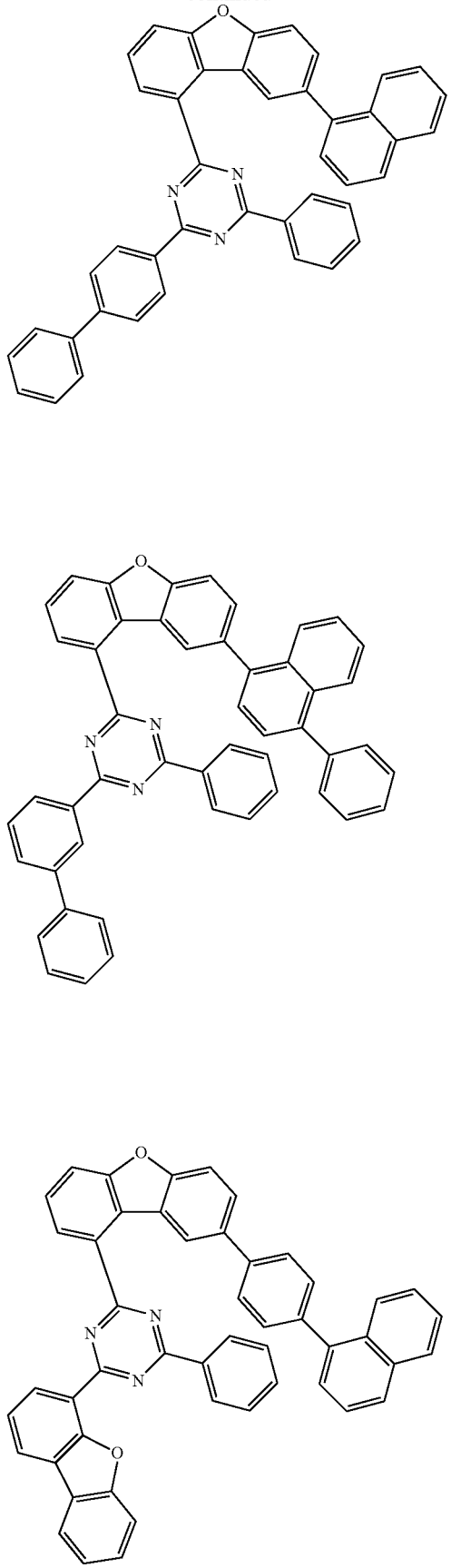

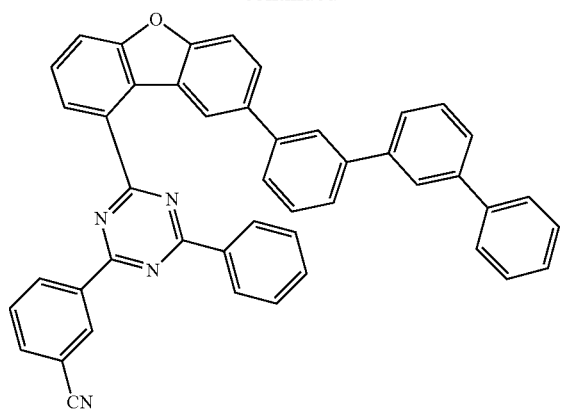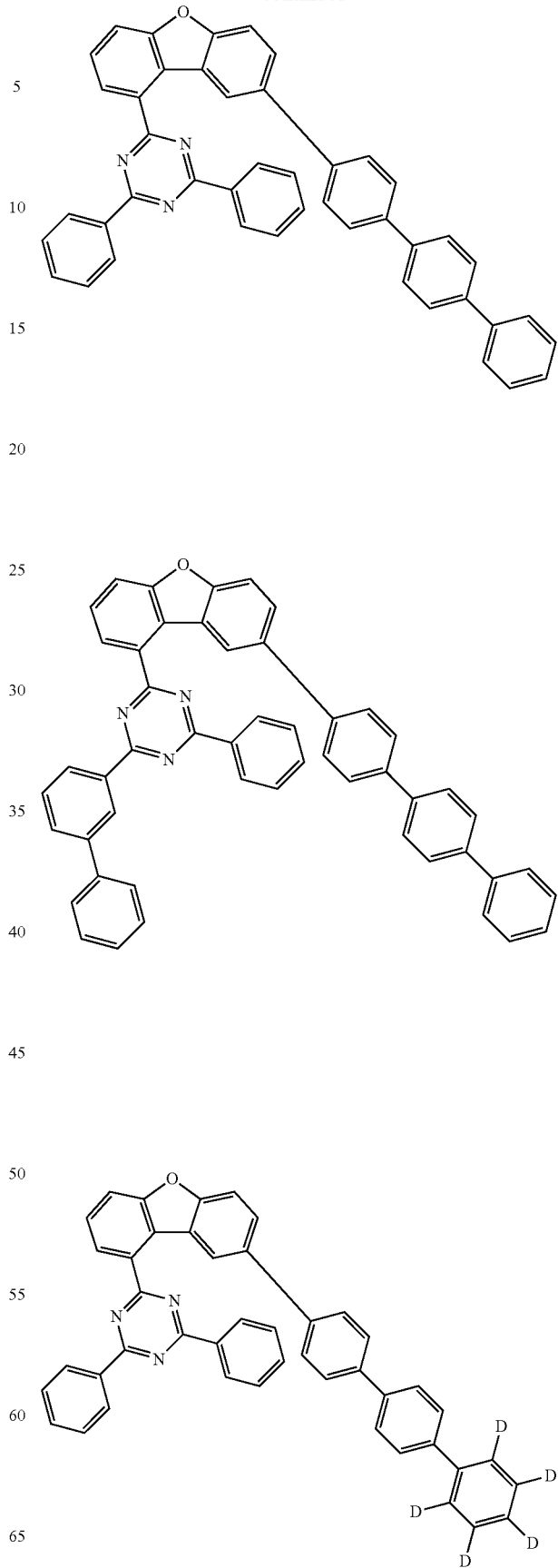

29
-continued
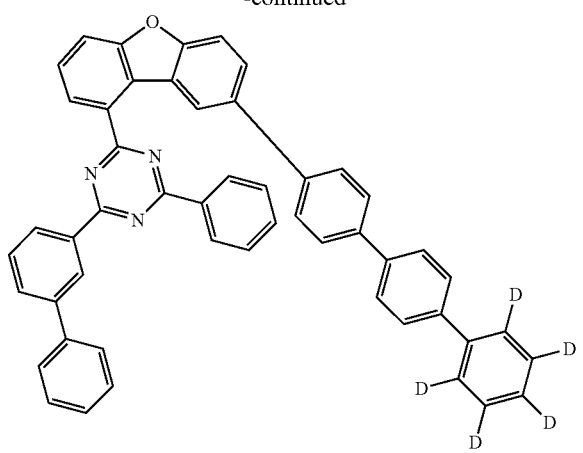
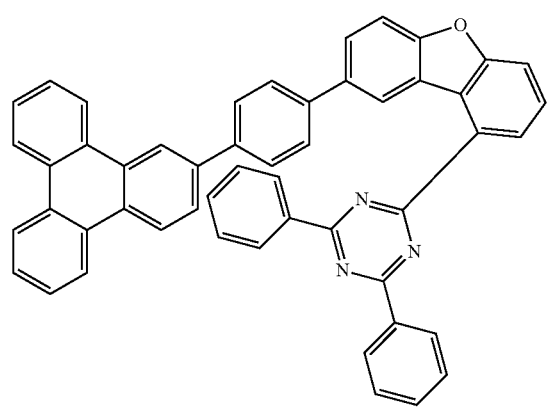
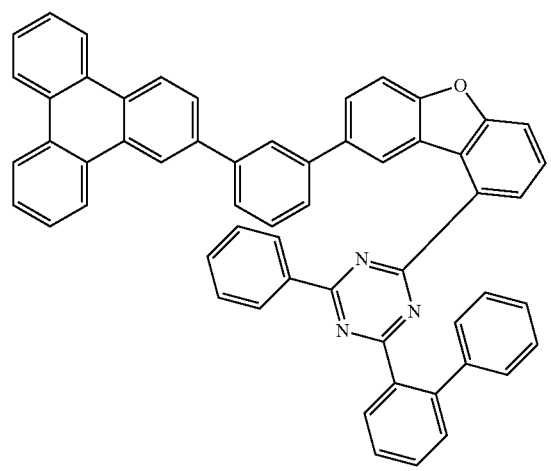
30
-continued
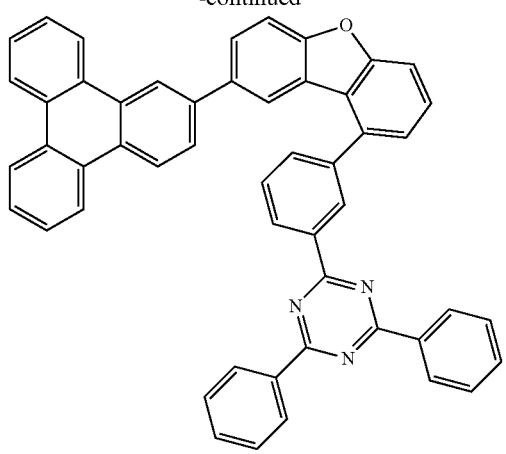
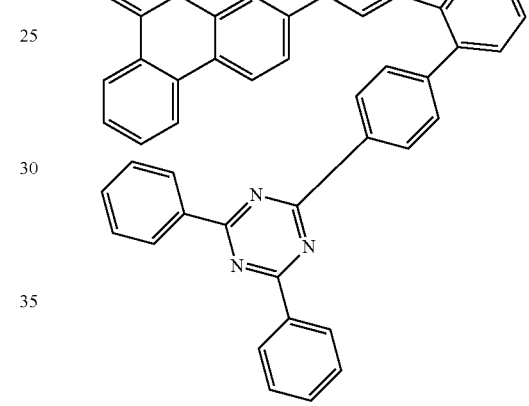
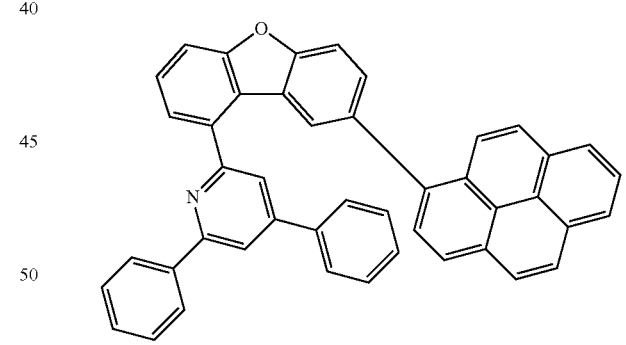
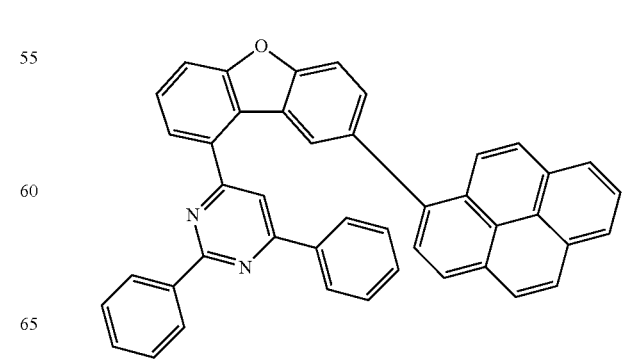

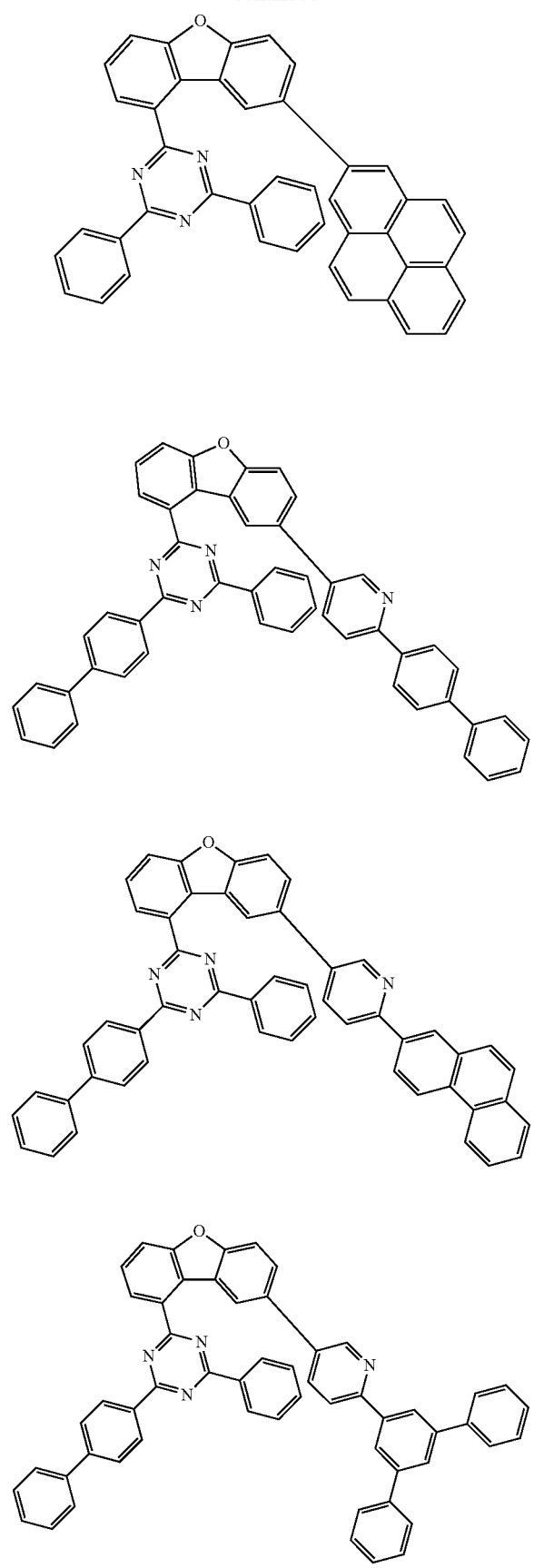
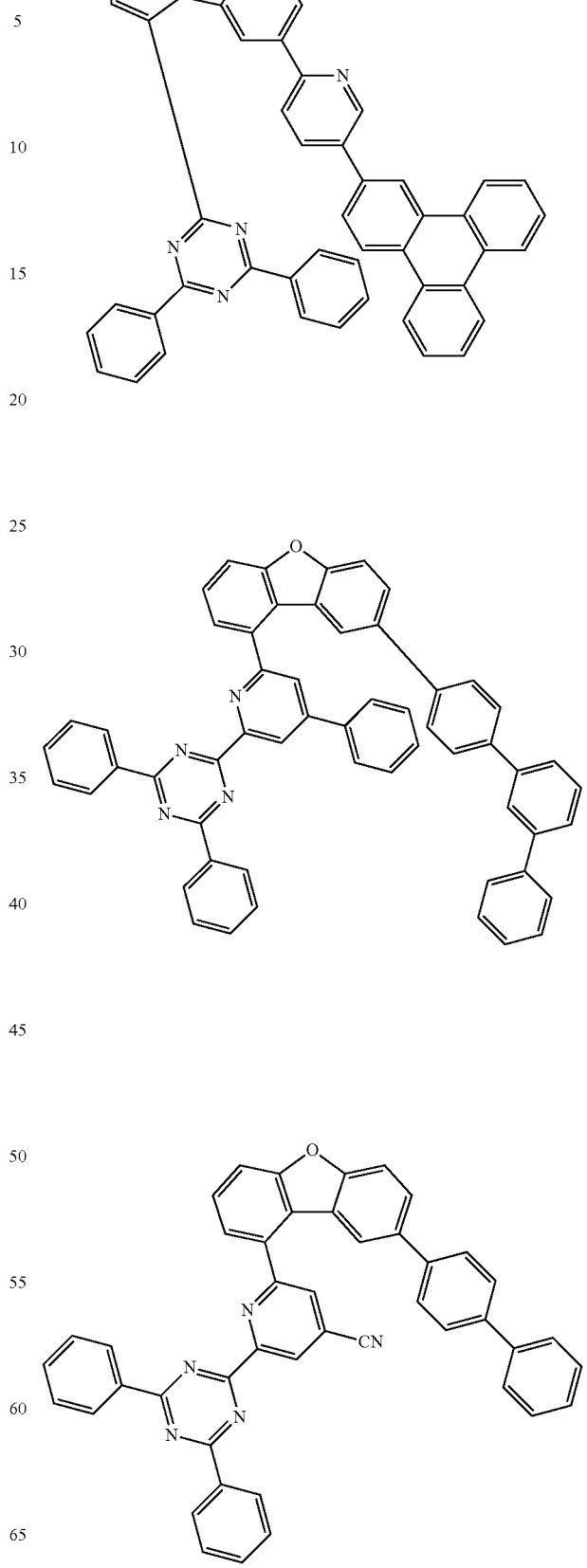

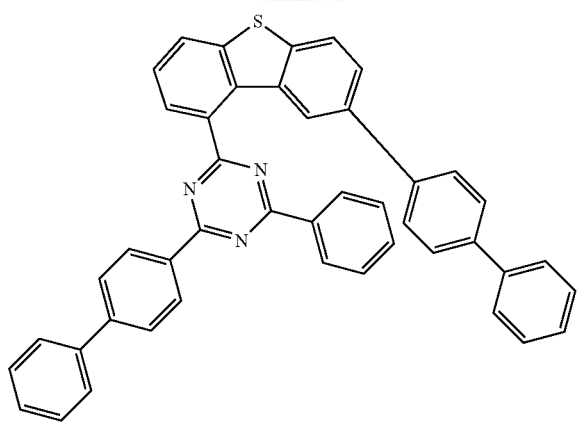
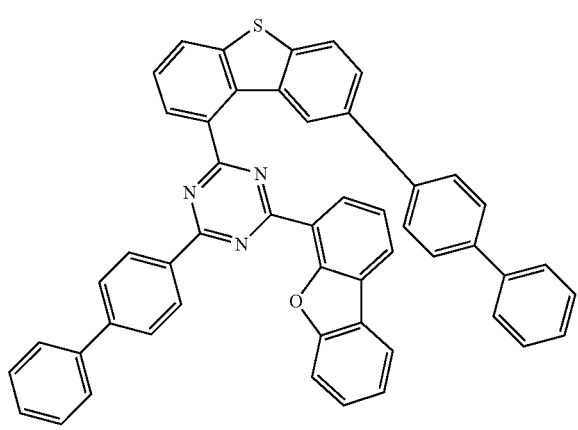
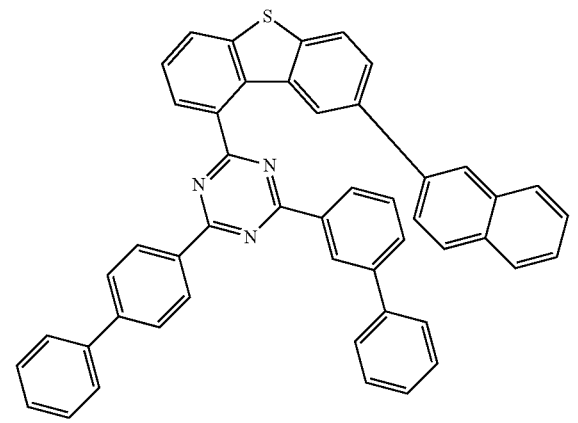
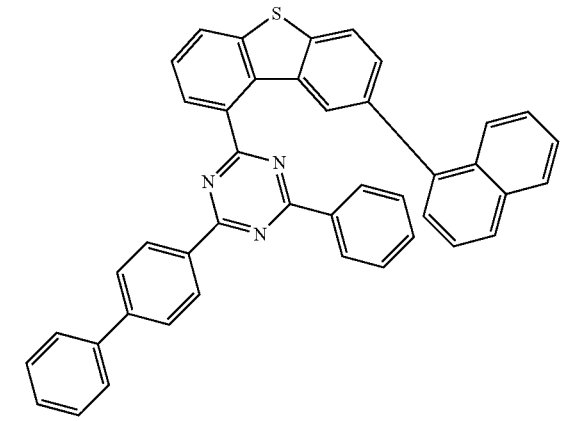
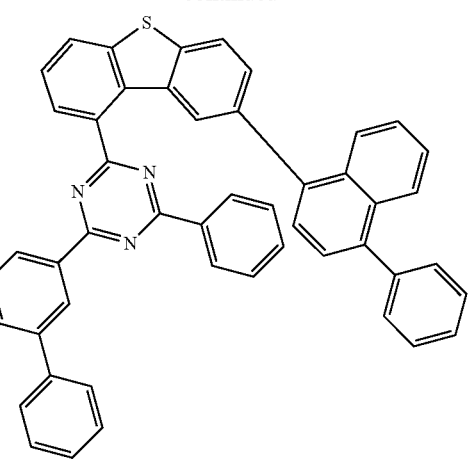
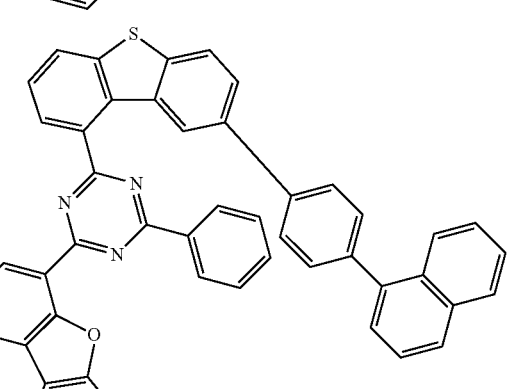
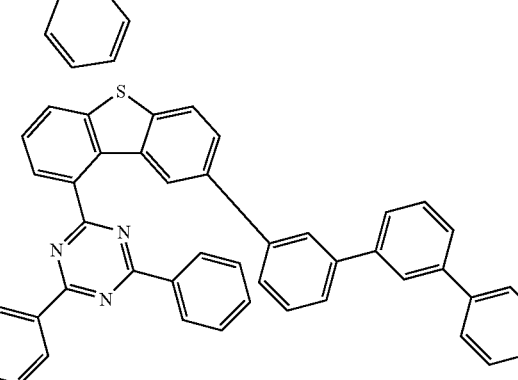
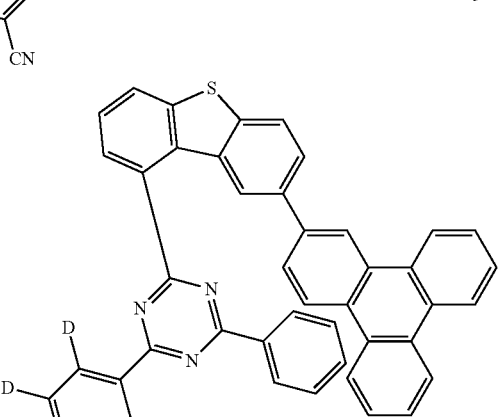

35
-continued
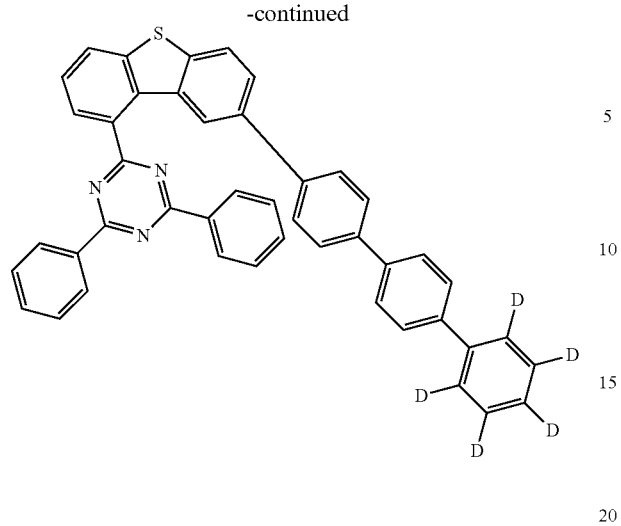
36
-continued
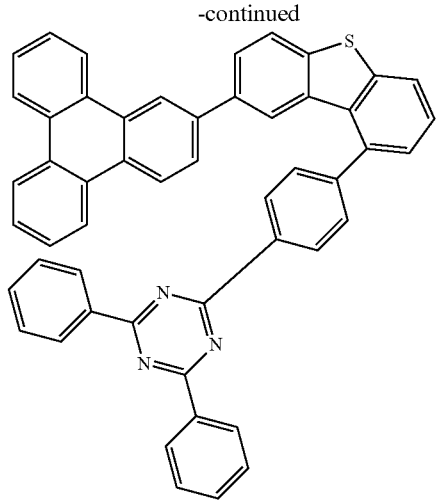
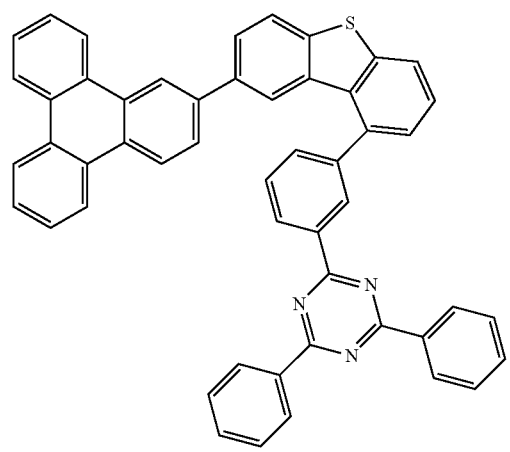
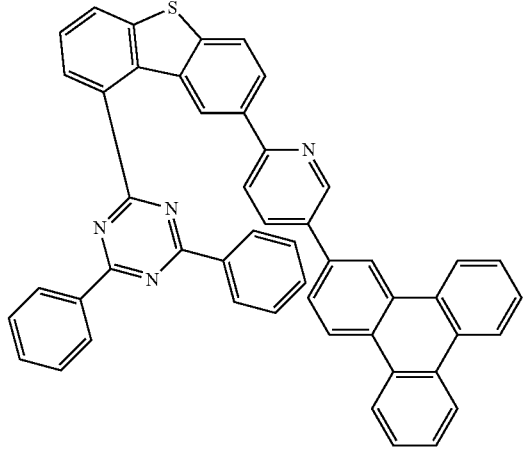

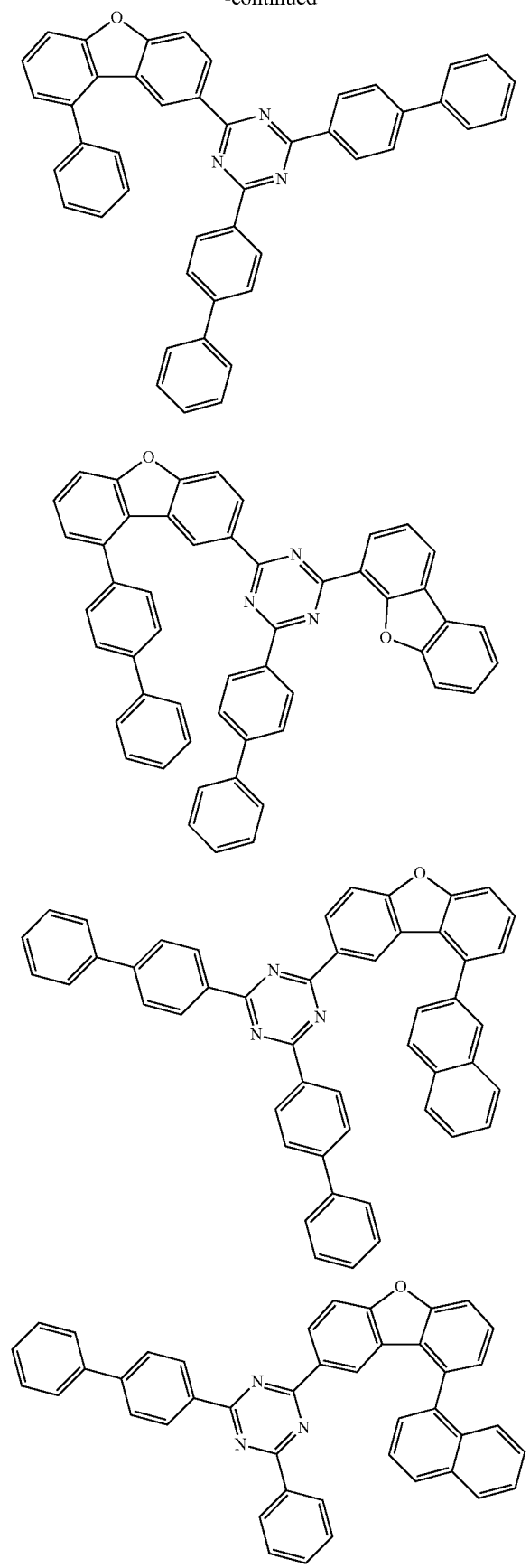
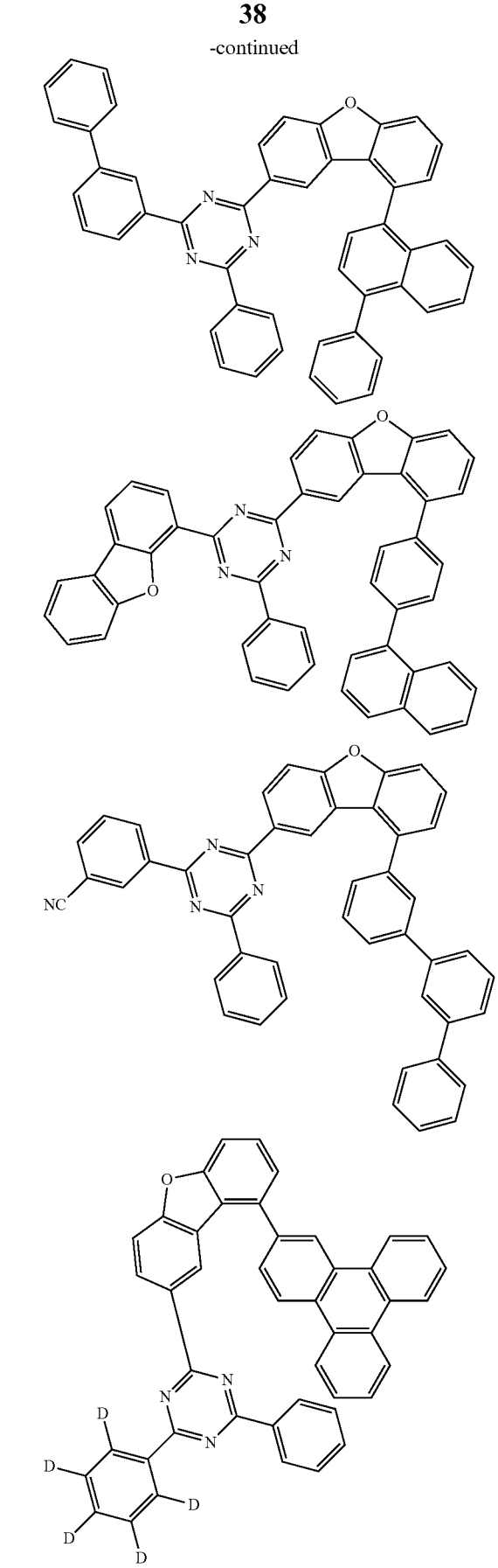

39
-continued
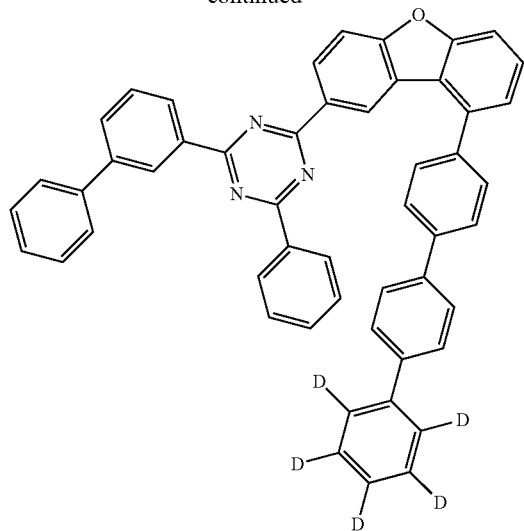
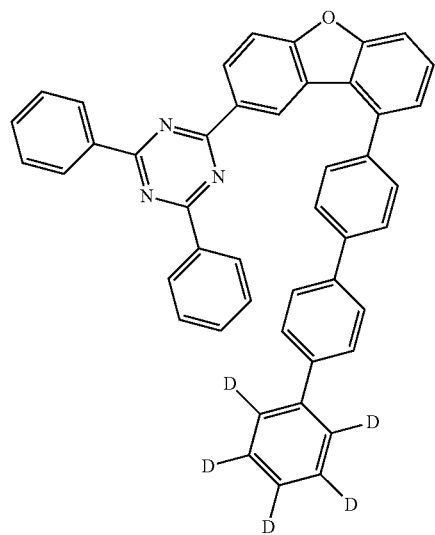 [SMILES: [2H]c1c([2H])c([2H])c(-c2ccc(-c3ccc(-c4cccc5oc6ccc(-c7nc(-c8ccccc8)nc(-c8ccccc8)n7)cc6c45)cc3)cc2)c([2H])c1[2H]]
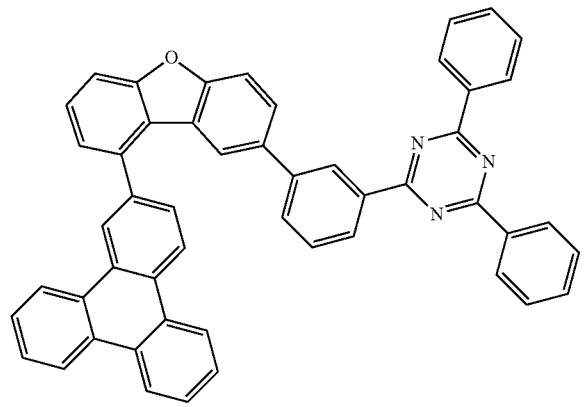
40
-continued
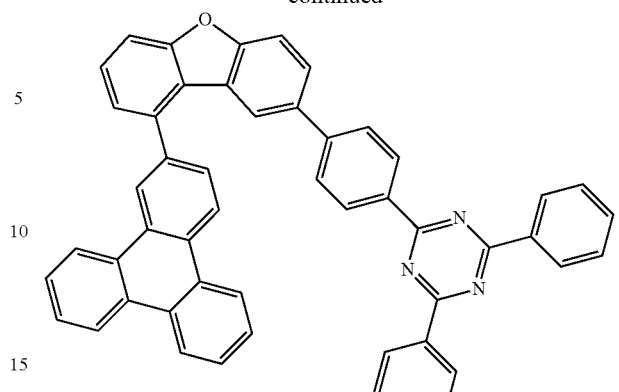
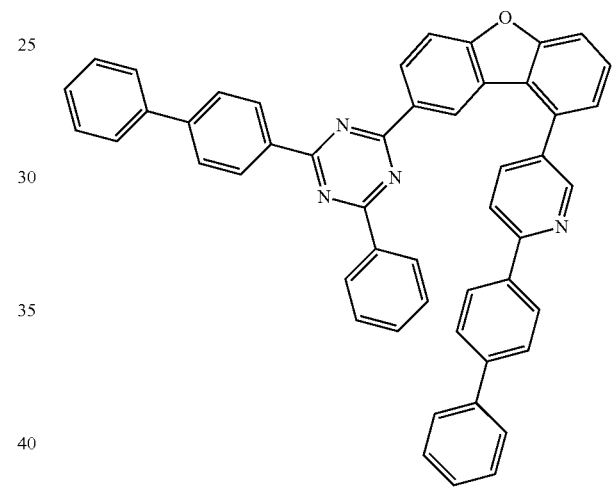
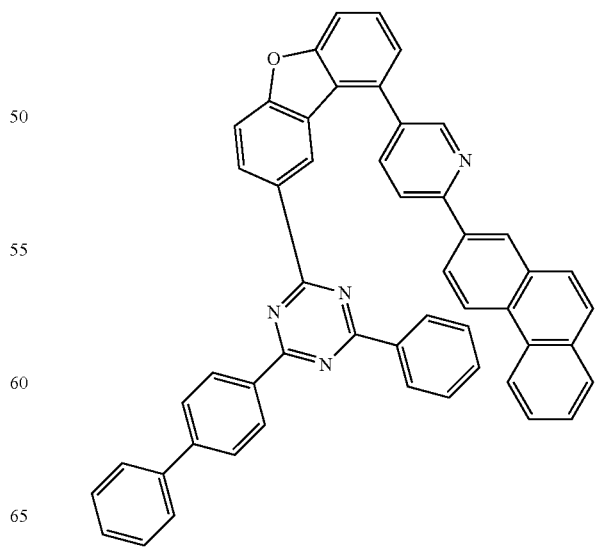

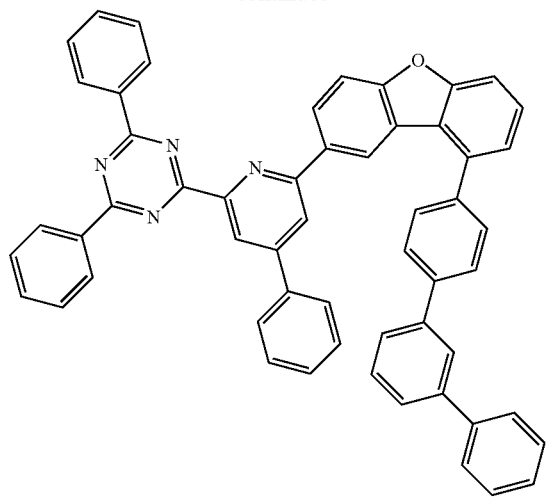
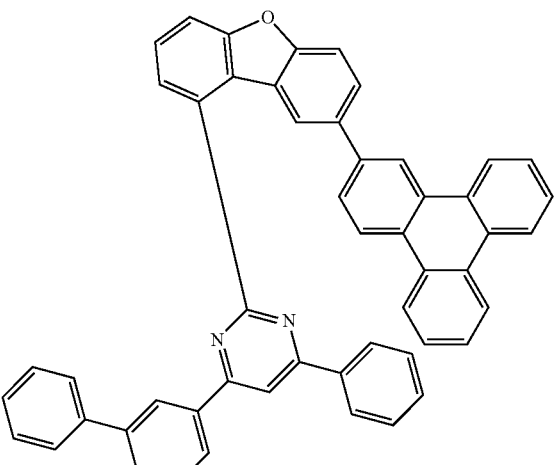
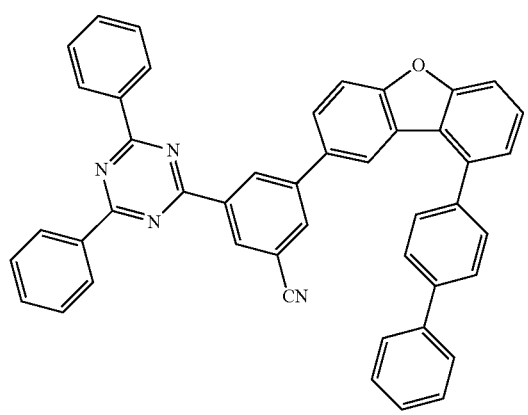
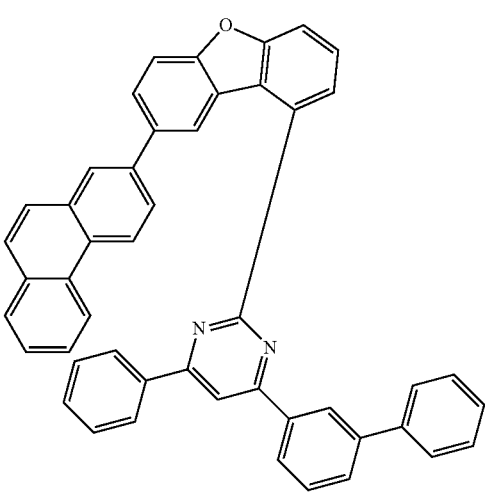
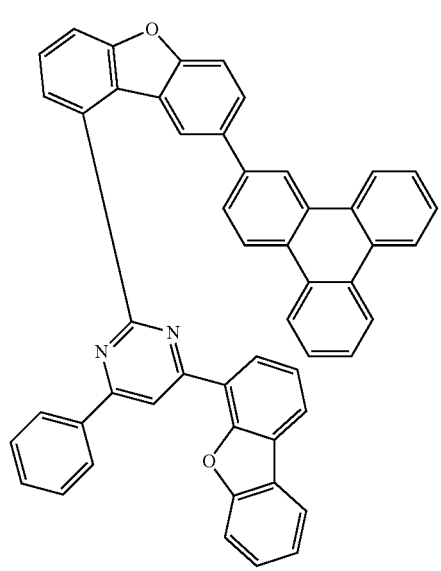
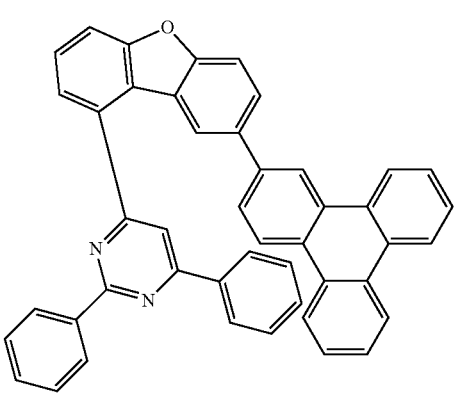

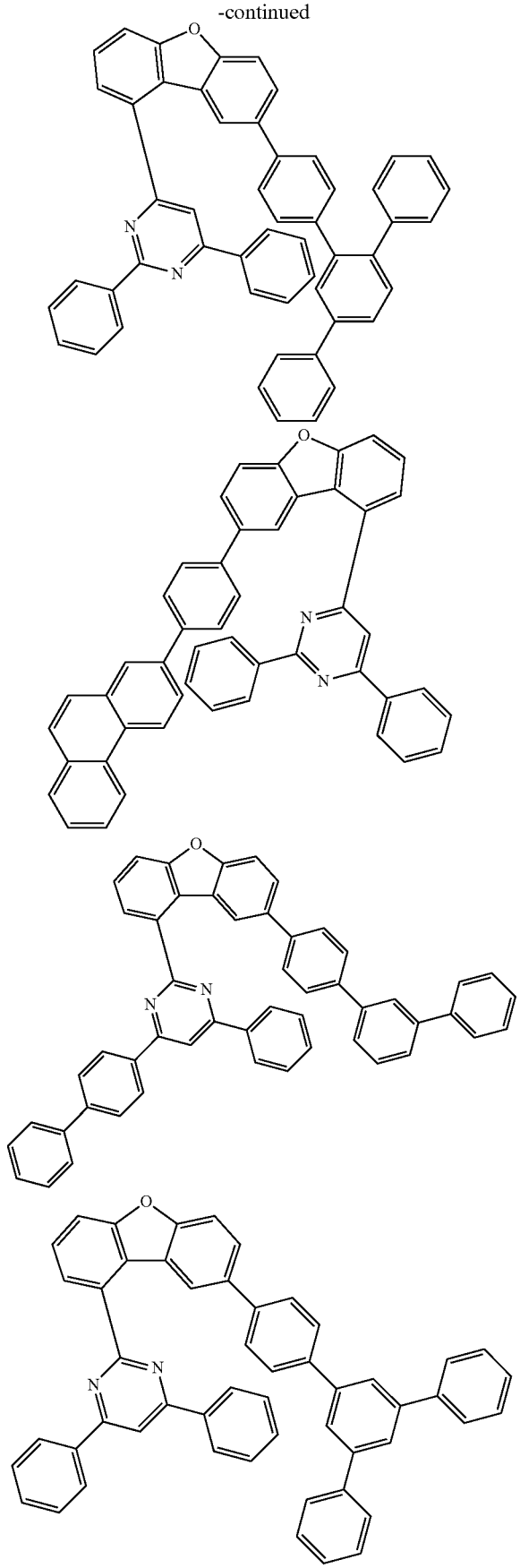
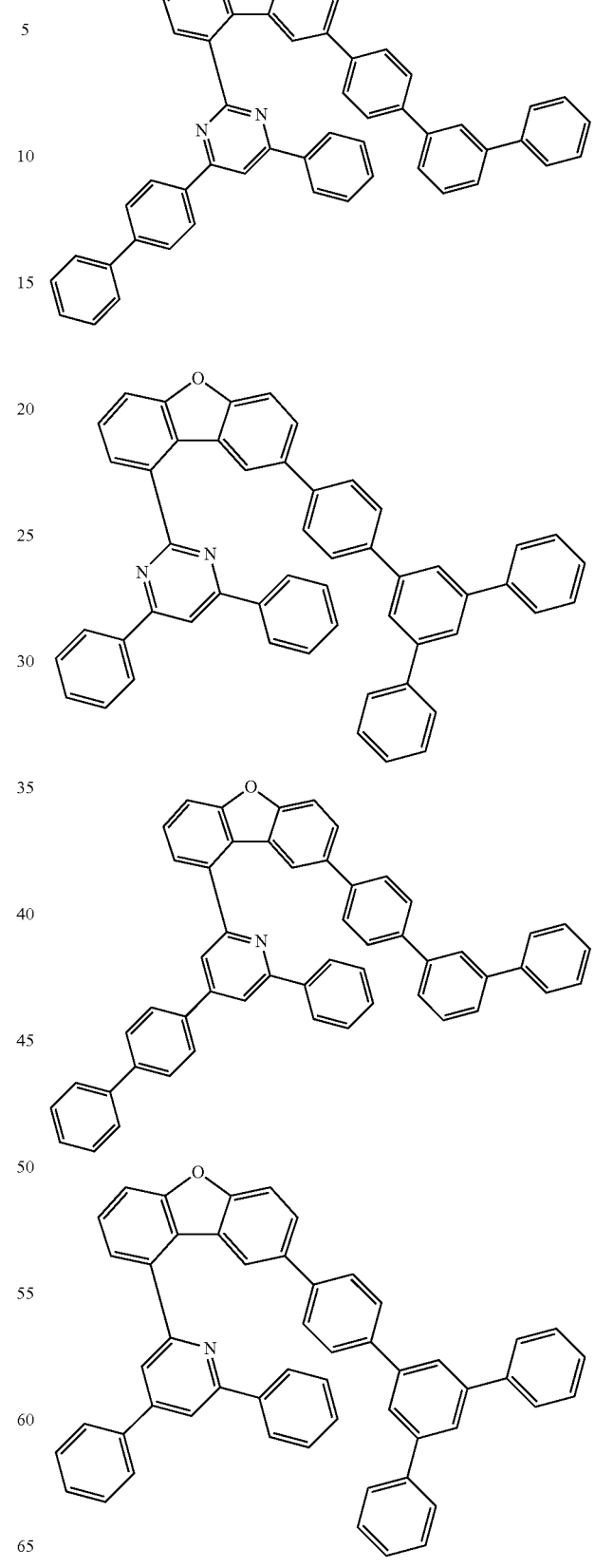

In addition, the compound represented by Chemical Formulae 1-1 and 1-2 can be prepared, for example, in the same manner as shown in the following Reaction Schemes 1-1 and 1-2:

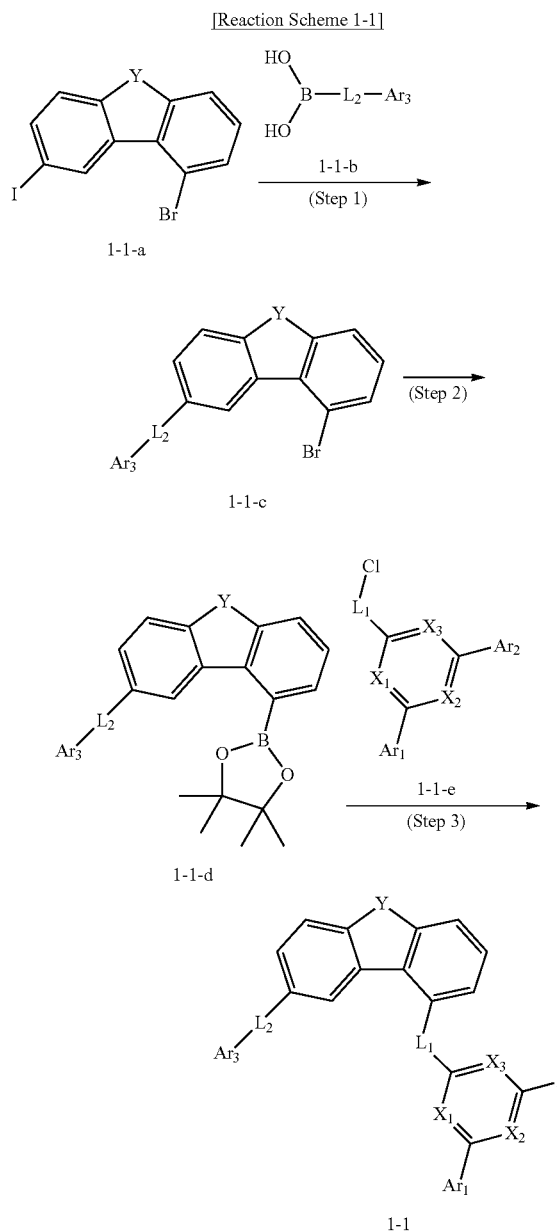

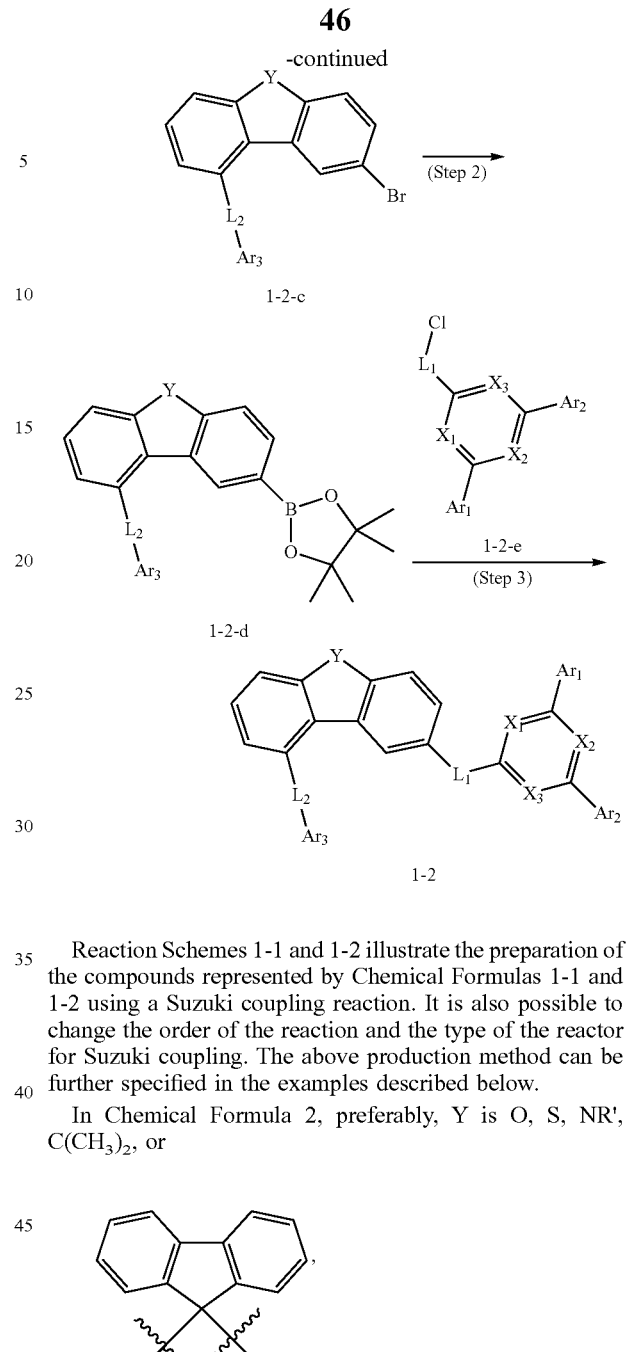

Reaction Schemes 1-1 and 1-2 illustrate the preparation of the compounds represented by Chemical Formulas 1-1 and 1-2 using a Suzuki coupling reaction. It is also possible to change the order of the reaction and the type of the reactor for Suzuki coupling. The above production method can be further specified in the examples described below.

In Chemical Formula 2, preferably, Y is O, S, NR', $C(CH_3)_2$, or

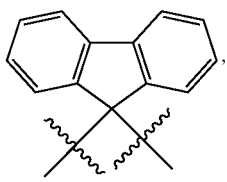

wherein R' is phenyl, phenyl substituted with cyano, biphenylyl, triphenylenyl, cyclohexyl, dimethylfluorenyl, or dibenzofuranyl.

Preferably, L' and L" are each independently a single bond, or phenylene.

Preferably, $R'_1$ is phenyl, phenyl substituted with tert-butyl, biphenylene, triphenylenyl, phenanthrenyl, terphenyl, pyridinyl, carbazolyl substituted with phenyl, dimethylfluorenyl, or dibenzothiophenyl.

Preferably, $R'_2$ and $R'_3$ are each independently hydrogen; tert-butyl; cyano; phenyl; phenyl substituted with cyano; or pyridinyl.

Representative examples of the compound represented by Chemical Formula 2 are as follows:

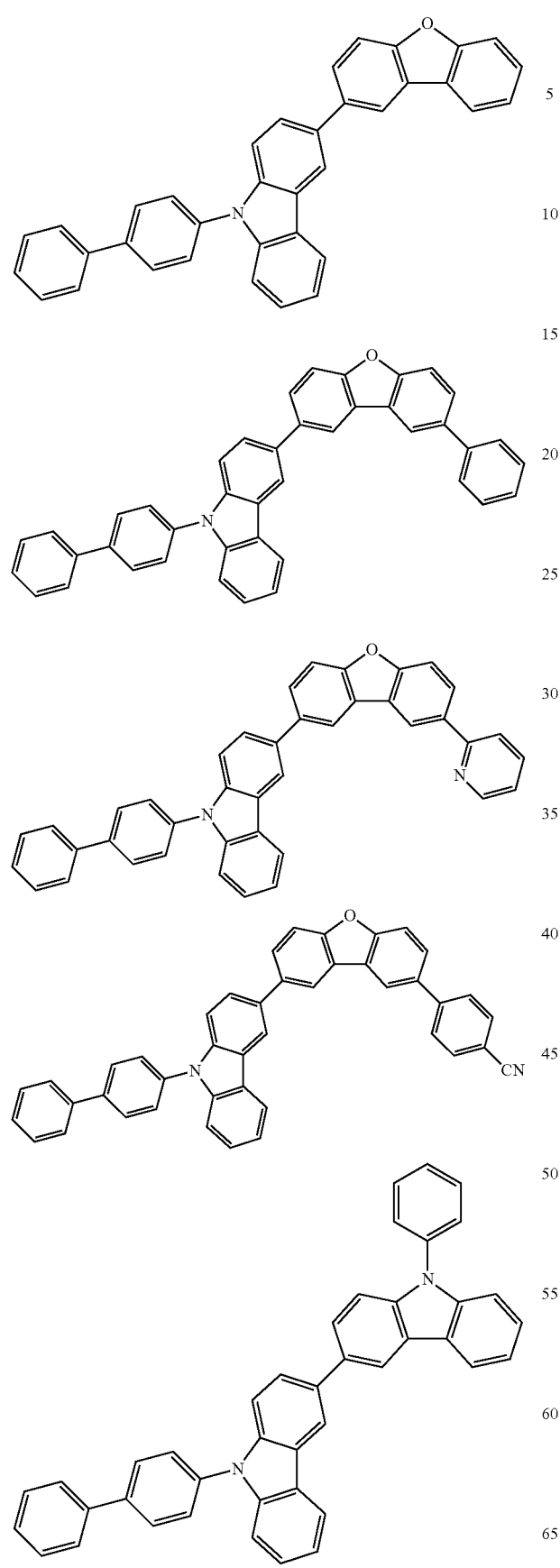
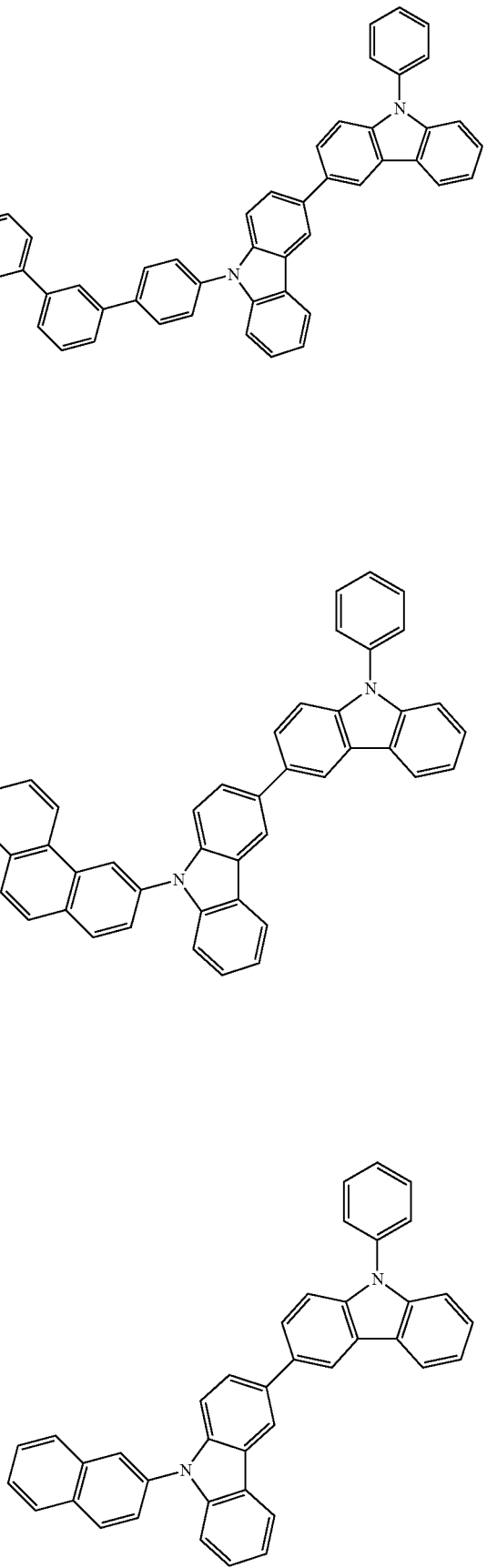

-continued
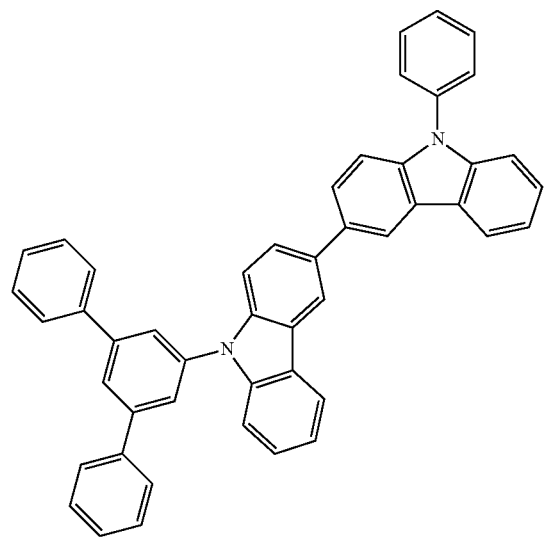
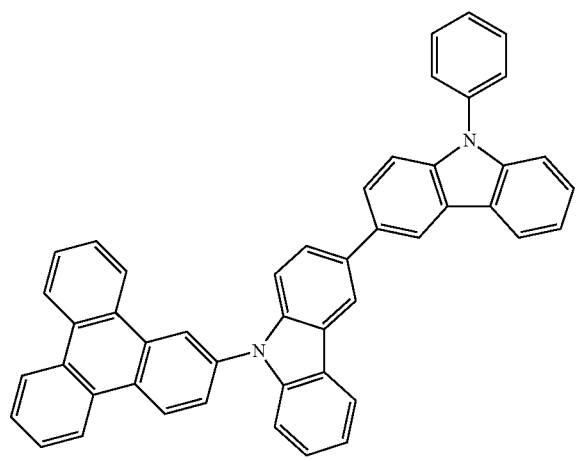 [SMILES: c1ccc(-c2ccc(-n3c4ccccc4c4cc(-c5ccc6c(c5)c5cccc7c8ccccc8n6c75)ccc43)cc2)cc1]
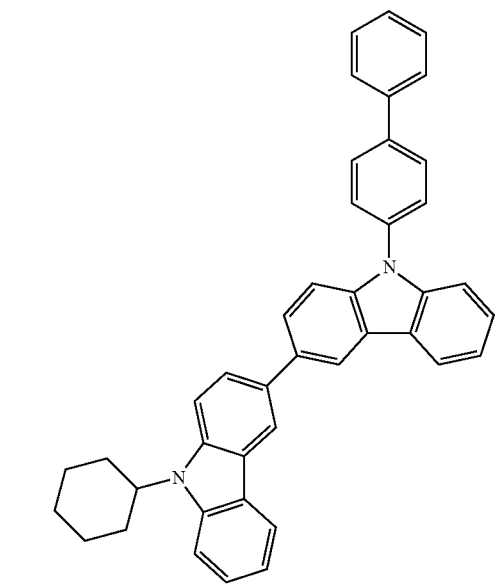
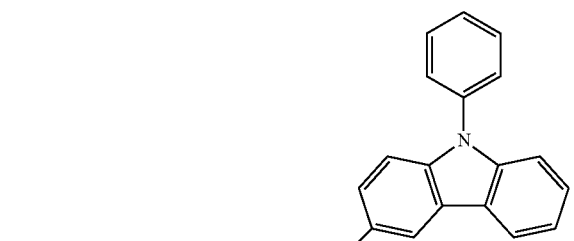
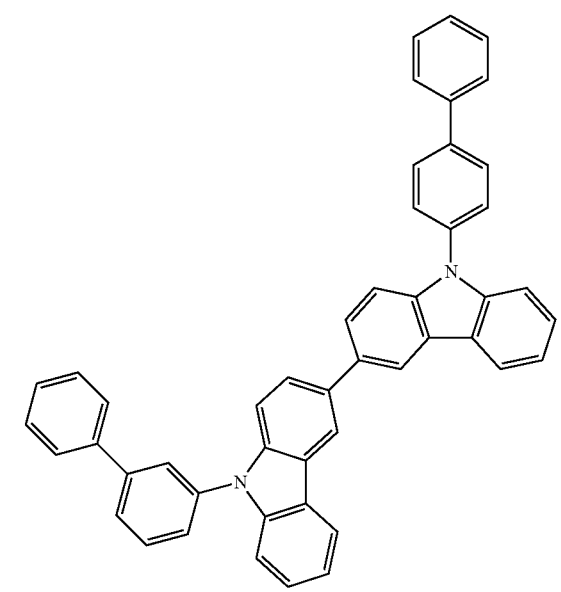

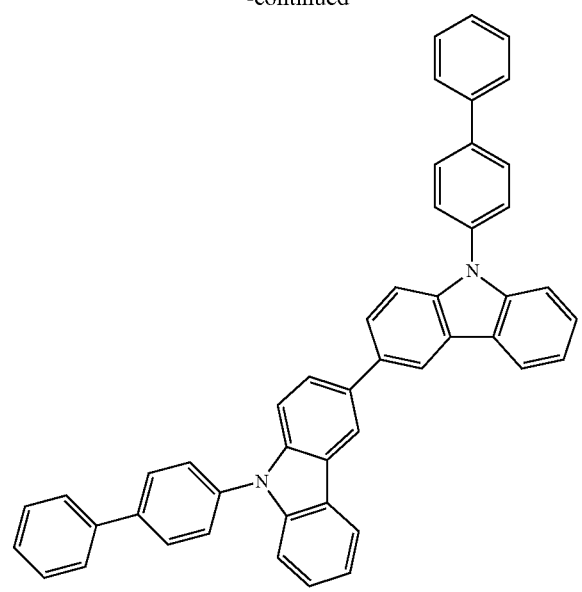
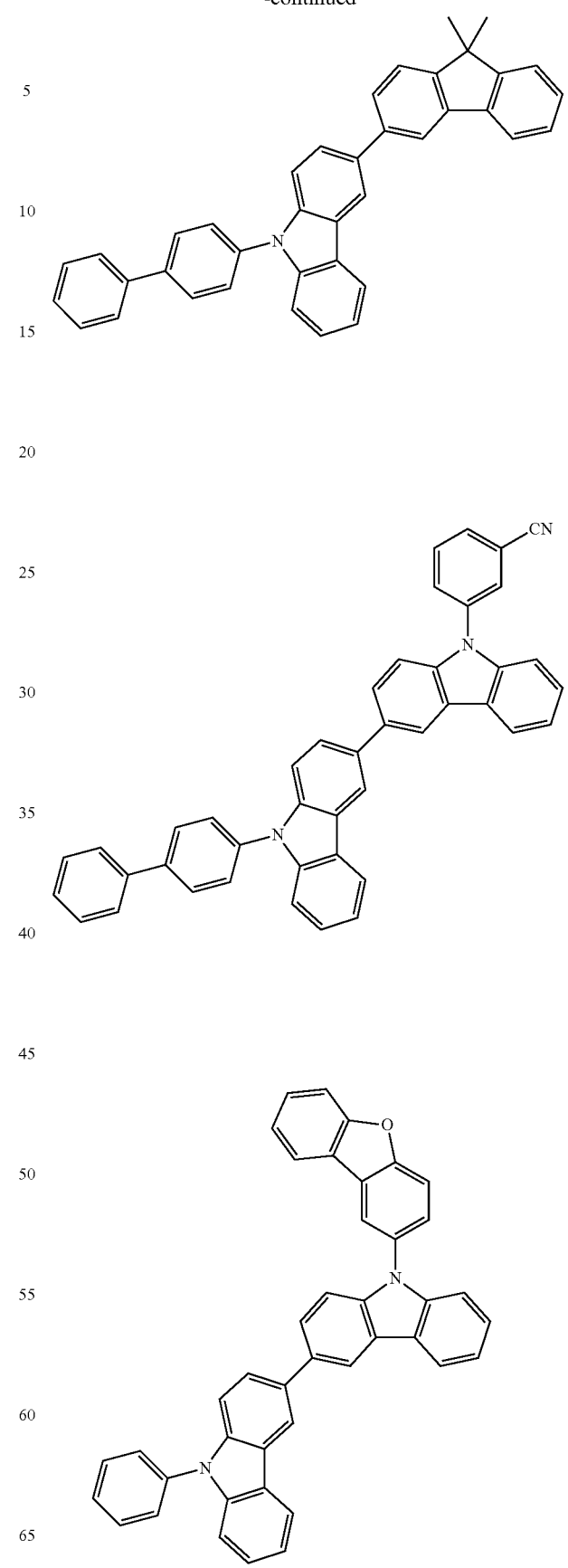

53
-continued
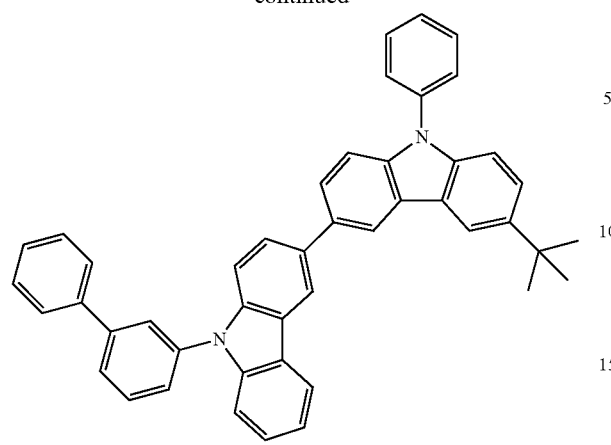
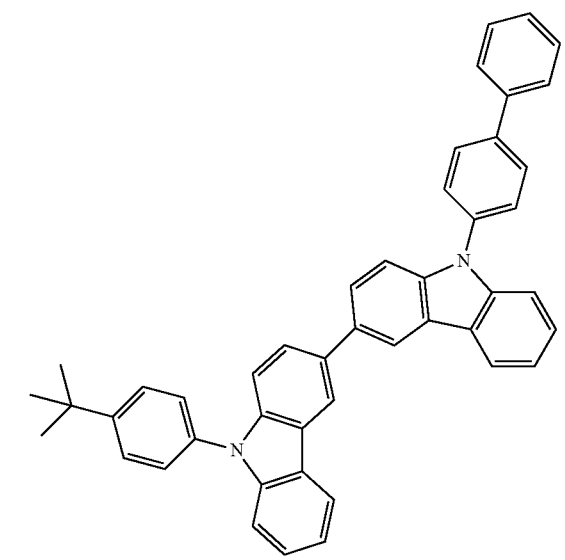
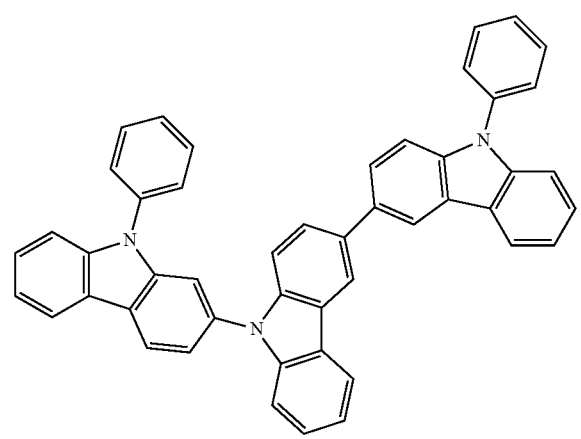
54
-continued
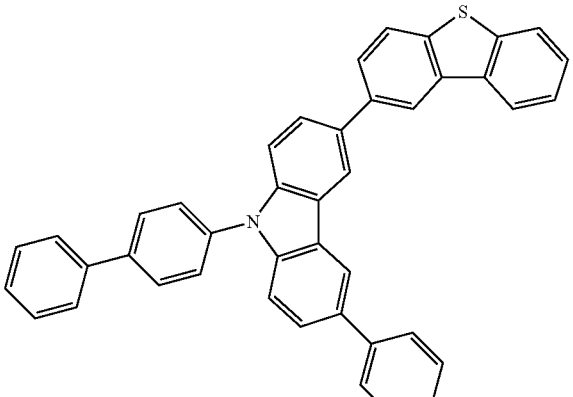
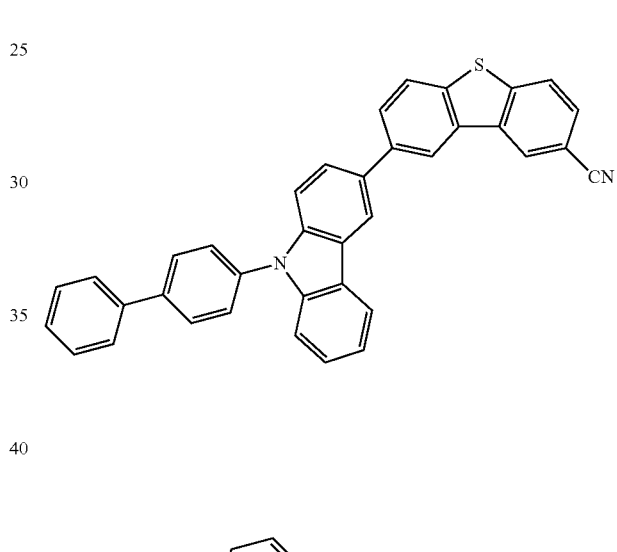
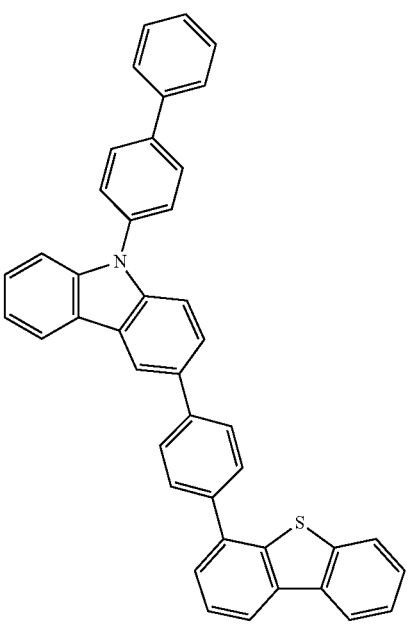

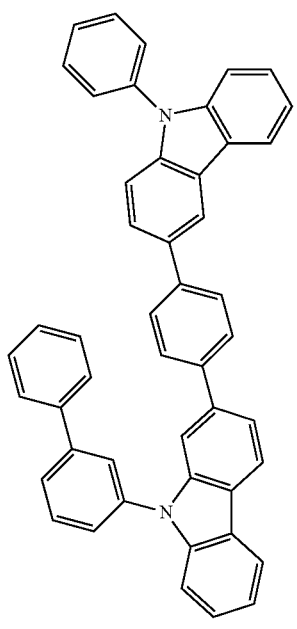
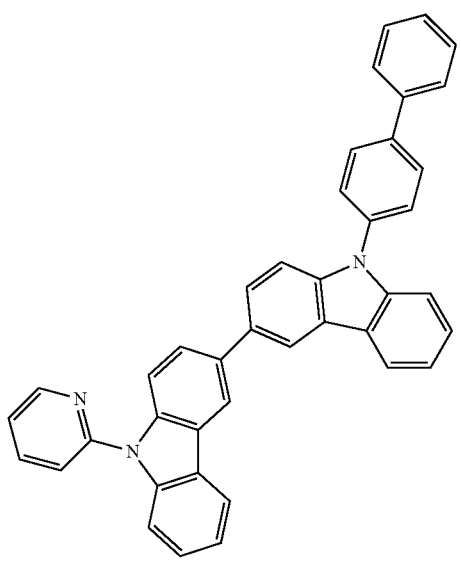 [SMILES: c1ccc(-c2ccc(-n3c4ccccc4c4cc(-c5ccc6c(c5)c5ccccc5n6-c5ccccn5)ccc43)cc2)cc1]
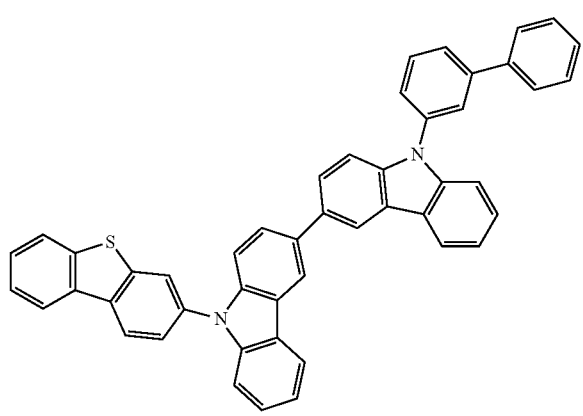
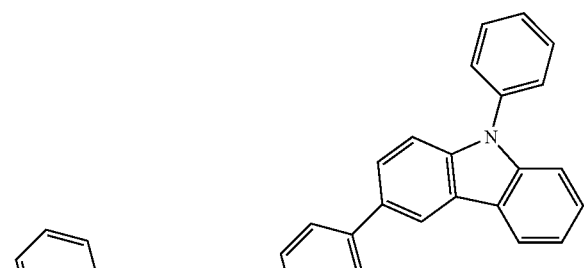
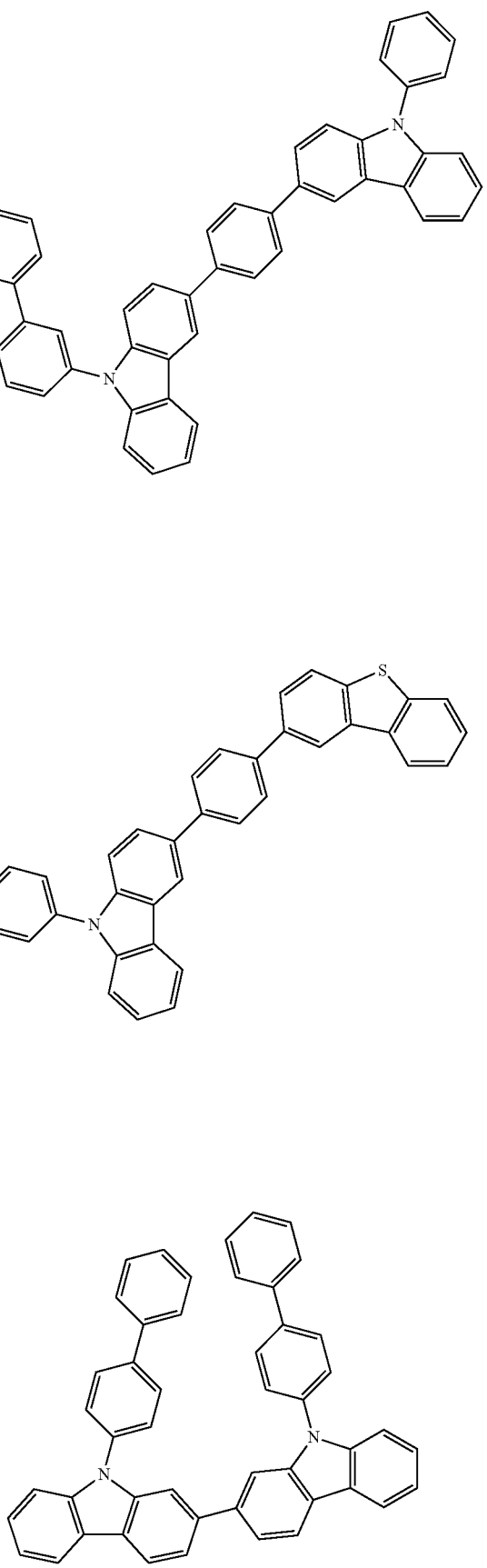

57
-continued
58
-continued
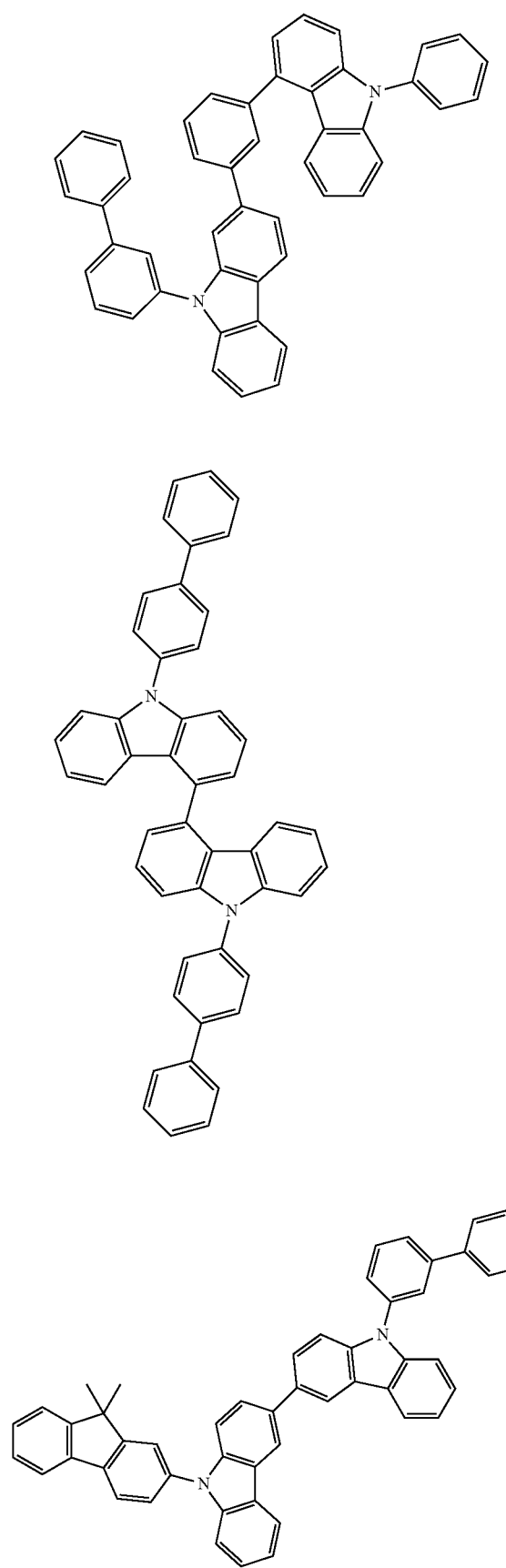
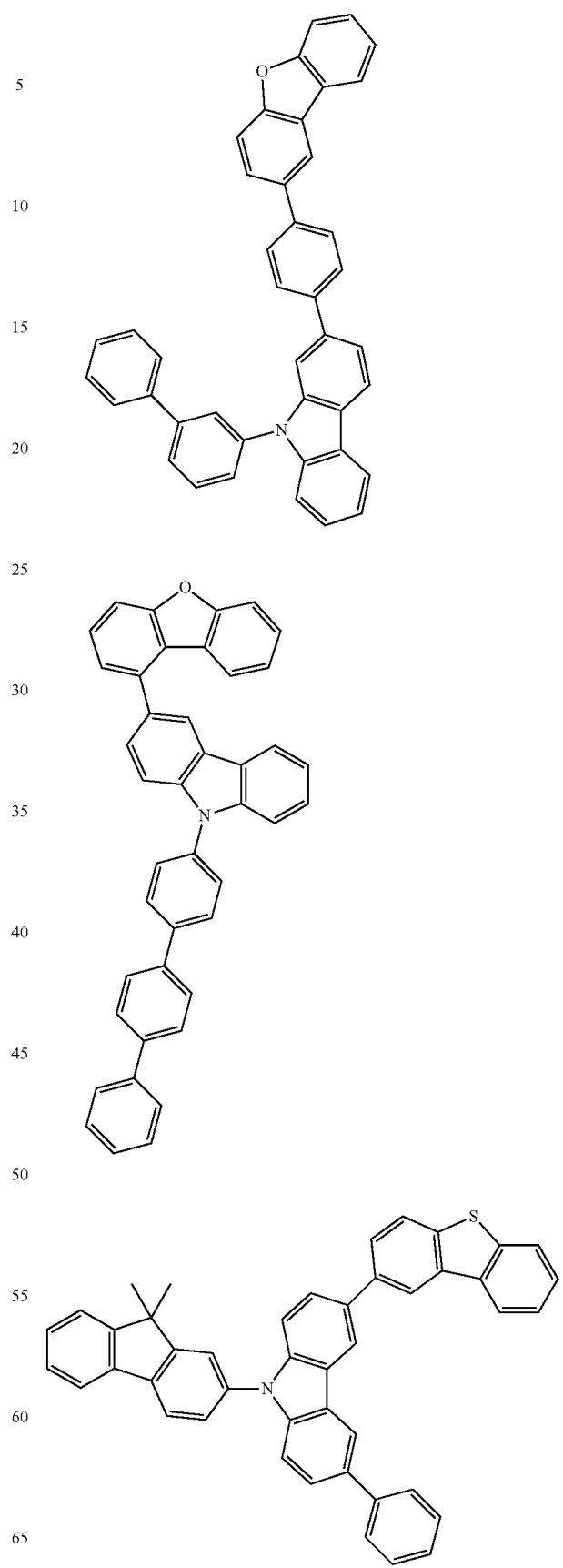

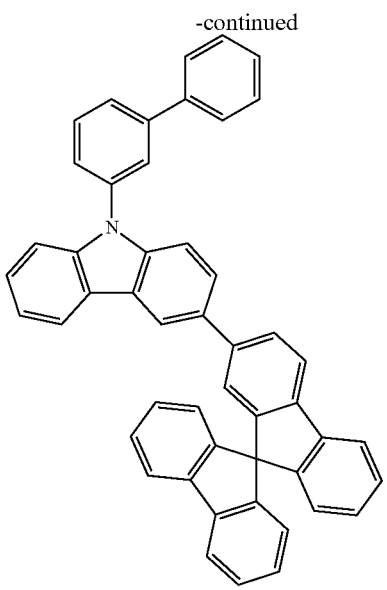

In addition, the compound represented by Chemical Formula 2 can be prepared, for example, in the same manner as shown in the following Reaction Scheme 2:

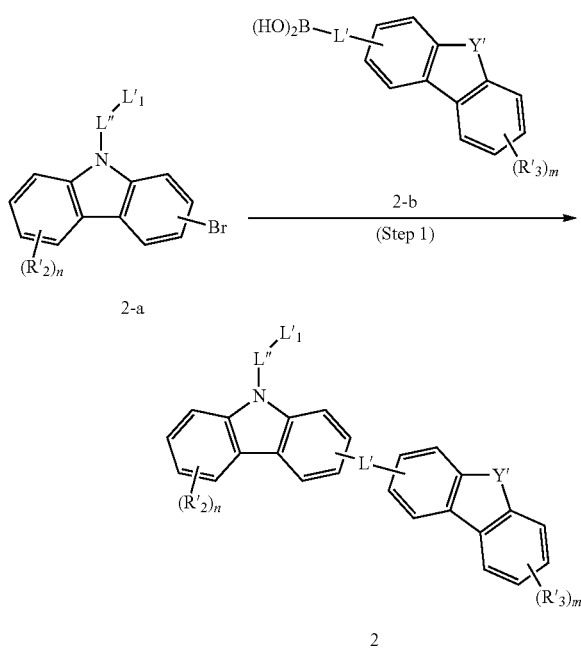

Reaction Scheme 2 illustrates the preparation of the compound represented by Chemical Formula 2 using a Suzuki coupling reaction, and it is also possible to change the type of the reactor for Suzuki coupling. The above production method can be further specified in examples described below.

Preferably, the weight ratio of the first host compound to the second host compound is from 1:99 to 99:1.

In addition, the light emitting layer may include a dopant material in addition to the host compound. The dopant material is not particularly limited as long as it is used for an organic light emitting device, and examples of the dopant material include an aromatic amine derivative, a styrylamine compound, a boron complex, a fluoranthene compound, a metal complex, and the like.

Specifically, the aromatic amine derivative is a condensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

Other Layers

Further, the organic light emitting device according to the present invention may include a hole injection layer, a hole transport layer, an electron transfer layer, and/or an electron transporting layer, if necessary.

The hole injection material layer is a layer injecting the holes from the electrode, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, polythiophene-based conductive polymer, and the like, but are not limited thereto.

The hole transport layer is a layer that can receive the holes from the anode or the hole injection layer and transport the holes to the light emitting layer, and a material having large mobility to the holes is suitable. Specific examples thereof include an arylamine-based organic material, a conductive polymer, a block copolymer in which a conjugate portion and a non-conjugate portion are present together, and the like, but are not limited thereto.

The electron transport layer is a layer receiving the electrons from the electron injection layer or the cathode and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

Organic Light Emitting Device

The organic light emitting device according to the present invention can be prepared in the same manner as in the material known in the art, except that a first host and a second host are included in a light emitting layer.

For example, the organic light emitting device according to the present invention may be manufactured by sequentially laminating the cathode, the organic material layer and the anode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, the organic material layer, and an anode material on the substrate.

Further, the first host compound and the second compound may be formed as the light emitting layer by a vacuum deposition method as well as a solution coating method during the production of the organic light emitting device. Herein, the solution coating method means spin coating, dip coating, doctor blading, inkjet printing, screen printing, spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

The organic light emitting device according to the present invention may be a front side emission type, a back side emission type, or a double side emission type according to the used material.

Hereinafter, preferred examples of the present invention will be described in order to facilitate understanding of the present invention. However, the following examples are presented for illustrative purposes only, and the scope of the present invention is not limited thereto.

Preparation Example: Preparation of Intermediate Compound P-4

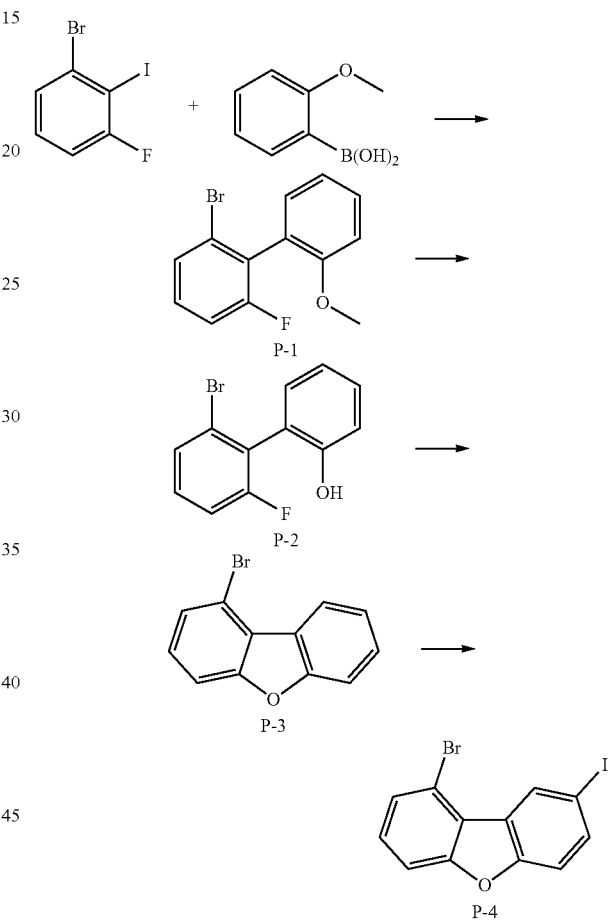

Step 1: Preparation of Compound P-1

1-Bromo-3-fluoro-2-iodobenzene (100 g, 333.5 mmol), 2-methoxyphenyl)boronic acid (50.6 g, 333.5 mmol) were dissolved in 800 mL of tetrahydrofuran (THF). Then, 2M sodium carbonate ($Na_2CO_3$) solution (500 mL) and tetrakis(triphenylphosphine)palladium(0) [$Pd(PPh_3)_4$] (7.7 g, 6.7 mmol) were added thereto, and the mixture was refluxed for 12 hours. After completion of the reaction, the mixture was cooled to room temperature, and then was extracted three times with water and toluene. The toluene layer was separated and dried with magnesium sulfate, and the filtrate was distilled under reduced pressure. The resulting mixture was recrystallized three times using chloroform and ethanol to obtain Compound P-1 (49.7 g, yield 53%).

MS: $[M+H]^+$ 281

Step 2: Preparation of Compound P-2

Compound P-1 (45 g, 158 mmol) was dissolved in dichloromethane (600 ml) and then cooled to 0° C. Boron tribromide (15.8 ml, 166.4 mmol) was slowly added dropwise thereto and then stirred for 12 hours. After completion of the reaction, the mixture was washed three times with water, dried with magnesium sulfate, and filtered. The filtrate was distilled under reduced pressure and purified by column chromatography to obtain Compound P-2 (40 g, yield 85%).

MS: [M+H]$^+$298

Step 3: Preparation of Compound P-3

Compound P-2 (33 g, 110 mmol) was added to 200 mL of dimethylformamide under a nitrogen atmosphere and stirred. Potassium carbonate (30.4 g, 220 mmol) was then added and refluxed. After 2 hours, the temperature was lowered to room temperature and filtered. The filtrate was extracted with chloroform and water, and then the organic layer was dried with magnesium sulfate. The mixture was distilled under reduced pressure, and the resulting mixture was recrystallized from chloroform and ethyl acetate to obtain Compound P-3 (20.3 g, yield 75%).

MS: [M+H]$^+$=247

Step 4: Preparation of Compound P-4

Iodine (2.06 g, 40 mmol) and iodic acid (3.13 g, 17.8 mmol) were added to the compound P-3 (20 g, 80 mmol) under a nitrogen atmosphere and a mixture of 80 mL of acetic acid and 20 mL of a sulfuric acid was added as a solvent to which 10 mL of water and 4 mL of chloroform were additionally added, and the mixture was stirred at 65° C. for 3 hours. After cooling, water was added to the mixture and the precipitated solid was filtered and washed three times with water. The filtrate thus obtained was recrystallized from toluene and hexane to obtain P-4 (20.0 g, yield 67%).

MS: [M+H]$^+$=374

Example 1-1: Preparation of Compound 1-1

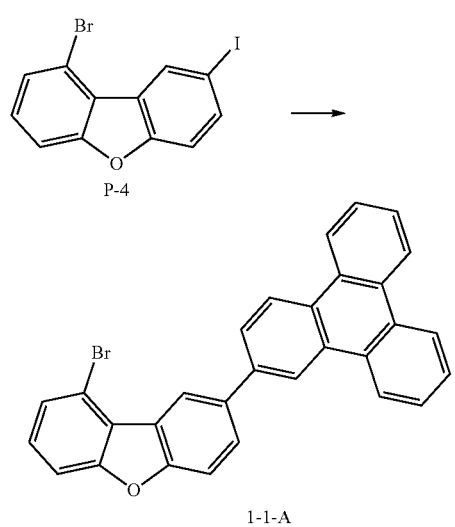

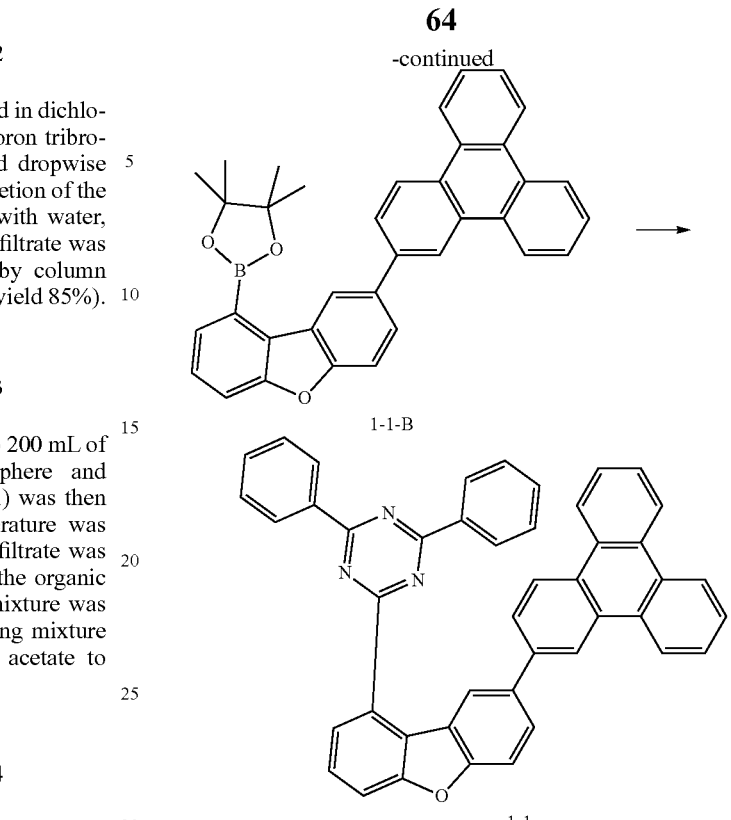

Step 1: Preparation of Compound 1-1-A

After Compound P-4 (20.0 g, 54 mmol) and triphenylene-2-ylboronic acid (15 g, 54 mmol) were dispersed in tetrahydrofuran (200 ml), 2M aqueous potassium carbonate solution (aq. K$_2$CO$_3$) (80 ml, 162 mmol) was added, tetrakis(triphenylphosphine)palladium [Pd(PPh$_3$)$_4$] (0.6 g, 1 mol %) was added, and then the mixture was stirred and refluxed for 5 hours. The temperature was lowered to room temperature and the resulting solid was filtered. The filtrated solid was recrystallized from chloroform and ethyl acetate, filtered and then dried to obtain Compound 1-1-A (20.7 g, yield 81%).

Step 2: Preparation of Compound 1-1-B

Compound 1-1-A (20.0 g, 42.2 mol), bis(pinacolato)diborone (14.5 g, 50.6 mmol) and potassium acetate (8.5 g, 85 mmol) were added to 100 mL of 1,4-dioxane, and 0.73 g (1.3 mmol) of dibenzylidene acetone palladium and 0.71 g (1.3 mmol) of tricyclohexylphosphine were added under stirring and reflux, followed by stirring under reflux for 12 hours. After completion of the reaction, the mixture was cooled to room temperature and filtered through Celite. After concentrating the filtrate under reduced pressure, the residue was dissolved in chloroform and washed with water to separate the organic layer, followed by drying over anhydrous magnesium sulfate. This was distilled under reduced pressure and stirred with ethyl acetate and ethanol to prepare compound 1-1-B (19.3 g, yield 88%).

Step 3: Preparation of Compound 1-1

After Compound 1-1-B (20.0 g, 38 mol) and 2-chloro-4,6-diphenyl-1,3,5-triazine (10.3 g, 38 mmol) were dispersed in tetrahydrofuran (150 ml), 2M aqueous potassium carbonate solution (aq. K₂CO₃) (58 ml, 115 mmol) was added, tetrakis(triphenylphosphine)palladium [Pd(PPh₃)₄] (0.45 g, 1 mol %) was added, and then the mixture was stirred and refluxed for 6 hours. The temperature was lowered to room temperature and the resulting solid was filtered. The filtrated solid was recrystallized from chloroform and ethyl acetate, filtered and then dried to obtain Compound 1-1 (17.5 g, yield 73%).

MS: [M+H]⁺=626

Example 1-2: Preparation of Compound 1-2

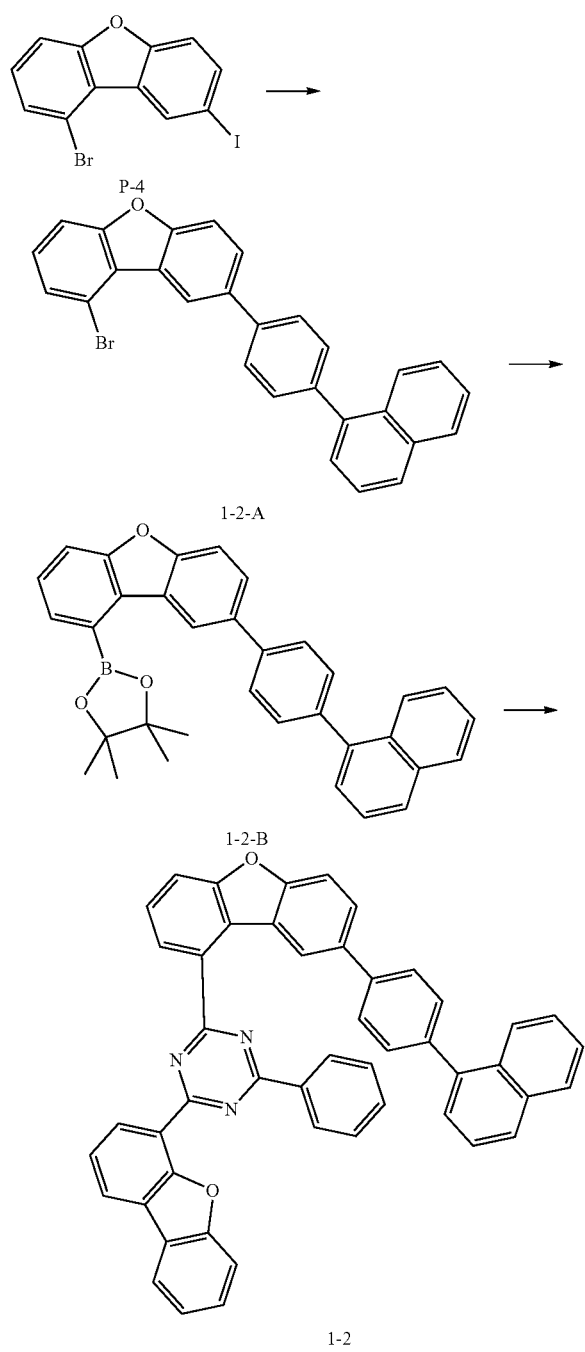

Step 1: Preparation of Compound 1-2-A

After Compound P-4 (20 g, 54 mmol) and (4-(naphthalen-1-yl)phenyl)boronic acid (13.3 g, 54 mmol) were dispersed in tetrahydrofuran (200 mL), 2M aqueous potassium carbonate solution (aq. K₂CO₃) (80 ml, 160 mmol) was added, tetrakis(triphenylphosphine)palladium [Pd(PPh₃)₄] (0.6 g, 1 mol %) was added, and then the mixture was stirred and refluxed for 6 hours. The temperature was lowered to room temperature and the resulting solid was filtered. The filtrated solid was recrystallized from chloroform and ethyl acetate, filtered and then dried to obtain Compound 1-2-A (17.0 g, yield 82%).

Step 2: Preparation of Compound 1-2-B

Compound 1-2-A (20.0 g, 44.5 mol), bis(pinacolato)diborone (15.3 g, 53.4 mmol) and potassium acetate (8.7 g, 89 mmol) were added to 200 mL of 1,4-dioxane, and 0.8 g (1.3 mmol) of dibenzylidene acetone palladium and 0.8 g (1.3 mmol) of tricyclohexylphosphine were added under stirring and reflux, followed by stirring under reflux for 12 hours. After completion of the reaction, the mixture was cooled to room temperature and filtered through Celite. After concentrating the filtrate under reduced pressure, the residue was dissolved in chloroform and washed with water to separate the organic layer, followed by drying over anhydrous magnesium sulfate. This was distilled under reduced pressure and stirred with ethyl acetate and ethanol to prepare compound 1-2-B (19 g, yield 86%).

Step 3: Preparation of Compound 1-2

After Compound 1-2-B (20 g, 40 mmol) and 2-chloro-4-(dibenzo[b,d]furan-4-yl)-6-phenyl-1,3,5-triazine (14.4 g, 40 mmol) were dispersed in tetrahydrofuran (180 mL), 2M aqueous potassium carbonate solution (aq. K₂CO₃) (60 ml, 121 mmol) was added, tetrakis(triphenylphosphine)palladium [Pd(PPh₃)₄] (0.47 g, 1 mol %) was added, and then the mixture was stirred and refluxed for 6 hours. The temperature was lowered to room temperature and the resulting solid was filtered. The filtrated solid was recrystallized from chloroform and ethyl acetate, filtered and then dried to obtain Compound 1-2 (19.5 g, yield 70%).

MS: [M+H]⁺=692

Example 1-3: Preparation of Compound 1-3

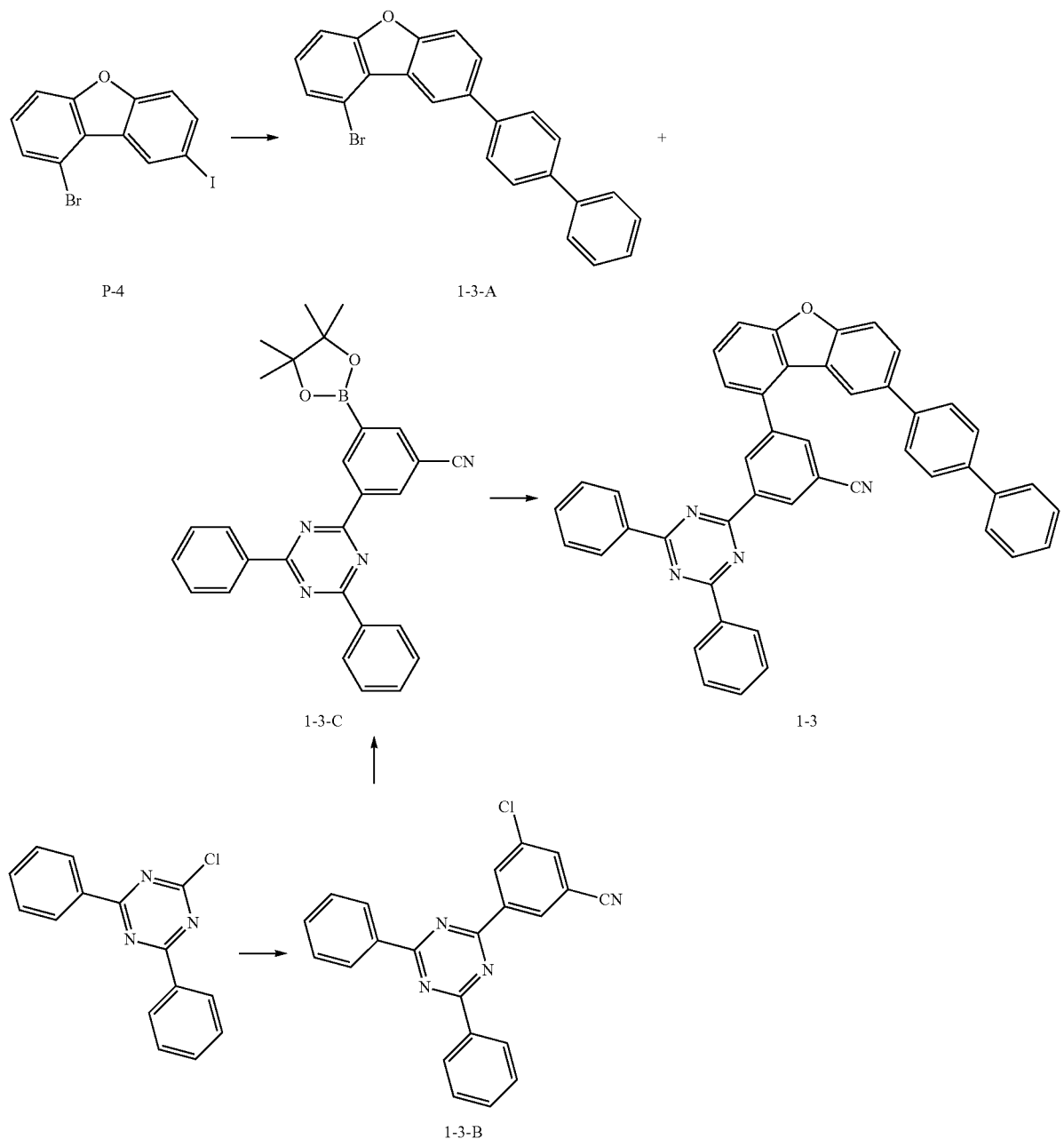

Step 1: Preparation of Compound 1-3-A

Compound 1-3-A (18.4 g, yield 86%) was prepared in the same manner as in the preparation example of Compound 1-A-1, using Compound P-4 (20 g, 54 mmol) and [1,1'-biphenyl]-4-ylboronic acid.

Step 2: Preparation of Compound 1-3-B

After 2-chloro-4,6-diphenyl-1,3,5-triazine (30 g, 112 mmol) and (3-chloro-5-cyanophenyl)boronic acid (20 g, 112 mmol) were dissolved in tetrahydrofuran (480 mL), 2M aqueous potassium carbonate solution (aq. $K_2CO_3$) (160 ml, 336 mmol) was added, tetrakis(triphenylphosphine)palladium [$Pd(PPh_3)_4$] (1.2 g, 1 mol %) was added, and then the mixture was stirred and refluxed for 5 hours. The temperature was lowered to room temperature and the aqueous layer was removed. The mixture was concentrated under reduced pressure. Ethanol and ethyl acetate were added and stirred, followed by filtration. The resulting solid was washed with water and ethanol and then dried to produce Compound 1-3-B (32.0 g, yield 91%).

Step 3: Preparation of Compound 1-3-C

Compound 1-3-B (19 g, yield 76) was prepared in the same manner as in the preparation example of Compound 1-A-2 using Compound 1-3-B (20 g, 54 mmol).

Step 4: Preparation of Compound 1-3

Compound 1-3 (20.7 g, yield 73) was prepared in the same manner as in the preparation example of Compound 1-1 using Compound 1-3-A (17.3 g, 43 mmol) and Compound 1-3-C (20 g, 43 mmol).

MS: [M+H]$^+$=653

Example 1-4: Preparation of Compound 1-4

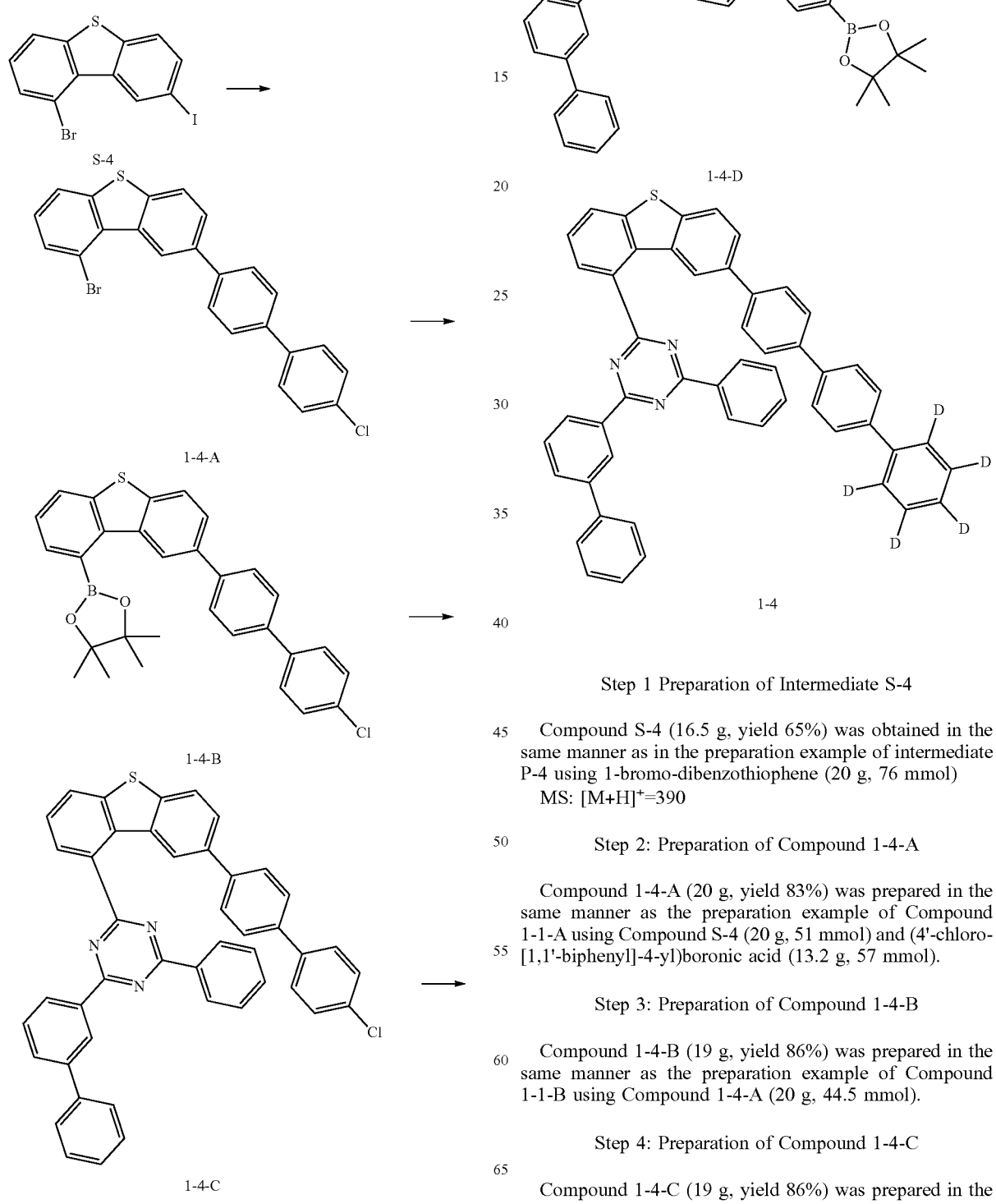

Step 1 Preparation of Intermediate S-4

Compound S-4 (16.5 g, yield 65%) was obtained in the same manner as in the preparation example of intermediate P-4 using 1-bromo-dibenzothiophene (20 g, 76 mmol)

MS: [M+H]$^+$=390

Step 2: Preparation of Compound 1-4-A

Compound 1-4-A (20 g, yield 83%) was prepared in the same manner as the preparation example of Compound 1-1-A using Compound S-4 (20 g, 51 mmol) and (4'-chloro-[1,1'-biphenyl]-4-yl)boronic acid (13.2 g, 57 mmol).

Step 3: Preparation of Compound 1-4-B

Compound 1-4-B (19 g, yield 86%) was prepared in the same manner as the preparation example of Compound 1-1-B using Compound 1-4-A (20 g, 44.5 mmol).

Step 4: Preparation of Compound 1-4-C

Compound 1-4-C (19 g, yield 86%) was prepared in the same manner as the preparation example of Compound 1-1-C using Compound 1-4-B (20 g, 40.3 mmol) and 2-([1,1'-biphenyl-3-yl]-4-chloro-6-phenyl-1,3,5-triazine (13.8 g, 40.3 mmol).

Step 5: Preparation of Compound 1-4-D

Compound 1-4-D (16 g, yield 82%) was prepared by conducting the experiment in the same manner as in the preparation example of Compound 1-3-C using Compound 1-4-C (20 g, 30 mmol).

Step 6: Preparation of Compound 1-4

Compound 1-4 (13 g, yield 70%) was prepared by conducting the experiment in the same manner as in the preparation example of Compound 1-1-A using Compound 1-4-D (20 g, 26 mmol) and bromobenzene-d5 (5 g, 31 mmol).

MS: [M+H]$^+$=726

Example 1-5: Preparation of Compound 1-5

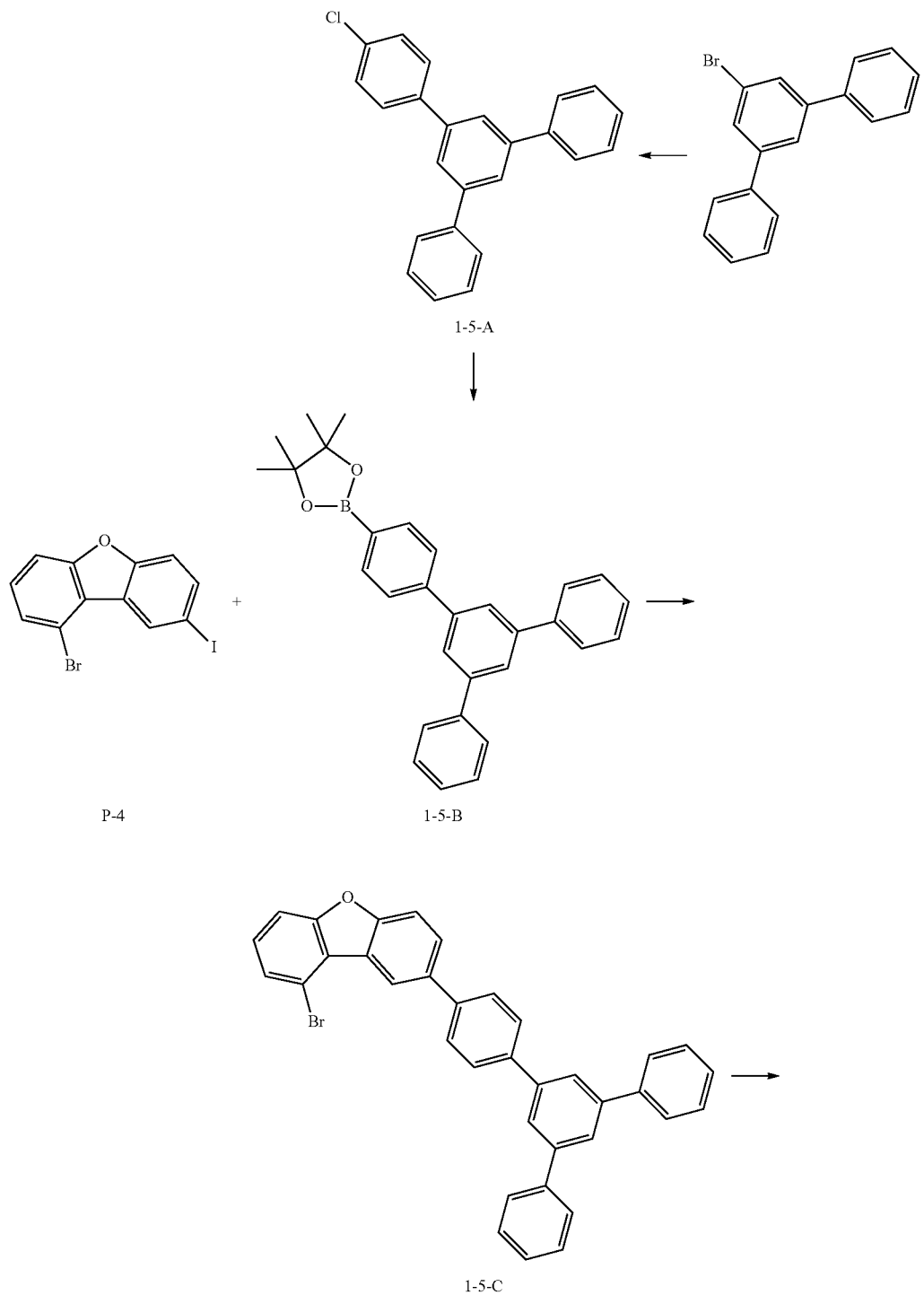

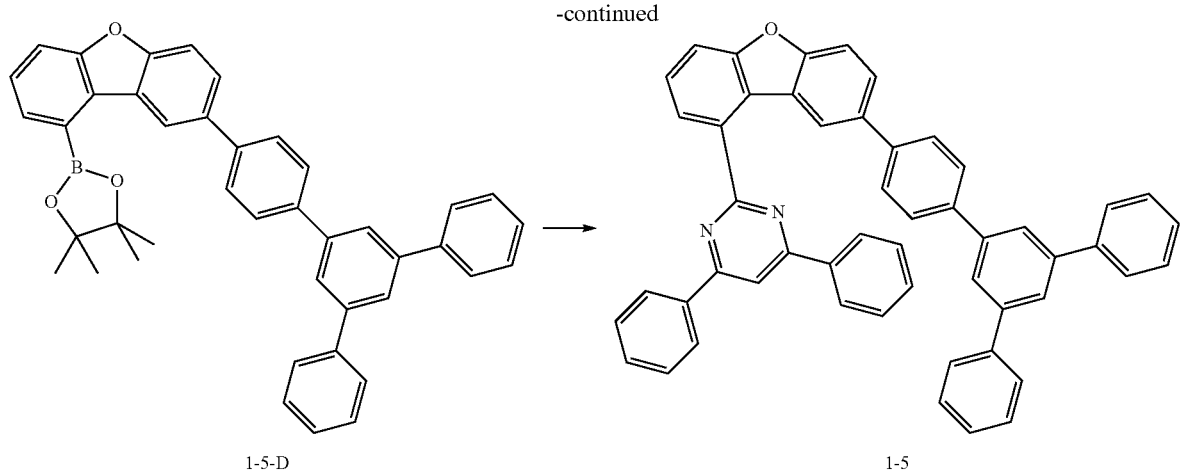

1-5-D 1-5

Step 1: Preparation of Compound 1-5-A

Compound 1-5-A (19 g, yield 86%) was obtained in the same manner as in the preparation example of Compound 1-1-A using 5'-bromo-1,1':3',1''-terphenyl (20 g, 65 mmol) and (4-chlorophenyl)boronic acid (12.1 g, 78 mmol).

Step 2: Preparation of Compound 1-5-B

Compound 1-5-B (21 g, yield 81%) was prepared in the same manner as in the preparation example of Compound 1-1-B using Compound 1-5-A (20 g, 59 mmol).

Step 3: Preparation of Compound 1-5-C

Compound 1-5-C (19.3 g, yield 76%) was prepared in the same manner as in the preparation example of Compound 1-1-A using Compound 1-5-B (20 g, 46 mmol) and Intermediate P-4 (17 g, 46 mmol).

Step 4: Preparation of Compound 1-5-D

Compound 1-5-D (11.5 g, yield 80%) was prepared in the same manner as in the preparation example of Compound 1-1-B using Compound 1-5-C (15 g, 27 mmol).

Step 5: Preparation of Compounds 1-5

Compound 1-5 (8.2 g, yield 77%) was prepared in the same manner as in the preparation example of Compound 1-1 using Compound 1-5-D (12 g, 20 mmol) and 2-chloro-4,6-diphenylpyrimidine (5.7 g, 20 mmol).

MS: $[M+H]^+=703$

Example 1-6: Preparation of Compound 1-6

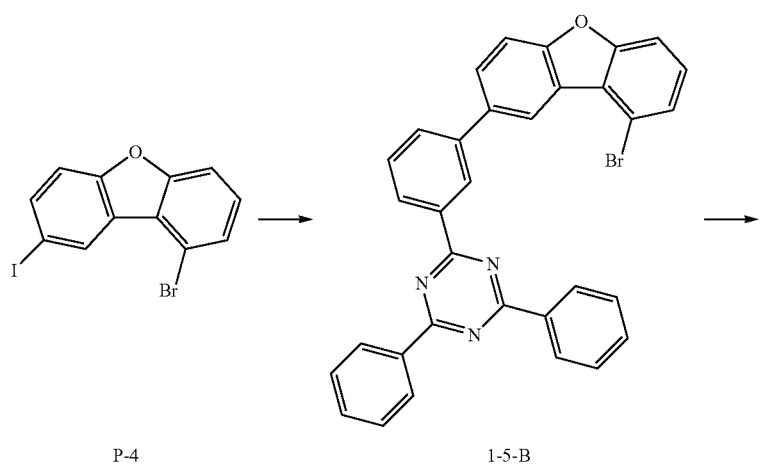

P-4

1-5-B

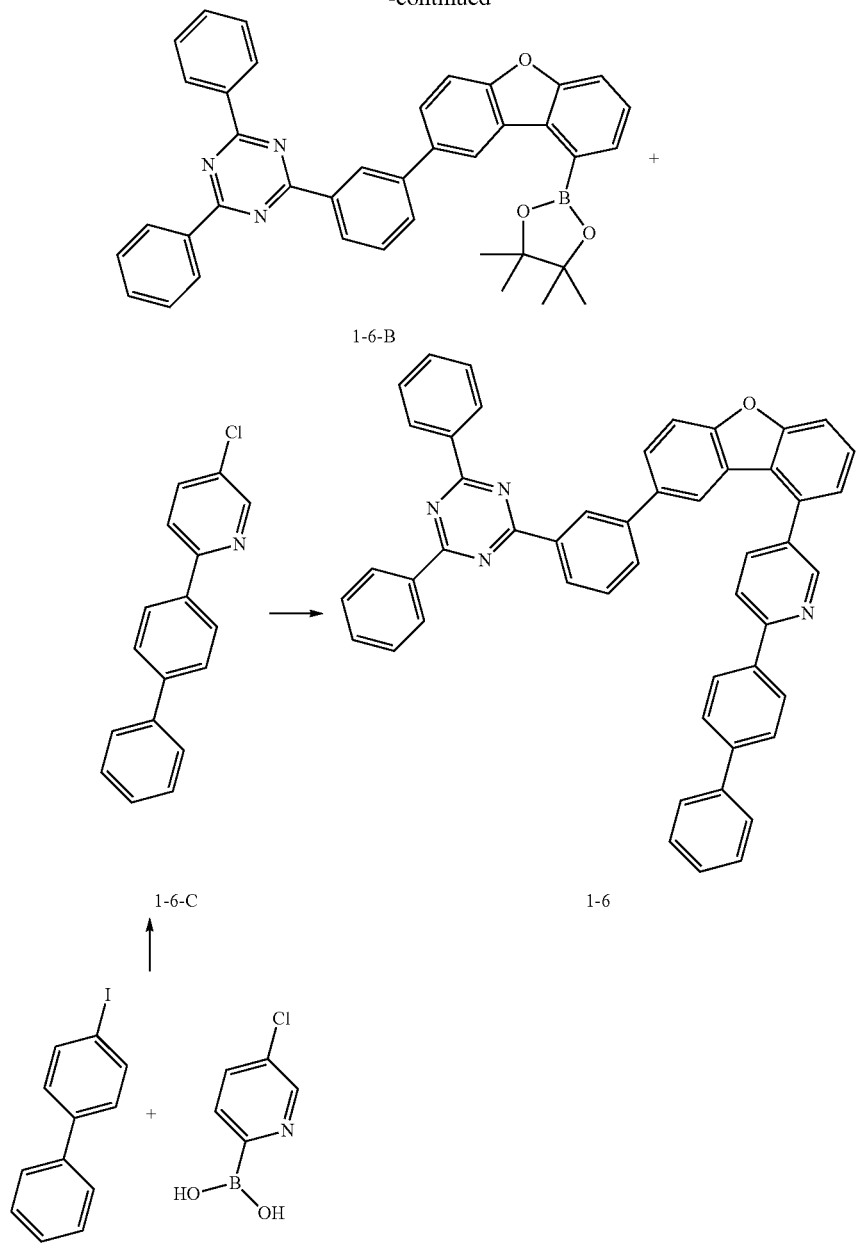

Step 1: Preparation of Compounds 1-6-A

Compound 1-6-A (26.2 g, yield 82%) was prepared in the same manner as in the preparation example of Compound 1-1-A using Intermediate P-4 (25 g, 67 mmol) and 2,4-diphenyl-6-(3-(4,4,5,5-tetraphenyl-1,3,2-dioxaboran-2-yl)phenyl-1,3,5-triazine (26.2 g, 67 mmol).

Step 2: Preparation of Compound 1-6-B

Compound 1-6-B (13.0 g, yield 80%) was prepared by conducting the experiment in the same manner as in the preparation example of Compound 1-1-B using Compound 1-6-A (17 g, 31 mmol).

Step 3: Preparation of Compound 1-6-C

Compound 1-6-C (13.2 g, yield 70%) was prepared by conducting the experiment in the same manner as in the preparation example of Compound 1-1-A using Compound 4-iodo-1,1'-biphenyl (20 g, 71 mmol) and (5-chloropyridin-2-yl)boronic acid.

Step 4: Preparation of Compound 1-6

Compound 1-6-B (23 g, 38 mmol) and Compound 1-6-C (10.2 g, 38 mmol) were added to 1,4-dioxane (150 mL) and potassium phosphate (24 g, 115 mmol) and waster (40 mL) was further added. 0.7 g (1.2 mmol) of dibenzylidene acetone palladium and 0.7 g (1.2 mmol) of tricyclohexylphosphine were added under stirring and reflux, followed by stirring under reflux for 12 hours. After completion of the reaction, the mixture was cooled to room temperature and the aqueous layer was removed. After concentrating the mixture under reduced pressure, the residue was dissolved in chloroform and washed with water to separate the organic layer. The separated organic layer was dried over anhydrous magnesium sulfate and filtered. The recrystallization was performed by adding ethyl acetate while concentrating under reflux to prepare Compound 1-6 (18.3 g, yield: 68%) MS: [M+H]⁺=705

Example 1-7: Preparation of Compound 1-7

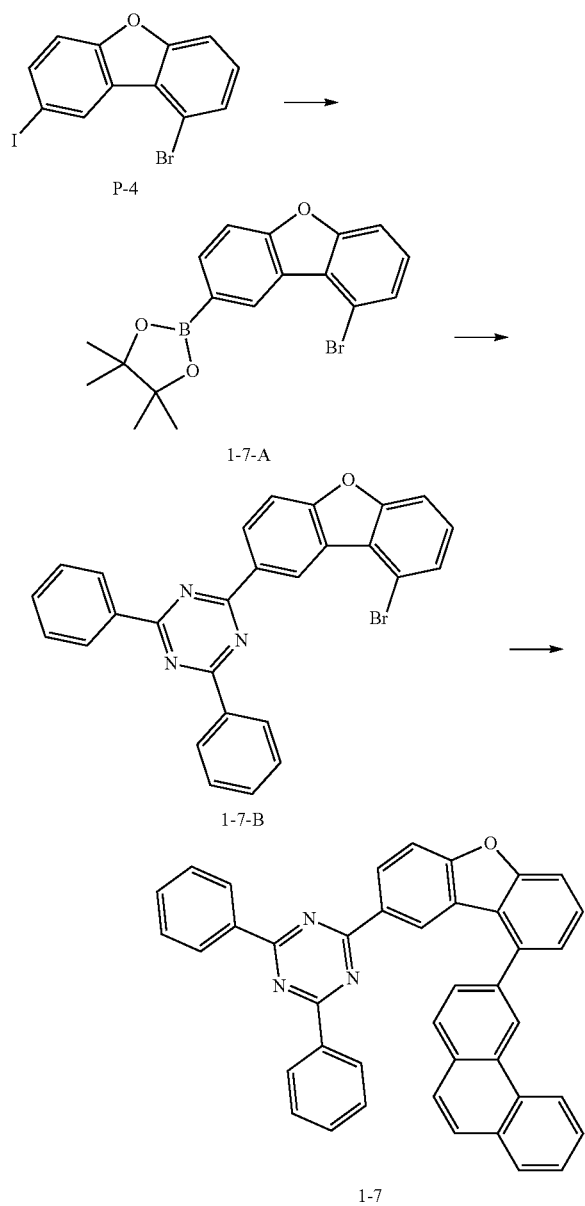

Step 1: Preparation of Compound 1-7-A

Compound 1-7-A (11.6 g, yield 77%) was prepared by conducting the experiment in the same manner as in the preparation example of Compound 1-1-B using Compound P-4 (15 g, 40 mmol).

Step 2: Preparation of Compound 1-7-B

Compound 1-7-B (9.0 g, yield 82%) was prepared by conducting the experiment in the same manner as in the preparation example of Compound 1-1 using Compound 1-7-A (11 g, 23 mmol) and 2-chloro-4,6-diphenyl-1,3,5-triazine (6.2 g, 23 mmol).

Step 3: Preparation of Compound 1-7

Compound 1-7 (8.4 g, yield 77%) was prepared in the same manner as in the preparation example of Compound 1-1 using Compound 1-7-B (9.0 g, 18.8 mmol) and phenanthrene-3-ylboronic acid (4.2 g, 19 mmol).

MS: [M+H]⁺=576

Example 2-1: Preparation of Compound 2-1

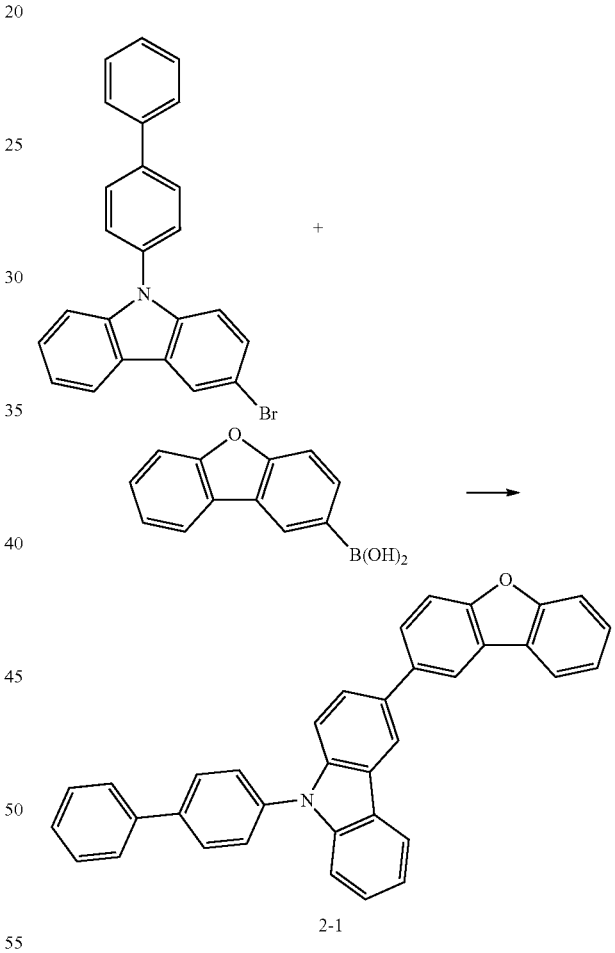

After compound 9-(1,1'-biphenyl)-4-yl)-3-bromo-9H-carbazole (15 g, 27 mmol) and compound dibenzo[b,d]furan-2-ylboronic acid (5.7 g, 27 mmol) were dissolved in tetrahydrofuran (80 mL), 2M aqueous potassium carbonate solution (aq. $K_2CO_3$) (40 ml, 81 mmol) was added, tetrakis(triphenylphosphine)palladium [Pd(PPh₃)₄] (0.3 g, 1 mol %) was added, and then the mixture was stirred and refluxed for 6 hours. The temperature was lowered to room temperature and the aqueous layer was removed, and the mixture was concentrated under reduced pressure. Ethyl acetate was added and the mixture was stirred under reflux for 1 hour, and cooled to room temperature and the solid was filtered. Chloroform was added to the resulting solid and dissolved under reflux. Ethyl acetate was added thereto and recrystallized to prepare Compound 2-1 (11.5 g, yield 73%).

MS: [M+H]$^+$=486

Example 2-2: Preparation of Compound 2-2

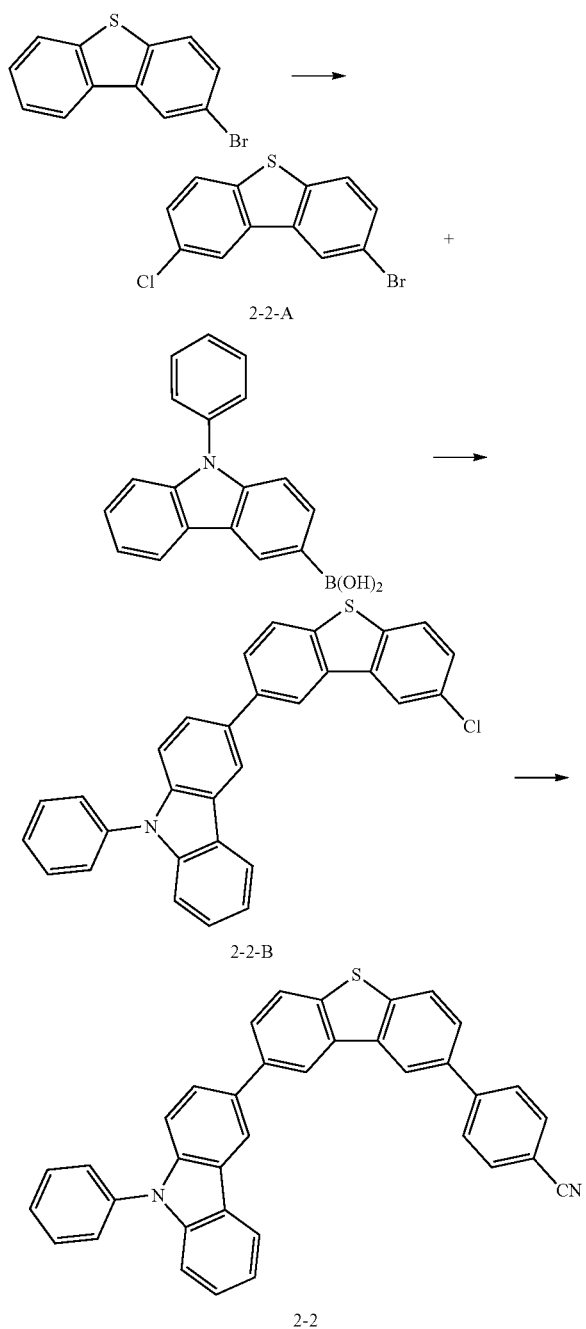

2-2-A 2-2-B 2-2

Step 1: Preparation of Compound 2-2-A

2-Chlorodibenzo[b,d]thiophene (22 g, 101 mmol) was dissolved in 50 mL of chloroform, cooled and the temperature was lowered to 0° C. Br$_2$ solution (5.5 mL, 108 mmol) was slowly added dropwise thereto. When the reaction was completed by stirring for 3 hours, an aqueous sodium carbonate solution was added and stirred. The aqueous layer was separated and the organic layer was collected, dried over anhydrous magnesium sulfate, filtered, and concentrated under reduced pressure. The concentrated compound was separated through column purification to give Compound 2-2-A (10 g, yield 49%).

Step 2: Production of Compound 2-2-B

After Compound 2-2-A (15 g, 50 mmol) and (9 phenyl-9H-carbazol-3-yl)boronic acid (15.2 g, 53 mmol) were dissolved in tetrahydrofuran (200 mL), 2M aqueous potassium carbonate solution (aq. K$_2$CO$_3$) (75 ml, 151 mmol) was added, tetrakis(triphenylphosphine)palladium [Pd(PPh$_3$)$_4$] (0.6 g, 1 mol %) was added, and then the mixture was stirred and refluxed for 6 hours. The temperature was lowered to room temperature and the aqueous layer was removed, and the mixture was concentrated under reduced pressure. Ethyl acetate was added and the mixture was stirred for 3 hours, and the precipitated solid was filtered. The obtained solid was further stirred with a mixed solution of chloroform and then filtered to prepare Compound 2-2-B (18.8 g, yield 81%).

Step 3: Preparation of Compound 2-2

After Compound 2-2-B (17 g, 37 mmol) and (4-cyanophenyl)boronic acid (5.7 g, 38.8 mmol) were dispersed in tetrahydrofuran (160 mL), 2M aqueous potassium carbonate solution (aq. K$_2$CO$_3$) (65 ml, 111 mmol) was added, tetrakis (triphenylphosphine)palladium [Pd(PPh$_3$)$_4$] (0.4 g, 1 mol %) was added, and then the mixture was stirred and refluxed for 6 hours. The temperature was lowered to room temperature and the aqueous layer was removed, and the mixture was concentrated under reduced pressure. The concentrated compound was dissolved in 300 mL of chloroform, washed with water and separated. The organic layer was treated with anhydrous magnesium sulfate and filtered. The filtrate was heated and a half was removed under reflux. 100 mL of ethyl acetate was added and recrystallized to prepare Compound 2-2 (14.2 g, yield 73%).

MS: [M+H]$^+$=527

Example 2-3: Preparation of Compound 2-3

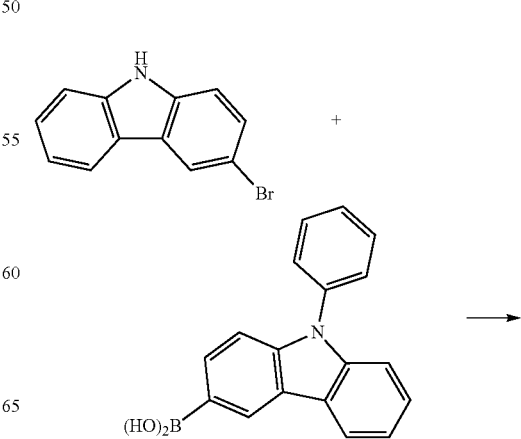

81

-continued

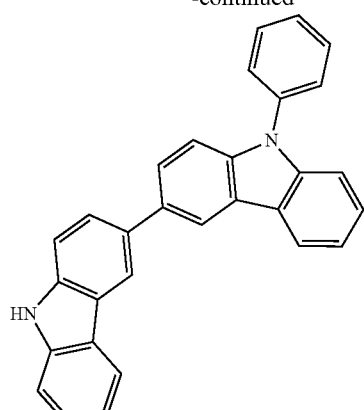

2-3-A

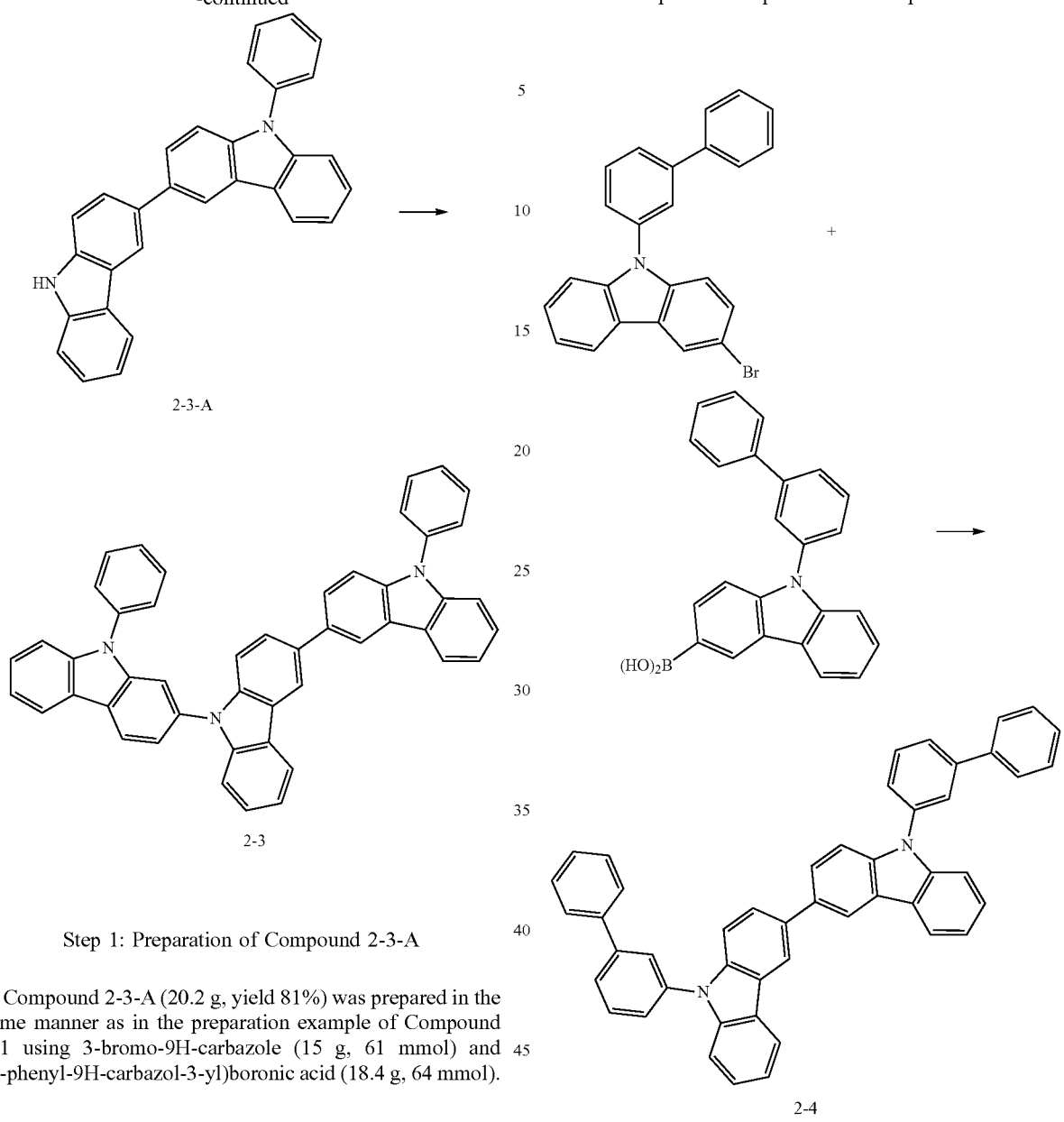

2-3

Step 1: Preparation of Compound 2-3-A

Compound 2-3-A (20.2 g, yield 81%) was prepared in the same manner as in the preparation example of Compound 2-1 using 3-bromo-9H-carbazole (15 g, 61 mmol) and (9-phenyl-9H-carbazol-3-yl)boronic acid (18.4 g, 64 mmol).

Step 2: Preparation of Compound 2-3

Compound 2-3-A (12 g, 30 mmol) and 2-bromo-9-phenyl-9H-carbazole (9.5 g, 30 mmol) were dissolved in 150 mL of toluene and sodium tert-butoxide (5.6 g, 59 mmol) was added and heated. Bis(tri-tert-butylphosphine)palladium (0.15 g, 1 mol %) was added thereto, and the mixture was refluxed and stirred for 12 hours. After completion of the reaction, the temperature was lowered to room temperature and the resulting solid was filtered. The pale yellow solid was dissolved in chloroform and washed twice with water. The organic layer was separated, and anhydrous magnesium sulfate and an acidic white clay were added thereto, stirred, filtered and distilled under reduced pressure. Recrystallization was performed using chloroform and ethyl acetate to obtain a white solid compound 2-3 (14.5 g, yield 76%).

MS: [M+H]⁺=650

82

Example 2-4: Preparation of Compound 2-4

2-4

Compound 2-4 (19.7 g, yield 77%) was prepared in the same manner as in the preparation example of Compound 2-1 using 9-([1,1'-biphenyl]-3-yl)-3-bromo-9H-carbazole (16 g, 40 mmol) and 9-([1,1'-biphenyl]-3-yl)-9H-carbazol-3-yl)boronic acid (14.6 g, 40 mmol).

MS: [M+H]⁺=637

Example 2-5: Preparation of Compound

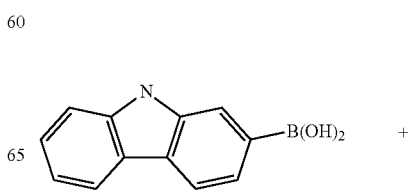

-continued

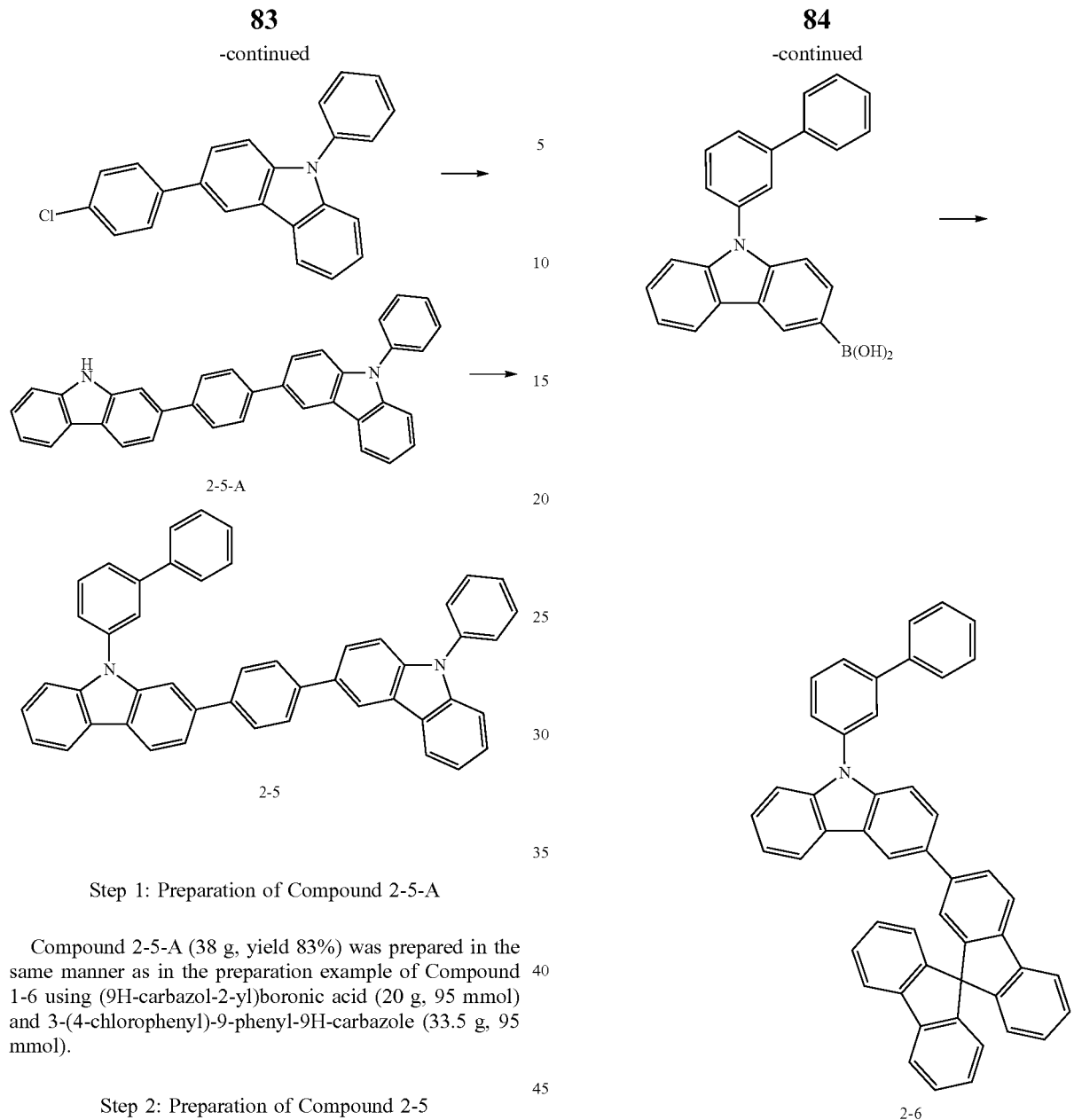

2-5-A 2-5

2-6

Step 1: Preparation of Compound 2-5-A

Compound 2-5-A (38 g, yield 83%) was prepared in the same manner as in the preparation example of Compound 1-6 using (9H-carbazol-2-yl)boronic acid (20 g, 95 mmol) and 3-(4-chlorophenyl)-9-phenyl-9H-carbazole (33.5 g, 95 mmol).

Step 2: Preparation of Compound 2-5

Compound 2-5 (15 g, yield 76%) was prepared in the same manner as in the preparation example of Compound 2-3 using Compound 2-5-A (15 g, 31 mmol) and 3-bromo-1,1'-biphenyl (7.2 g, 31 mmol).

MS: [M+H]⁺=637

Example 2-6: Preparation of Compound 2-6

Compound 2-6 (13.5 g, yield 75%) was prepared in the same manner as the preparation example of Compound 201 using 2-bromo-9,9'-spirobi[fluorene] (11 g, 29 mmol) and 9-([1,1'-biphenyl]-3-yl)-9H-carbazol-3-yl)boronic acid (10.4 g, 29 mmol).

MS: [M+H]⁺=634

Example 2-7: Preparation of Compound 2-7

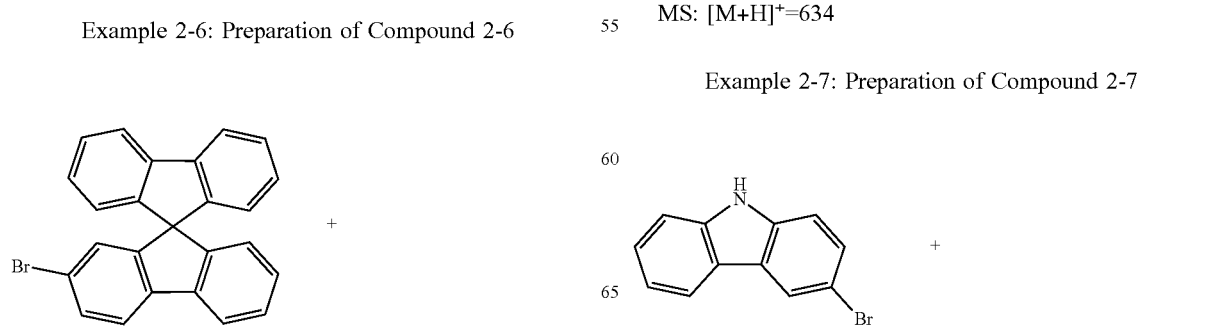

-continued

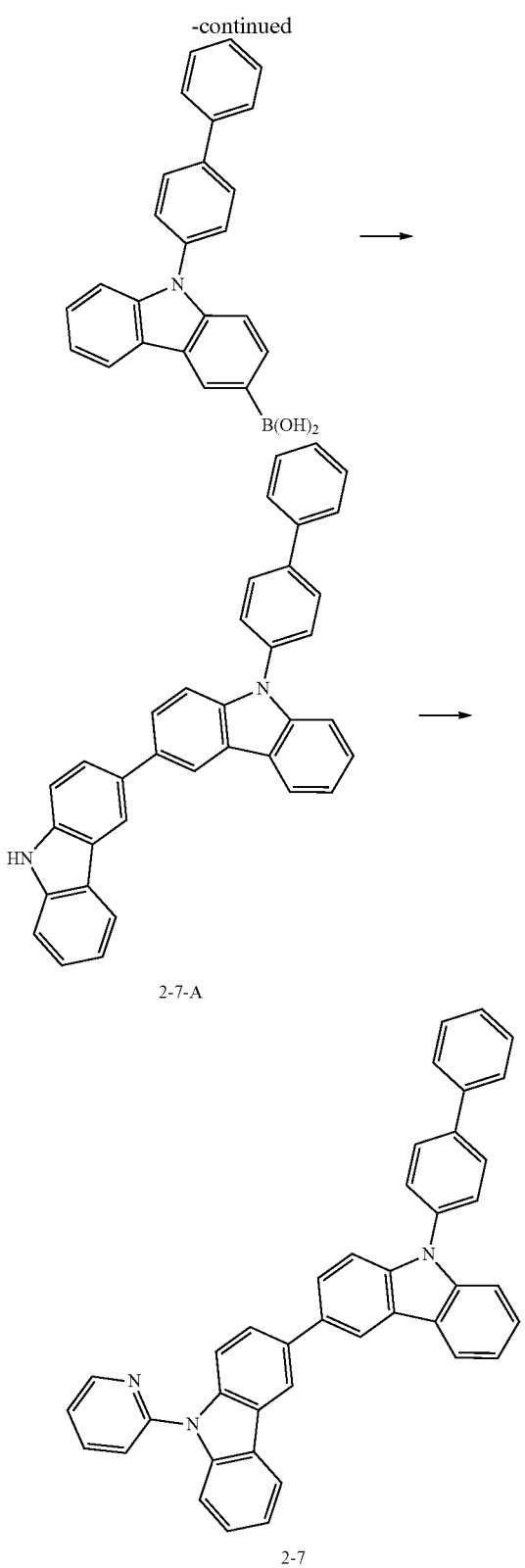

2-7-A 2-7

Step 1: Preparation of Compound 2-7-A

Compound 2-7-A (24 g, yield 81%) was prepared in the same manner as in the preparation example of Compound 2-1 using 3-bromo-9H-carbazole (15 g, 61 mmol) and 9-([1,1'-biphenyl]-4-yl)-9H-carbazol-3-yl)boronic acid (22 g, 61 mmol).

Step 2: Preparation of Compound 2-7

Compound 2-7 (8.5 g, yield 65%) was prepared in the same manner as in the preparation example of Compound 2-3 using Compound 2-7-A (13 g, 27 mmol) and 2-bromopyridine (4.3 g, 27 mmol).

MS: [M+H]$^+$=562

Experimental Example 1

A glass substrate on which a thin film of ITO (indium tin oxide) was coated in a thickness of 1,300 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator. On the ITO transparent electrode thus prepared, a compound of HI-1 as described below was thermally deposited under vacuum in a thicknesses of 50 Å to form the hole injection layer. On the hole injection layer, the compound of HT-1 was thermally deposited under vacuum in a thicknesses of 250 Å to form a hole transport layer, and a compound of HT-2 was deposited under vacuum in a thickness of 50 Å on the HT-1 deposited layer to form an electron blocking layer. Next, on the HT-2 vapor deposited layer, the compound 1-1 previously prepared and the compound 2-4 previously prepared were deposited by co-evaporation at a weight ratio (200:200) shown in Table 1 below, wherein the following compound of GD-1 as a phosphorescent dopant was co-deposited with the weight ratio (12%:relative to the total weight of Compound 1-1, Compound 2-4, and GD-1) to form a light emitting layer having a thickness of 400 Å shown in Table 1 below. The following compound of ET-1 was deposited on the light emitting layer in a thickness of 250 Å, and further, the following compound of ET-2 was co-deposited with a 2% by weight of Li in a thickness of 100 Å to form an electron transport layer and an electron injection layer. Aluminum was deposited on the electron injection layer in a thickness of 1000 Å to form a cathode.

HI-1

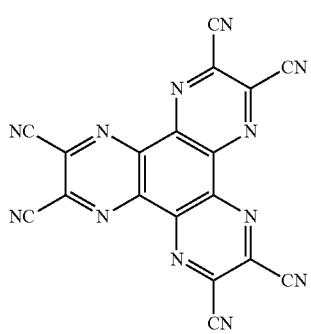

HT-1

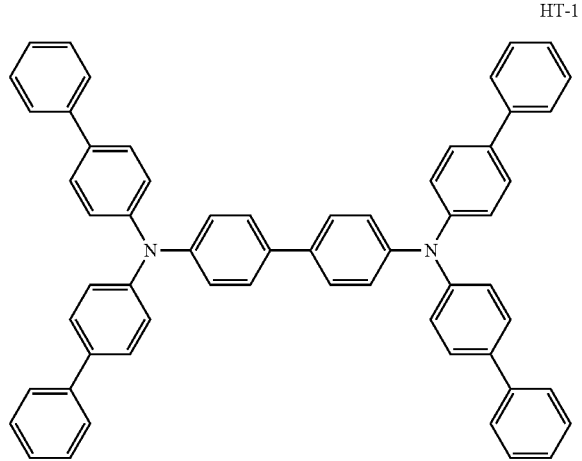

HT-2

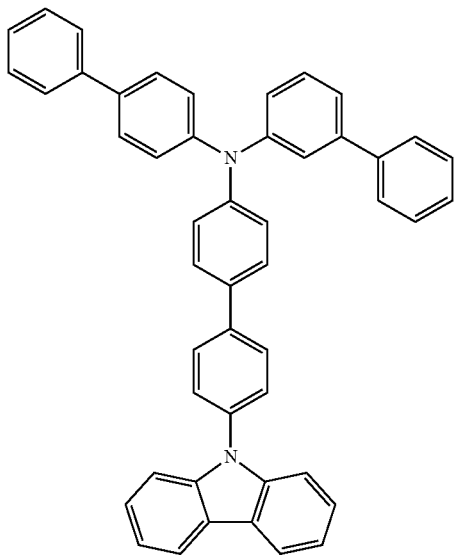

GD-1

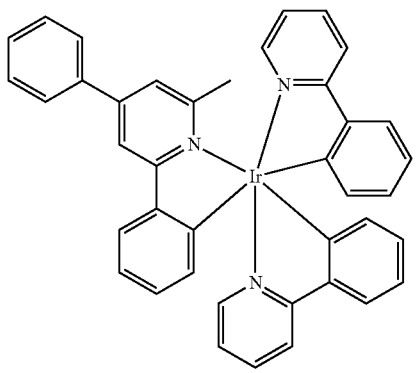

ET-1

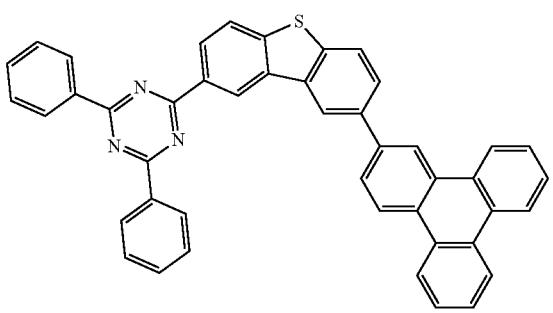

ET-2

In the above process, the vapor deposition rate of the organic material was maintained at 0.4 to 0.7 Å/sec, the deposition rate of aluminum was maintained at 2 Å/sec, and the degree of vacuum during vapor deposition was maintained at $1 \times 10^{-7} \sim 5 \times 10^{-8}$ torr.

Experimental Examples 2 to 9

The organic light emitting devices of Experimental Examples 2 to 9 were each fabricated in the same manner as in Experimental Example 1, except that the phosphorescent host material and the dopant content at the time of forming the light emitting layer were changed as shown in Table 1 below.

Comparative Experimental Examples 1 to 11

The organic light emitting devices of Comparative Experimental Examples 1 to 11 were each fabricated in the same manner as in Experimental Example 1, except that the phosphorescent host material and the dopant content at the time of forming the light emitting layer were changed as shown in Table 1 below. Here, the host materials A to E, PH-1 and PH-2 used are as follows.

Compound A

Compound B

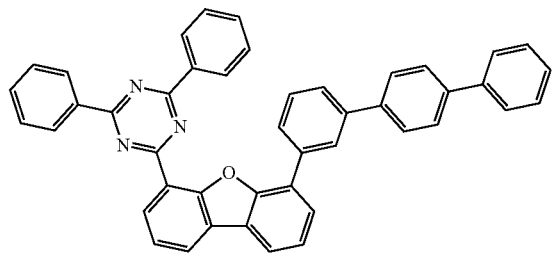

Compound C

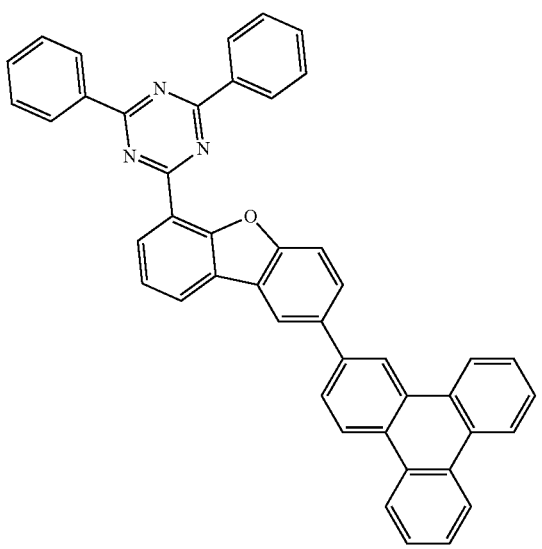

Compound D

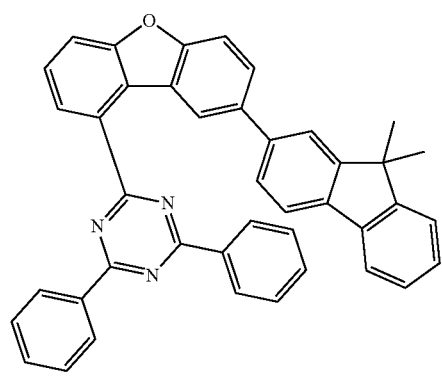

Compound E

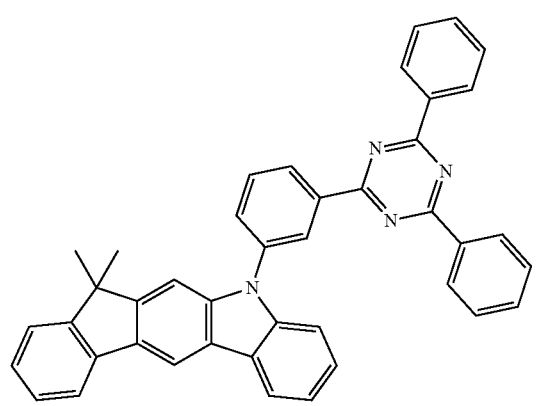

PH-1

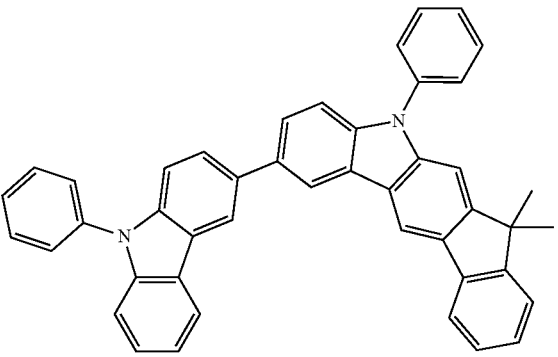

PH-2

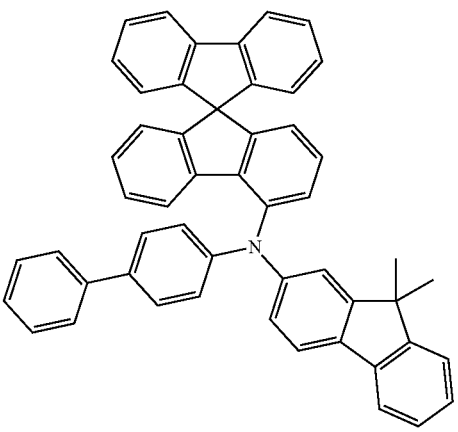

After an electric current was applied to each of the organic light emitting devices fabricated in Experimental Examples and Comparative Experimental Examples, the voltage, efficiency, luminance, color coordinate and lifetime were measured, and the results are shown in Table 1 below. In this case, T95 means the time required for the luminance to be reduced to 95% when the initial luminance at a light density of 20 mA/cm$^2$ was taken as 100%.

TABLE 1

| No. | (Host)/dopant content | Light emitting layer thickness (Å) | Voltage (V) (@10 mA/cm²) | EQE (%) | Color coordinate (x, y) | Life time (T95, h) |
|---|---|---|---|---|---|---|
| Experimental Example 1 | (Compound 1-1:Compound 2-4)/GD-1 (200:200)/12% | 400 | 3.25 | 19.5 | (0.35, 0.62) | 141.0 |
| Experimental Example 2 | (Compound 1-1:Compound 2-3)/GD-1 (200:200)/12% | 400 | 3.35 | 19.5 | (0.35, 0.61) | 126.4 |
| Experimental Example 3 | (Compound 1-2:Compound 2-5)/GD-1 (200:200)/12% | 400 | 3.44 | 19.4 | (0.35, 0.61) | 99.5 |
| Experimental Example 4 | (Compound 1-2:Compound 2-7)/GD-1 (200:200)/12% | 400 | 3.53 | 19.9 | (0.34, 0.62) | 124.8 |
| Experimental Example 5 | (Compound 1-3:Compound 2-4)/GD-1 (200:200)/6% | 400 | 3.14 | 18.8 | (0.34, 0.62) | 98.5 |
| Experimental Example 6 | (Compound 1-4:Compound 2-4)/GD-1 (200:200)/6% | 400 | 3.25 | 19.2 | (0.35, 0.61) | 72.7 |
| Experimental Example 7 | (Compound 1-5:Compound 2-4)/GD-1 (200:200)/6% | 400 | 3.41 | 19.5 | (0.34, 0.62) | 64.0 |
| Experimental Example 8 | (Compound 1-6:Compound 2-4)/GD-1 (120:280)/10% | 400 | 3.08 | 21.1 | (0.33, 0.63) | 67.2 |
| Experimental Example 9 | (Compound 1-7:Compound 2-3)/GD-1 (200:200)/10% | 400 | 3.22 | 19.7 | (0.32, 0.63) | 66.1 |
| Comparative Experimental Example 1 | (Compound 1-1)/GD-1 (400)/10% | 400 | 3.19 | 17.3 | (0.31, 0.63) | 37.5 |
| Comparative Experimental Example 2 | (Compound 1-1:PH-1)/GD-1 (150:150)/15% | 300 | 3.33 | 19.1 | (0.32, 0.63) | 55.1 |
| Comparative Experimental Example 3 | (Compound 1-1:PH-2)/GD-1 (200:200)/12% | 400 | 3.25 | 20.7 | (0.34, 0.62) | 45.3 |
| Comparative Experimental Example 4 | (Compound A)/GD-1 (300)/10% | 300 | 3.61 | 13.1 | (0.38, 0.59) | 12.1 |
| Comparative Experimental Example 5 | (Compound B:PH-1)/GD-1 (150:150)/15% | 300 | 3.43 | 19.0 | (0.32, 0.63) | 32.8 |
| Comparative Experimental Example 6 | (Compound C:Compound 2-4)/GD-1 (150:150)/10% | 300 | 3.33 | 18.5 | (0.32, 0.63) | 41.6 |
| Comparative Experimental Example 7 | (Compound D)/D-1 (400)/12% | 400 | 3.66 | 16.4 | (0.33, 0.63) | 30.2 |
| Comparative Experimental Example 8 | (Compound D:Compound 2-4)/GD-1 (120:280)/12% | 400 | 3.80 | 14.4 | (0.32, 0.63) | 43.1 |
| Comparative Experimental Example 9 | (Compound E)/GD-1 (400)/12% | 400 | 4.08 | 19.3 | (0.33, 0.63) | 14.9 |
| Comparative Experimental Example 10 | (Compound E:PH-2)/GD-1 (200:200)/12% | 400 | 4.23 | 20.3 | (0.35, 0.62) | 21.5 |
| Comparative Experimental Example 11 | (Compound E:Compound 2-5)/GD-1 (200:200)/12% | 400 | 3.54 | 20.0 | (0.34, 0.62) | 25.0 |

Experimental Example 10

A glass substrate on which a thin film of ITO (indium tin oxide) was coated in a thickness of 1,300 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of HI-1 described below was thermally deposited under vacuum in a thicknesses of 50 Å to form the hole injection layer. On the hole injection layer, a compound of HT-3 described below was thermally deposited under vacuum in a thicknesses of 800 Å to form a hole transport layer, and sequentially a compound of HT-4 described below was deposited under vacuum in a thickness of 500 Å to form the hole injection layer. Next, on the HT-3 vapor deposited layer, the compound 1-1 previously prepared and the compound 2-1 previously prepared were deposited by co-evaporation at a weight ratio (175:175) shown in Table 1 below, wherein the following compound GD-1 as a phosphorescent dopant was co-deposited with the weight ratio (5%:relative to the total weight of Compound 1-1, Compound 2-1, and GD-2) to form a light emitting layer having a thickness of 350 Å shown in Table 2 below. The following compound of ET-3 was deposited on the light emitting layer in a thickness of 50 Å to form a hole blocking layer. On the hole blocking layer, the following compound of ET-4 and LiQ were deposited under vacuum at a weight ratio of 1:1 to form an electron transport layer having a thickness of 250 Å. On the electron transport layer, lithium fluoride (LiF) was sequentially deposited in a thickness of 10 Å, and then aluminum was deposited in a thickness of 1000 Å to form a cathode.

HT-4

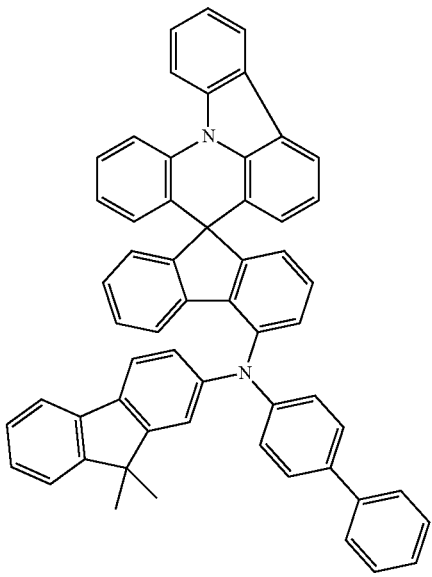

HI-1

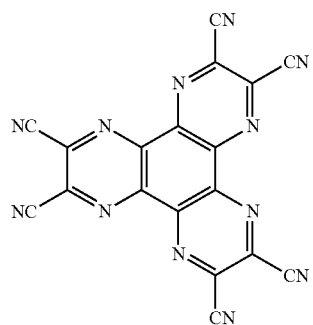

GD-2

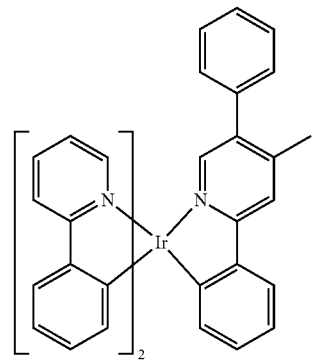

HT-3

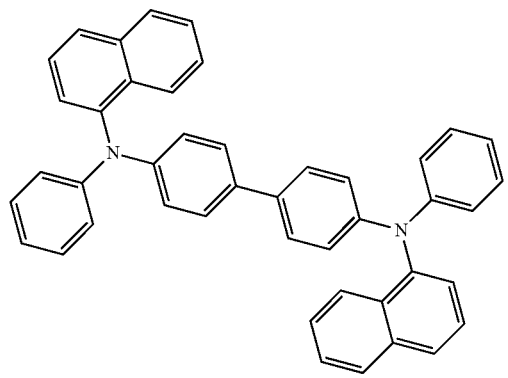

ET-3

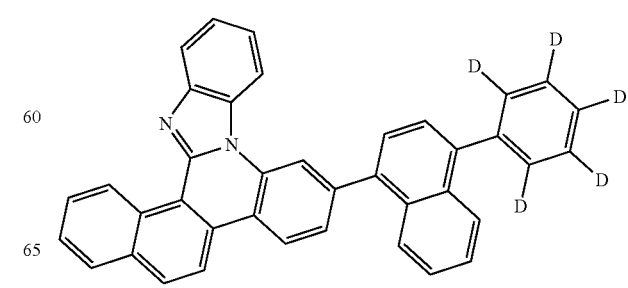

-continued

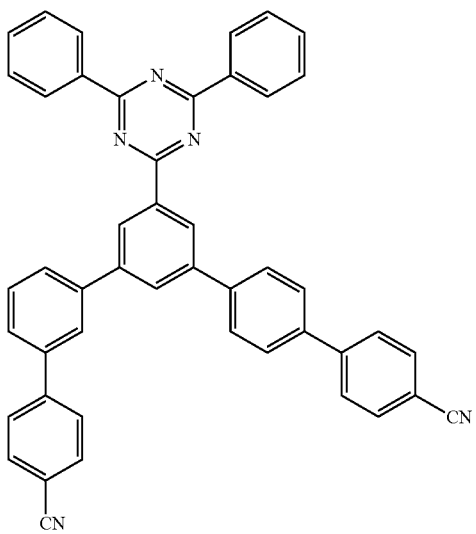
ET-4

In the above process, the vapor deposition rate of the organic material was maintained at 0.4 to 0.7 Å/sec, the lithium fluoride of the cathode was maintained at a deposition rate of 0.3 Å/sec, and the deposition rate of aluminum was maintained at 2 Å/sec. The degree of vacuum during vapor deposition was maintained at $1 \times 10^{-7} \sim 5 \times 10^{-8}$ torr.

Experimental Examples 11 to 18

The organic light emitting devices of Examples 11 to 18 were each fabricated in the same manner as in Experimental Example 10, except that the phosphorescent host material and the dopant content at the time of forming the light emitting layer were changed as shown in Table 2 below.

Comparative Experimental Examples 12 to 16

The organic light emitting devices of Comparative Experimental Examples 12 to 16 were each fabricated in the same manner as in Example 10, except that the phosphorescent host material and the dopant content at the time of forming the light emitting layer were changed as shown in Table 2 below. In this case, the host materials A, D and E used were the same as those previously used in Comparative Experimental Examples 1 to 11.

TABLE 2

| No. | (Host)/dopant content | Light emitting layer thickness (Å) | Voltage (V) (@10 mA/cm$^2$) | EQE (%) | Color coordinate (x, y) | Life time (T95, h) |
|---|---|---|---|---|---|---|
| Experimental Example 10 | (Compound 1-1:Compound 2-1)/GD-2 (175:175)/5% | 350 | 4.15 | 17.3 | (0.32, 0.63) | 189.5 |
| Experimental Example 11 | (Compound 1-1:Compound 2-2)/GD-2 (175:175)/5% | 350 | 4.20 | 17.5 | (0.32, 0.63) | 180.0 |
| Experimental Example 12 | (Compound 1-1:Compound 2-6)/GD-2 (140:210)/6% | 350 | 4.22 | 18.0 | (0.33, 0.63) | 140.9 |
| Experimental Example 13 | (Compound 1-2:Compound 2-2)/GD-2 (175:175)/5% | 350 | 3.93 | 18.1 | (0.32, 0.64) | 123.5 |
| Experimental Example 14 | (Compound 1-2:Compound 2-1)/GD-2 (200:200)/5% | 400 | 4.11 | 18.3 | (0.35, 0.61) | 158.1 |
| Experimental Example 15 | (Compound 1-3:Compound 2-1)/GD-2 (175:175)/5% | 350 | 4.06 | 18.4 | (0.33, 0.64) | 130.8 |
| Experimental Example 16 | (Compound 1-4:Compound 2-2)/GD-2 (200:200)/5% | 400 | 4.20 | 17.6 | (0.34, 0.62) | 133.7 |
| Experimental Example 17 | (Compound 1-5:Compound 2-2)/GD-2 (140:210)/5% | 350 | 4.26 | 17.6 | (0.33, 0.62) | 100.3 |
| Experimental Example 18 | (Compound 1-6:Compound 2-6)/GD-2 (175:175)/5% | 350 | 4.28 | 18.2 | (0.31, 0.64) | 133.0 |
| Comparative Experimental Example 12 | (Compound E:Compound 2-4)/GD-2 (175:175)/5% | 350 | 4.17 | 16.9 | (0.31, 0.64) | 61.8 |
| Comparative Experimental Example 13 | (Compound D:Compound 2-1)/GD-2 (200:200)/5% | 400 | 4.35 | 16.6 | (0.35, 0.61) | 65.0 |
| Comparative Experimental Example 14 | (Compound 1-1)/GD-2 (350)/5% | 350 | 3.78 | 15.5 | (0.35, 0.61) | 34.9 |
| Comparative Experimental Example 15 | (Compound A)/GD-2 (350)/6% | 350 | 3.97 | 14.1 | (0.35, 0.61) | 22.3 |
| Comparative Experimental Example 16 | (Compound A:Compound 2-2)/GD-2 (140:210)/6% | 350 | 4.51 | 18.2 | (0.34, 0.62) | 47.2 |

Experimental Example 19

HOMO and $PL_{max}$ (maximum emission wavelength) of the compound prepared in the above Examples were measured by the following methods.

1) HOMO Level Measurement

The HOMO level was measured using AC-3 equipment (Model AC-3 from Rinken Keiki). Specifically, as in Experimental Example 1, a compound to be measured was vacuum-evaporated in a thickness of 1000 Å on the ITO substrate used in the fabrication of the organic light emitting device to prepare a film. The quantum yield of the photon generated by irradiating the film with UV intensity of 10 nW was measured, and the results are shown in Table 3 below.

2) Measurement of $PL_{max}$ Value

The measurement was carried out using FP-8600 spectrofluorometer manufactured by JASCO. Specifically, a compound to be measured was vacuum-deposited on a bare glass in a thickness of 1000 Å to prepare a film, and the film was irradiated with UV rays of specific wavelengths and the emitted wavelengths were scanned. At this time, the position with the highest intensity in the obtained spectrum was determined as PLmax, and the result is shown in Table 3 below.

TABLE 3

| First host | HOMO (eV) | $PL_{max}$ (nm) | Second host | HOMO (eV) | $PL_{max}$ (nm) |
|---|---|---|---|---|---|
| Compound 1-1 | 5.99 | 447 | Compound 2-1 | 5.68 | 397 |
| Compound 1-2 | 5.95 | 443 | Compound 2-2 | 5.61 | 422 |
| Compound 1-3 | 5.93 | 445 | Compound 2-3 | 5.55 | 415 |
| Compound 1-4 | 5.98 | 441 | Compound 2-4 | 5.46 | 414 |
| Compound 1-5 | 6.02 | 420 | Compound 2-5 | 5.65 | 412 |
| Compound 1-6 | 6.30 | 407 | Compound 2-6 | 5.70 | 371 |
|  |  |  | Compound 2-7 | 5.58 | 432 |

$PL_{max}$ values of the mixture of the first host and the second host mixed at a weight ratio of 1:1 were measured in the same manner as described above, and the results are shown in FIGS. 3 and 4.

EXPLANATION OF SIGN

| 1: substrate | 2: anode |
|---|---|
| 3: light emitting layer | 4: cathode |
| 5: hole injection layer | 6: hole transport layer |
| 7: light emitting layer | 8: electron transport layer |

The invention claimed is:

1. An organic light emitting device, comprising:
a cathode;
an anode; and
at least one light emitting layer interposed between the cathode and the anode,
wherein the light emitting layer includes a first host compound of the following Chemical Formula 1-1 or Chemical Formula 1-2 and a second host compound of the following Chemical Formula 2:

[Chemical Formula 1-1]

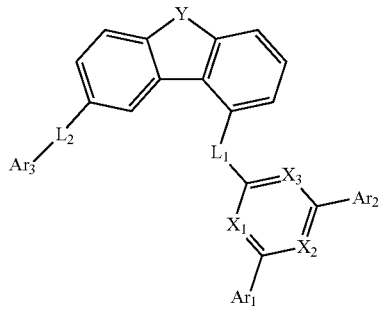

[Chemical Formula 1-2]

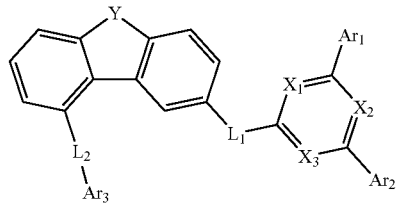

wherein in Chemical Formulae 1-1 and 1-2:

Y is O or S;

$X_1$ to $X_3$ are each independently N, or $CR_3$, and at least one of $X_1$ to $X_3$ is N;

$L_1$ is a single bond, a substituted or unsubstituted $C_{6-60}$ arylene, or a substituted or unsubstituted $C_{2-60}$ heteroarylene containing at least one of O, N, Si and S;

$L_2$ is a single bond;

$Ar_1$ and $Ar_2$ are each independently a substituted or unsubstituted $C_{6-60}$ aryl or a substituted or unsubstituted $C_{2-60}$ heteroaryl containing at least one of O, N, Si and S;

$Ar_3$ is any one selected from the group consisting of:

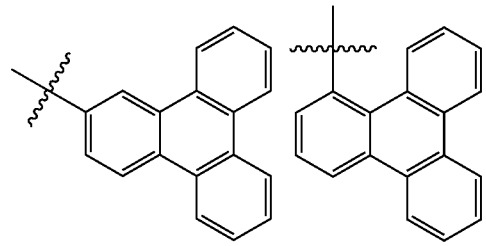

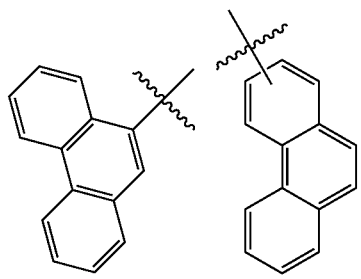

-continued

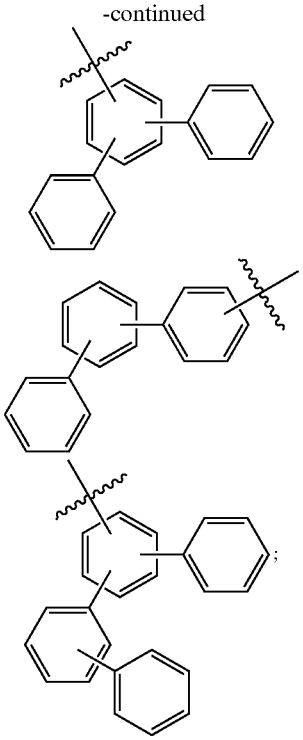

$R_3$ is hydrogen, deuterium, halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{1-60}$ heteroaryl containing at least one of O, N, Si and S;

[Chemical Formula 2]

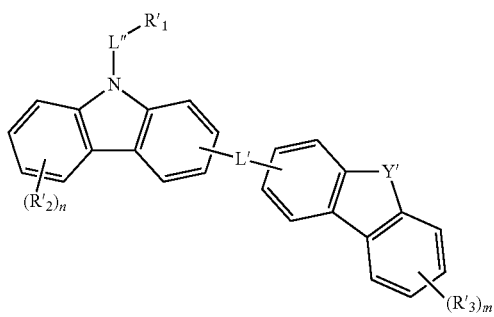

wherein in Chemical Formula 2:
Y' is O, S, or CR'R";
R' and R" are each independently hydrogen, deuterium, halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{6-60}$ heteroaryl containing at least one of O, N, Si and S, or R' and R" together form a substituted or unsubstituted $C_{6-60}$ aromatic ring;

L' is phenylene;
L" is a single bond or phenylene;
$R'_1$ is a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{2-60}$ heteroaryl containing at least one of O, N, Si and S;
$R'_2$ and $R'_3$ are each independently hydrogen, deuterium, halogen, cyano, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{2-60}$ heteroaryl containing at least one of O, N, Si and S; and
n and m are each independently an integer of 0 to 4.

2. The organic light emitting device of claim 1, wherein the compound of Chemical Formula 2 is any one selected from the group consisting of:

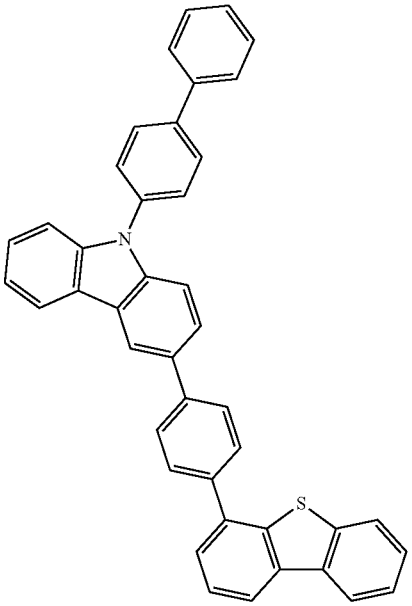

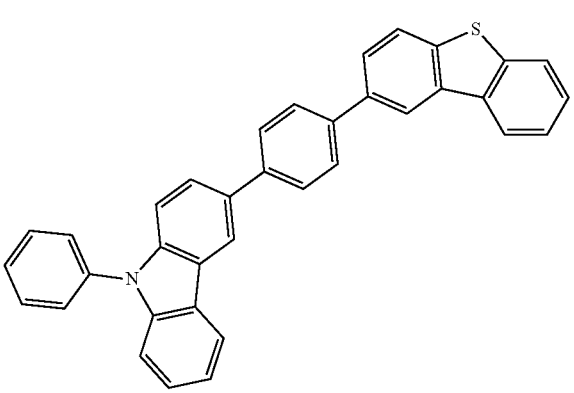

-continued

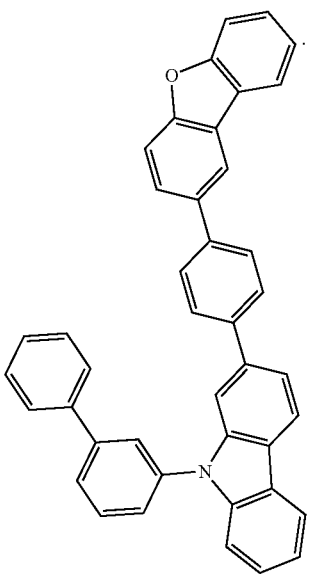

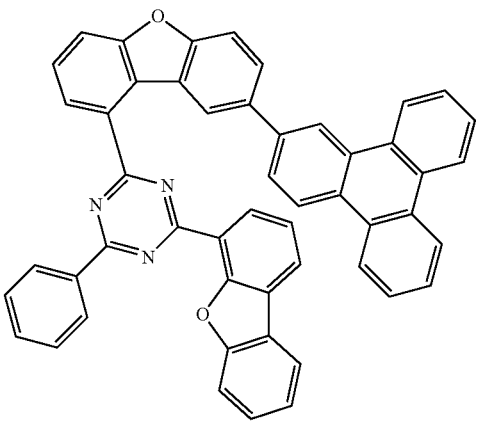

3. The organic light emitting device of claim 1, wherein $X_1$ to $X_3$ are each independently N or CH, provided that at least one of $X_1$ to $X_3$ is N.

4. The organic light emitting device of claim 1, wherein $L_1$ is a single bond, phenylene, phenylene substituted with cyano, or pyridinylene substituted with phenyl.

5. The organic light emitting device of claim 1, wherein $Ar_1$ and $Ar_2$ are each independently phenyl, phenyl substituted with cyano, phenyl substituted with one to five deuterium, biphenyl, or dibenzofuranyl.

6. The organic light emitting device of claim 1, wherein the compound of Chemical Formulae 1-1 or 1-2 is any one selected from the group consisting of:

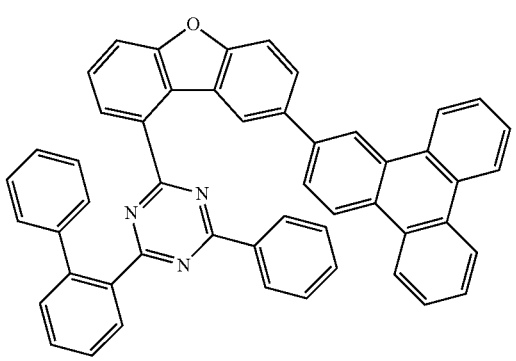

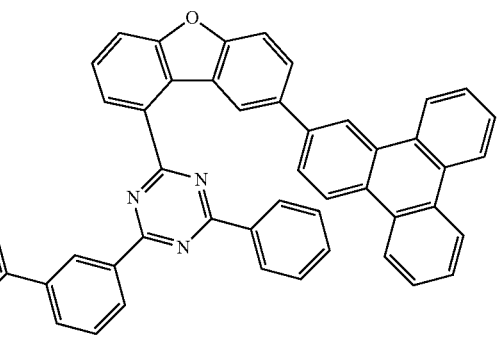

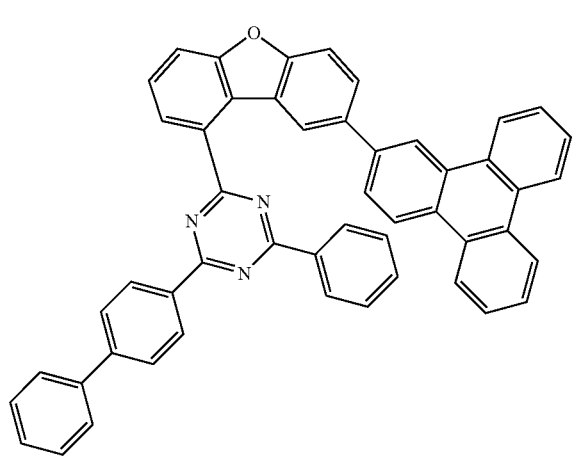

103
-continued
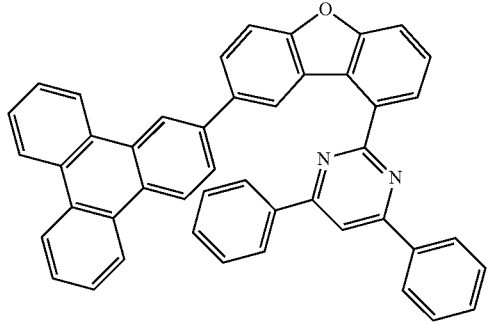
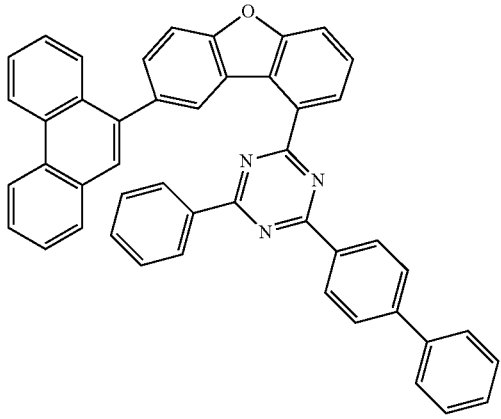
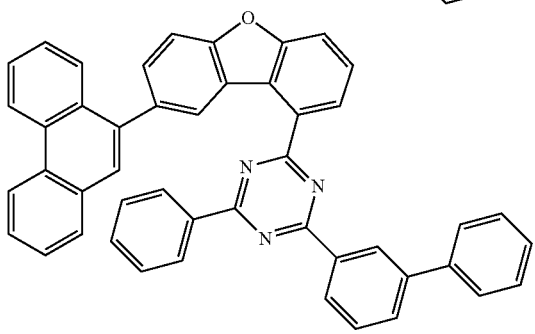
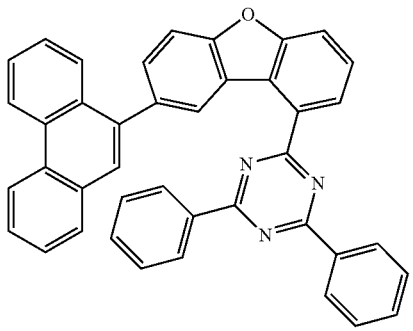
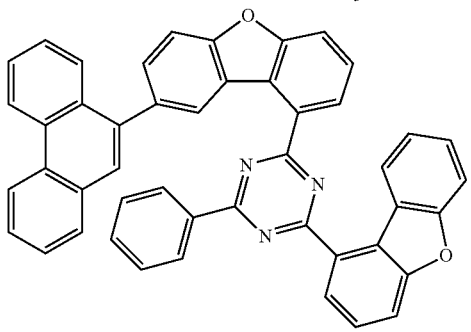
104
-continued
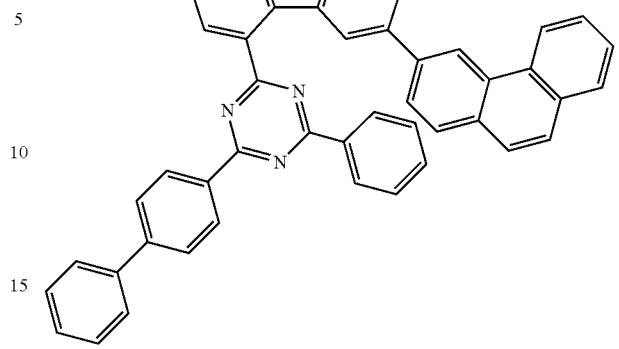
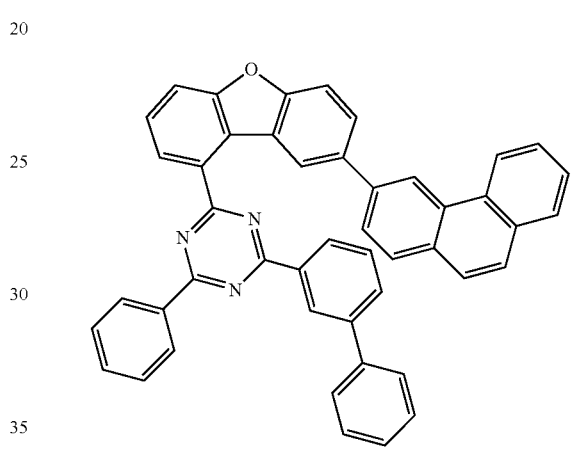
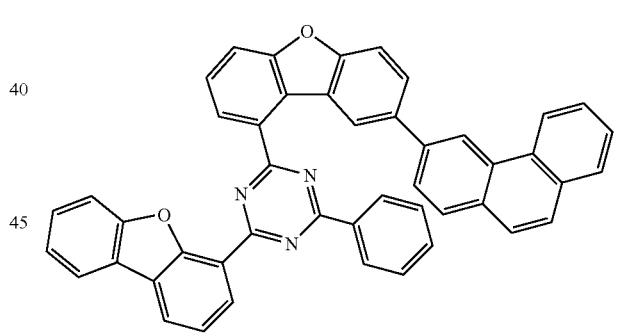
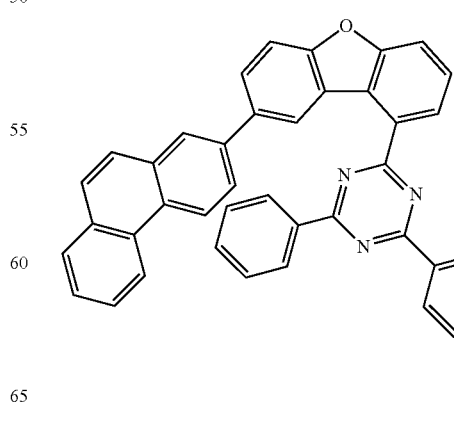

105
-continued
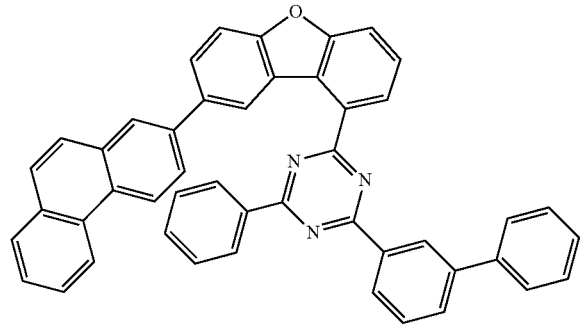
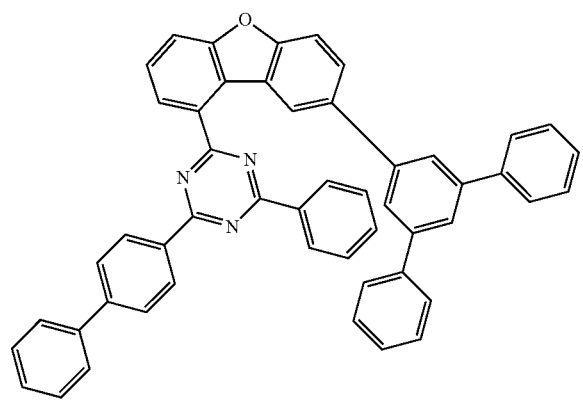
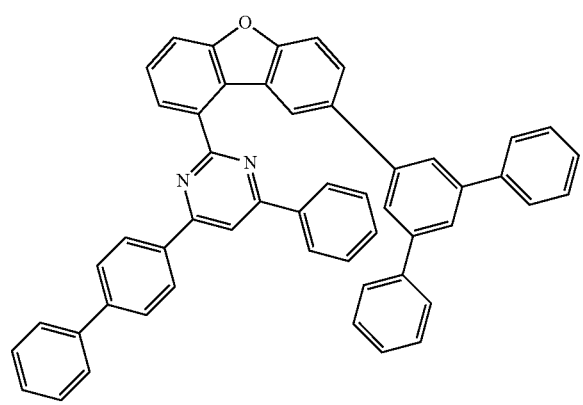
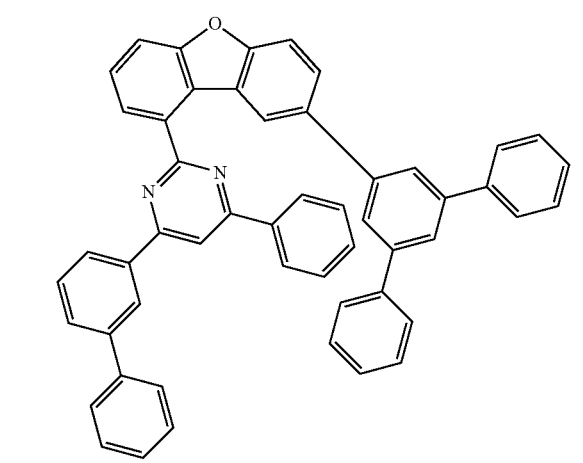
106
-continued
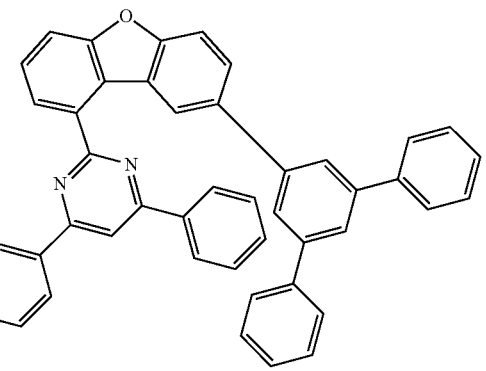
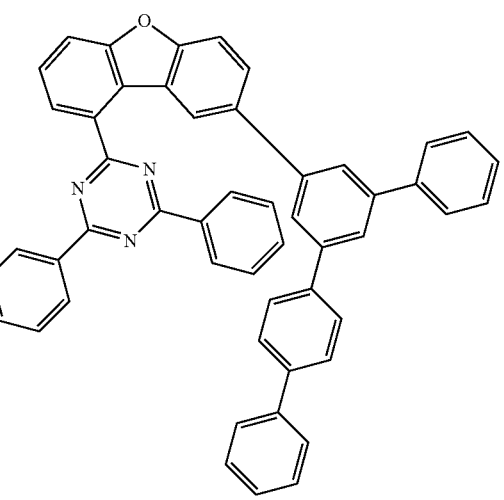
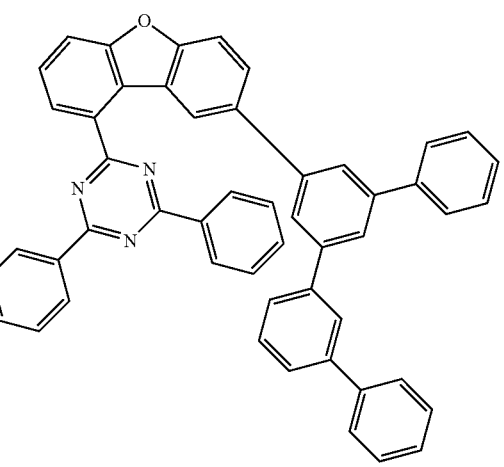
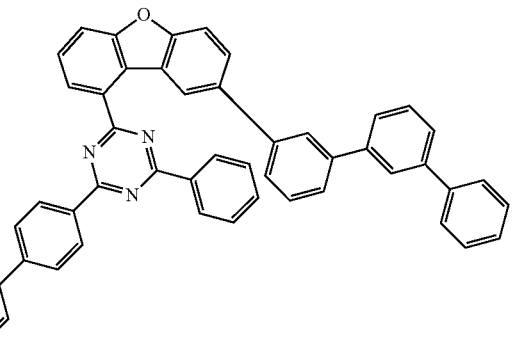

107
-continued
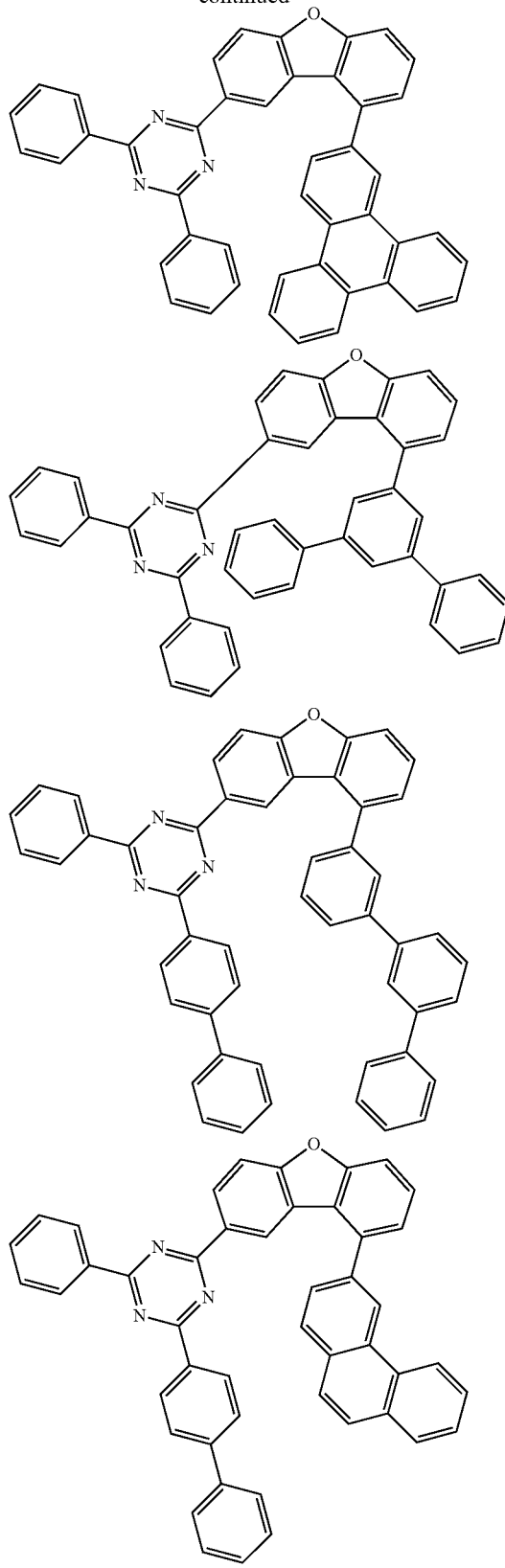
108
-continued
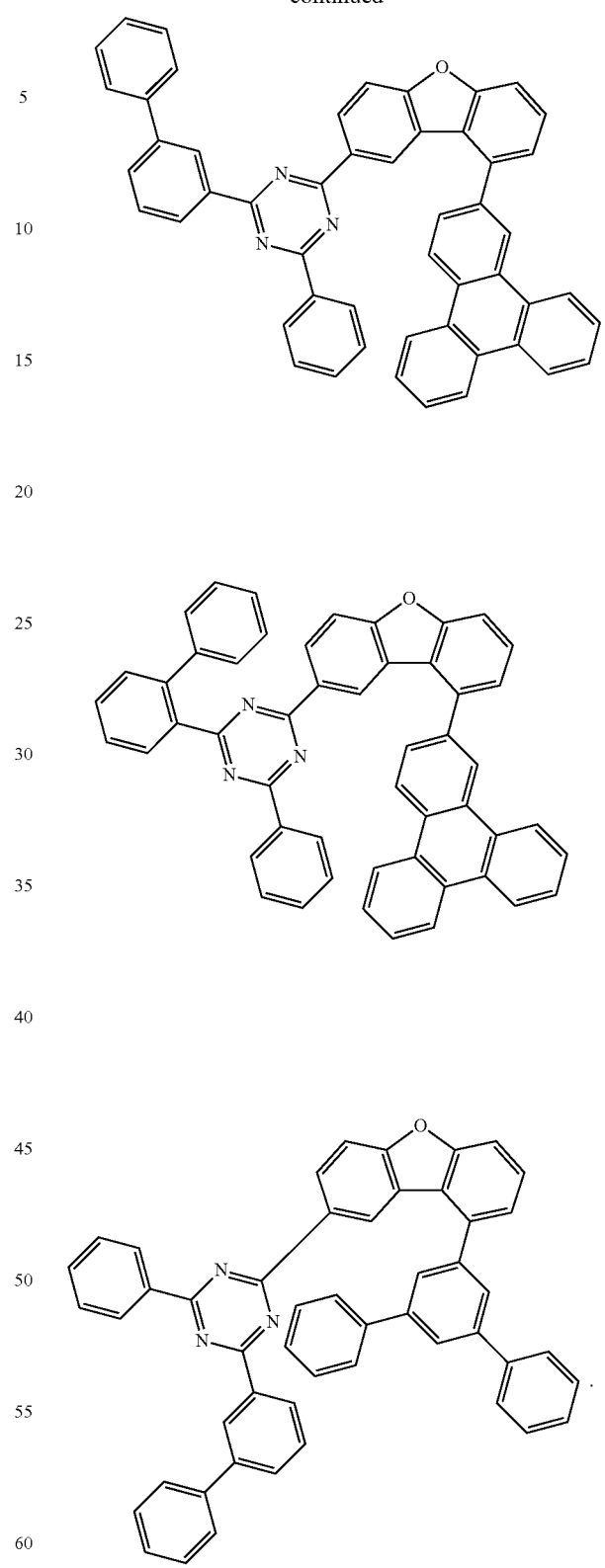
* * * * *